United States Patent
Qiao et al.

(10) Patent No.: US 8,946,430 B2
(45) Date of Patent: Feb. 3, 2015

(54) QUINOLINONE CARBOXAMIDE INHIBITORS OF ENDOTHELIAL LIPASE

(71) Applicant: Bristol-Myers Squibb Company, Princeton, NJ (US)

(72) Inventors: Jennifer X. Qiao, Princeton, NJ (US); Carol Hui Hu, New Hope, PA (US); Tammy C. Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/347,671

(22) PCT Filed: Sep. 24, 2012

(86) PCT No.: PCT/US2012/056847
§ 371 (c)(1),
(2) Date: Mar. 27, 2014

(87) PCT Pub. No.: WO2013/048942
PCT Pub. Date: Apr. 4, 2013

(65) Prior Publication Data
US 2014/0243314 A1  Aug. 28, 2014

Related U.S. Application Data

(60) Provisional application No. 61/541,126, filed on Sep. 30, 2011.

(51) Int. Cl.
| | | |
|---|---|---|
| *C07D 215/38* | (2006.01) | |
| *C07D 215/50* | (2006.01) | |
| *C07D 403/12* | (2006.01) | |
| *C07D 401/14* | (2006.01) | |
| *C07D 215/22* | (2006.01) | |
| *C07D 401/12* | (2006.01) | |
| *C07D 413/12* | (2006.01) | |
| *C07D 417/12* | (2006.01) | |
| *C07D 417/14* | (2006.01) | |

(52) U.S. Cl.
CPC ............ *C07D 215/50* (2013.01); *C07D 403/12* (2013.01); *C07D 401/14* (2013.01); *C07D 215/22* (2013.01); *C07D 401/12* (2013.01); *C07D 413/12* (2013.01); *C07D 417/12* (2013.01); *C07D 417/14* (2013.01)
USPC ............................. 546/156; 546/155; 514/312

(58) Field of Classification Search
USPC .................................. 546/155, 156; 514/312
See application file for complete search history.

(56) References Cited

U.S. PATENT DOCUMENTS

| 5,248,684 A * | 9/1993 | Suzuki et al. ................. 514/299 |
| 7,217,727 B2 | 5/2007 | Eacho et al. |
| 7,595,403 B2 | 9/2009 | Eacho et al. |
| 2006/0211755 A1 | 9/2006 | Eacho et al. |
| 2008/0287448 A1 | 11/2008 | Zoller et al. |
| 2009/0054478 A1 | 2/2009 | Zoller et al. |
| 2009/0076068 A1 | 3/2009 | Zoller et al. |

FOREIGN PATENT DOCUMENTS

| WO | WO99/32611 A1 | 7/1999 |
| WO | WO03/042179 A1 | 5/2003 |
| WO | WO2004/093872 A1 | 11/2004 |
| WO | WO2004/094393 A1 | 11/2004 |
| WO | WO2004/094394 A1 | 11/2004 |
| WO | WO2007/042178 A1 | 4/2007 |
| WO | WO2007/110215 A1 | 10/2007 |
| WO | WO2007/110216 A1 | 10/2007 |
| WO | WO2009/123164 A1 | 10/2009 |
| WO | WO2009/133834 A1 | 11/2009 |

OTHER PUBLICATIONS

Bevilacqua, M. et al., "Selectins", J. Clinical Invest., vol. 91, pp. 379-387 (1993).
deLemos, A. et al., "Identification of Genetic Variants in Endothelial Lipase in Persons With Elevated High-Density Lipoprotein Cholesterol", Circulation, vol. 106, pp. 1321-1326 (2002).
Folkman, J. et al., "Angiogenic Factors", Science, vol. 235, pp. 442-447 (1987).
Folkman, J. et al., "Angiogenesis" Minireview. The J. of Biological Chemistry, vol. 267(16) pp. 10931-10934 (1992).
Gordon, D.J. et al., "High-Density Lipoprotein—The Clinical Implications of Recent studies", New England J. of Medicine, vol. 321(19), pp. 1311-1116 (1989).
Gordon, D.J. et al., "High-Density Lipoprotein Cholesterol and Cardiovascular Disease", Circulation, vol. 79, pp. 8-15 (1989).
Hirata, K. et al., "Cloning of a Unique Lipase from Endothelial Cells Extends the Lipase Gene Family", The J. of Biological Chemistry, vol. 274(20), pp. 14170-14175 (1999).

(Continued)

*Primary Examiner* — D M Seaman
(74) *Attorney, Agent, or Firm* — Jing G. Sun

(57) ABSTRACT

The present invention provides compounds of Formula (I): as defined in the specification and compositions comprising any of such novel compounds. These compounds are endothelial lipase inhibitors which may be used as medicaments.

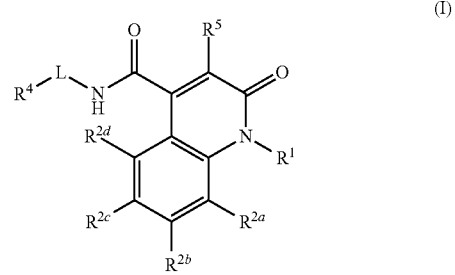

14 Claims, No Drawings

(56) References Cited

OTHER PUBLICATIONS

Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522 (1992).

Jaye, M. et al., "A novel endothelial-derived lipase that modulates HDL metabolism", Nature Genetics, vol. 21, pp. 424-428 (1999).

Jin, W. et al., "Lipases and HDL metabolism" Trends in Endocrinology & Metabolism, vol. 13(4), pp. 174-178 (2002).

Lamas, S. et al., "Endothelial nitric oxide synthase: Molecular cloning and characterization of a distinct constitutive enzyme isoform", PNAS, vol. 89, pp. 6348-6352 (1992).

Lüscher, T.F. et al., "Endothelium-Derived Contracting Factors", Hypertension, vol. 19, pp. 117-130 (1992).

McCoy, M.G. et al., "Characterization of the lipolytic activity of endothelial lipase", Journal of Lipid Research, vol. 43, pp. 921-929 (2002).

Ross, R., "The pathogenesis of atherosclerosis: a perspective for the 1990s" Nature, vol. 362(80), pp. 801-809 (1993).

Sing-Yuen Sit et al., "3-Hydroxy-Quinolin-2-ones: Inhibitors of [$^3$H]-Glycine Binding to the Site Associated with the NMDA Receptor", Bioorganic & Medicinal Chemistry Letters, vol. 6(5), pp. 499-504 (1996).

Strauss, J.G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).

Williams, T.J. et al., "Adhesion Molecules Involved in the Microvascular Inflammatory Response", Am Rev. Respir. Disease, vol. 146, pp. S45-S50 (1992).

Wong, H. et al., "The lipase gene family", Journal of Lipid Research, vol. 43, pp. 993-999 (2002).

Yanagisawa, M. et al,, "A novel potent vasoconstrictor peptide produced by vascular endothelial cells", Nature, vol. 332, pp. 411-15 (1988).

* cited by examiner

QUINOLINONE CARBOXAMIDE INHIBITORS OF ENDOTHELIAL LIPASE

CROSS-REFERENCE TO RELATED APPLICATIONS

The present application is a 371 application of PCT/US2012/056847 filed Sep. 24, 2012, which claims priority benefit of U.S. provisional application Ser. No. 61/541,126, filed Sep. 30, 2011, each of which is fully incorporated by reference herein.

FIELD OF THE INVENTION

The present invention provides novel quinolinone carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, *Nature*, 362(80):1-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon et al., *N Engl. J. Med.*, 321:1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 13:174-178 (2002); Wong et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata et al., *J. Biol. Chem.*, 274:14170-14175 (1999); Jaye et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel quinolinone carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

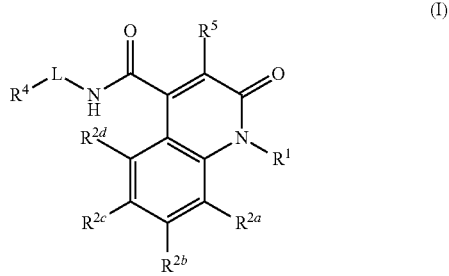

or a stereoisomer, a tautomer, a pharmaceutically acceptable salt, or a solvate thereof, wherein:

R[1] is independently selected from the group consisting of: H, $C_{1-6}$ alkyl substituted with 0-3 R[a], $C_{2-6}$ alkenyl substituted with 0-3 R[a], and —$(CH_2)_n$—W—$(CH_2)_m$—R[1a];

W is independently selected from the group consisting of: a bond, NH, O, S, N($C_{1-4}$ alkyl), CO, CONH, CON($C_{1-4}$ alkyl), NHCO, $SO_2$, $NHSO_2$, $SO_2NH$, $NHCO_2$, and CHR[f];

R[1a] is independently selected from the group consisting of: $C_{3-10}$ carbocycle and a 5- to 10-membered heterocycle comprising: carbon atoms and 1-4 heteroatoms selected from N, NR[e], O, and $S(O)_p$; and wherein said carbocycle and heterocycle are substituted with 0-3 R[c];

R[2a], R[2b], R[2c], and R[2d] are, independently at each occurrence, selected from the group consisting of: H, halogen, OH, $C_{1-4}$ alkyl, $C_{1-2}$ alkenyl, $C_{1-4}$ haloalkyl, $C_{1-4}$ alkoxy, $C_{1-4}$ haloalkoxy, $CF_3$, $OCF_3$, $OCF_2CHF_2$, CN, $NH_2$, $NO_2$, NH($C_{1-4}$ alkyl), N($C_{1-4}$ alkyl)$_2$, $CO_2H$, $CO_2$($C_{1-4}$ alkyl), $CONH_2$, CONH($C_{1-4}$ alkyl), CON($C_{1-4}$ alkyl)$_2$, $NHSO_2$($C_{1-4}$ alkyl), $SO_2$($C_{1-4}$ alkyl), $SO_2NH_2$, and phenyl substituted with 0-2 R[b];

R[4] is independently selected from the group consisting of: $C_{3-10}$ carbocycle and a 5- to 10-membered heterocycle comprising: carbon atoms and 1-4 heteroatoms selected from N, NR[e], O, and $S(O)_p$; wherein said carbocycle and heterocycle are substituted with 0-3 R[d];

R[5] is independently selected from the group consisting of: OR[6], CN, and NR[7]R[8];

R[6] is independently selected from the group consisting of: H and $C_{1-6}$ alkyl substituted with 0-1 $CO_2H$;

R[7] is independently selected from the group consisting of: H, $C_{1-6}$ alkyl substituted with 0-1 R[a], —$(CH_2)_n$-(phenyl substituted with 0-3 R[b]), and —$(CH_2)_n$-(5- to 6-membered heterocycle comprising: carbon atoms and 1-4 heteroatoms selected from N, NR[e], O, and $S(O)_p$); and wherein said heterocycle is substituted with 0-3 R[c];

R[8] is independently selected from the group consisting of: H and $C_{1-6}$ alkyl;

alternatively, NR[7]R[8] is a 5- to 6-membered heterocycle comprising: carbon atoms and 1-4 heteroatoms selected from N, NR[e], O, and $S(O)_p$;

L is independently a hydrocarbon or hydrocarbon-heteroatom linker optionally substituted with 0-2 R[g]; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —$SO_2$—, NH, and N($C_{1-4}$ alkyl);

alternatively, L is $X_1$—Y—$X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-2 R[g]; said hydrocarbon linker has one to six carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-10}$ carbocycle and a 4- to 10-membered heterocycle comprising: carbon atoms and 1-4 heteroatoms selected from N, NR[e], O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, R[4]-L- is

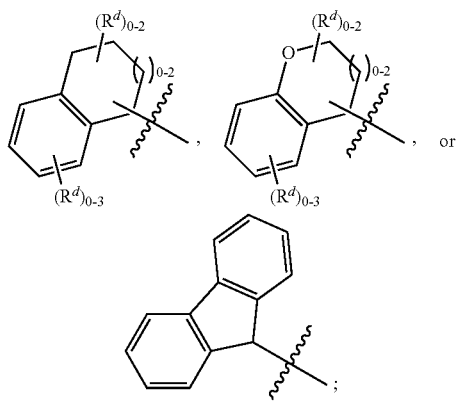

R[a] is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, NH($C_{1-4}$ alkyl), N($C_{1-4}$ alkyl)$_2$, $CO_2H$, $CO_2$($C_{1-4}$ alkyl), NHCO($C_{1-4}$ alkyl substituted with 0-1 $NH_2$), N($C_{1-4}$ alkyl)CO($C_{1-4}$ alkyl), $NHCO_2$($C_{1-4}$ alkyl), $CONHSO_2$($C_{1-4}$ alkyl), $SO_2$($C_{1-4}$ alkyl), $CONH_2$, CONH($C_{1-4}$ alkyl), $NHSO_2$($C_{1-4}$ alkyl), N($C_{1-4}$ alkyl)$SO_2$($C_{1-4}$ alkyl), and phenoxy;

R[b] is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, NH($C_{1-4}$ alkyl), N($C_{1-4}$ alkyl)$_2$, $CO_2H$, $CO_2$($C_{1-4}$ alkyl), $CONH_2$, CONH($C_{1-4}$ alkyl), CON($C_{1-4}$ alkyl)$_2$, $NHCO_2$($C_{1-4}$ alkyl), $NHSO_2$($C_{1-4}$ alkyl), N($C_{1-4}$ alkyl)$SO_2$($C_{1-4}$ alkyl), $SO_2$($C_{1-4}$ alkyl), $SO_2NH_2$, phenyl, benzyl, and phenoxy;

R[c] is, independently at each occurrence, selected from the group consisting of: =O and R[b];

R[d] is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, NH($C_{1-4}$ alkyl), N($C_{1-4}$ alkyl)$_2$, $CO_2H$, $CO_2$($C_{1-4}$ alkyl), CO($C_{1-4}$ alkyl), NHCO($C_{1-4}$ alkyl), —$CH_2NHCO$($C_{1-4}$ alkyl), $CONH_2$, CONH($C_{1-4}$ alkyl), CON($C_{1-4}$ alkyl)$_2$, $SO_2$($C_{1-4}$ alkyl), $SO_2NH_2$, —$SO_2NH$($C_{1-4}$ alkyl), —$SO_2NH$($C_{3-6}$ cycloalkyl), —$NHSO_2$($C_{1-4}$ alkyl), —$CH_2NHSO_2$($C_{1-4}$ alkyl), Si($C_{1-4}$ alkyl)$_3$, and phenyl optionally substituted with one or two substituents independently selected from: halogen, OH, $C_{1-4}$ alkyl, $C_{1-4}$ haloalkyl, $C_{1-4}$ alkyoxy, and NHCO($C_{1-4}$ alkyl);

R[e] is, independently at each occurrence, selected from the group consisting of: H, $C_{1-4}$ alkyl, CO($C_{1-4}$ alkyl), $CO_2$($C_{1-4}$ alkyl), $CO_2$(benzyl), and —$(CH_2)_n$-(phenyl optionally substituted with 0-2 halogens);

R[f] is, independently at each occurrence, selected from the group consisting of: $C_{1-4}$ alkyl, $C_{2-4}$ alkenyl, $CO_2$($C_{1-4}$ alkyl), $CONH_2$, $C_{3-6}$ cycloalkyl, phenyl, and benzyl;

R[g] is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2$($C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4; and p is, independently at each occurrence, selected from 0, 1, and 2;

provided that: when L is $CH_2$, $R^1$ is H and $R^5$ is OH, then $R^4$ is other than an unsubstituted phenyl.

In a second aspect, the present invention includes a compound of Formula (I), or a stereoisomer, a tautomer, a pharmaceutically acceptable salt, or a solvate thereof, within the scope of the first aspect, wherein:

$R^1$ is independently selected from the group consisting of: $C_{1-6}$ alkyl substituted with 0-2 $R^a$, $C_{2-6}$ alkenyl substituted with 0-2 $R^a$, and $-(CH_2)_n-W-R^{1a}$;

W is independently selected from the group consisting of: a bond, NH, N($C_{1-4}$ alkyl), CO, CONH, CON($C_{1-4}$ alkyl), $SO_2$, $NHCO_2$, and $CHR^f$;

$R^{1a}$ is independently selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^{2a}$, $R^{2b}$ and $R^{2c}$ are, independently at each occurrence, selected from the group consisting of: H, halogen, OH, $C_{1-4}$ alkyl, $C_{1-2}$ alkenyl, $C_{1-4}$ haloalkyl, $C_{1-4}$ alkoxy, $CF_3$, $OCF_3$, $OCF_2CHF_2$, $OCH_2CF_3$, $OCF_2CF_3$, $OCH_2CF_2CF_3$, $NH_2$, $NO_2$, NH($C_{1-4}$ alkyl), N($C_{1-4}$ alkyl)$_2$, $CO_2H$, $CO_2$($C_{1-4}$ alkyl), $CONH_2$, CONH($C_{1-4}$ alkyl), CON($C_{1-4}$ alkyl)$_2$, $NHSO_2$($C_{1-4}$ alkyl), $SO_2$($C_{1-4}$ alkyl), $SO_2NH_2$, and phenyl substituted with 0-2 $R^b$;

$R^{2d}$ is independently selected from the group consisting of: H, halogen, OH, $C_{1-4}$ alkyl, and $NH_2$;

$R^4$ is independently selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is independently selected from the group consisting of: OH, O($C_{1-4}$ alkyl substituted with 0-1 $CO_2H$), CN, and $NR^7R^8$;

L is independently a hydrocarbon or hydrocarbon-heteroatom linker optionally substituted with 0-1 $R^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —$SO_2$—, NH, and N($C_{1-4}$ alkyl);

alternatively, L is $X_1-Y-X_2$;

$X_1$ and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-7}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

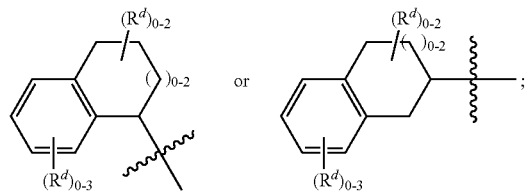

provided that: when L is $CH_2$, $R^1$ is H and $R^5$ is OH, then $R^4$ is other than an unsubstituted phenyl.

In a third aspect, the present invention includes a compound of Formula (I), or a stereoisomer, a tautomer, a pharmaceutically acceptable salt, or a solvate thereof, within the scope of the first or second aspect, wherein:

$R^1$ is independently selected from the group consisting of: $C_{1-6}$ alkyl substituted with 0-2 $R^a$, $C_{2-6}$ alkenyl substituted with 0-2 $R^a$, and $-(CH_2)_n-W-R^{1a}$;

W is independently selected from the group consisting of: a bond, CO, CONH, CON($C_{1-4}$ alkyl), $SO_2$, and $CHR^f$;

$R^{1a}$ is independently selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

L is independently a hydrocarbon or hydrocarbon-heteroatom linker optionally substituted with 0-1 $R^g$; wherein said hydrocarbon linker has one to four carbon atoms and may be straight or branched, saturated or unsaturated; and said hydrocarbon-heteroatom linker has one to four carbon atoms and one group selected from O, S, —SO—, and —$SO_2$—;

alternatively, L is $X_1-Y-X_2$;

$X_1$ and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-6}$ cycloalkylene, $C_{4-6}$ cycloalkenylene, phenylene, pyridylene, azetidinylene, pyrrolidinylene, piperidinylene, pyrazolylene, thiazolylene, oxadiazolylene, imidazolylene, and benzimidazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy.

In a fourth aspect, the present invention includes a compound of Formula (I), wherein $R^{2d}$ is H and $R^5$ is OH, further characterized by Formula (II):

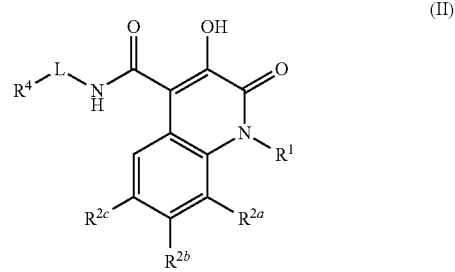

or a stereoisomer, a tautomer, a pharmaceutically acceptable salt, or a solvate thereof, within the scope of any of the above aspects, wherein:

$R^1$ is independently selected from the group consisting of: H, $C_{1-4}$ alkyl substituted with 0-1 $R^a$, —$(CH_2)_{0-1}$—CH$(CH_3)$-(phenyl substituted with 0-2 $R^b$), —$(CH_2)_{0-2}$-(phenyl substituted with 0-3 $R^b$), and —$(CH_2)_{0-2}$-(5- to 6-membered heterocycle comprising: carbon atoms and 1-4 heteroatoms selected from N, $NR^e$, O, and $S(O)_p$); and wherein said heterocycle is substituted with 0-2 $R^c$;

$R^{2a}$, $R^{2b}$, and $R^{2c}$ are, independently at each occurrence, selected from the group consisting of: H, halogen, $CF_3$, $OCF_3$, $OCF_2CHF_2$, $OCH_2CF_3$, $OCF_2CF_3$, $OCH_2CF_2CF_3$, CN, $NH_2$, $NO_2$, $CONH_2$, $C_{1-4}$ alkyl, $C_{1-2}$ alkenyl, $C_{1-4}$ alkoxy, and phenyl substituted with 0-2 $R^c$; and $R^4$ is independently selected from: phenyl, naphthyl, tetrahydronaphthyl, dihydroindenyl, pyrrolidinyl, thienyl, pyrrolyl, pyrazolyl, imidazolyl, 1,2,3-thiadiazolyl, 1,2,4-oxadiazolyl, piperidinyl, piperazinyl, morpholinyl, indolinyl, quinolinyl, and benzimidazolyl; wherein each moiety is substituted with 0-2 $R^d$;

alternatively, $R^4$-L- is

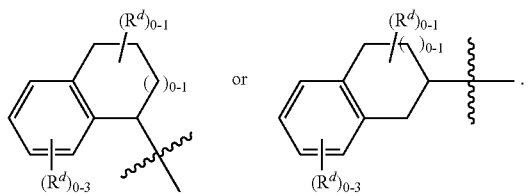

In a fifth aspect, the present invention includes a compound of Formula (II), or a stereoisomer, a tautomer, a pharmaceutically acceptable salt, or a solvate thereof, within the scope of any of the above aspects, wherein:

$R^1$ is independently selected from the group consisting of: H, $C_{1-4}$ alkyl, —$CH_2CO_2(C_{1-4}$ alkyl), phenyl, 4-halo-phenyl, benzyl, 4-$CO_2$H-benzyl, 4-$SO_2(C_{1-4}$ alkyl)-benzyl, 2-($C_{1-4}$ alkoxy)-5-halo-benzyl, 2-halo-phenethyl, 2-OH-phenethyl;

$R^{2a}$, $R^{2b}$, and $R^{2c}$ are, independently at each occurrence, selected from the group consisting of: H, halogen, $CF_3$, $OCF_3$, CN, $NH_2$, $NO_2$, $CONH_2$, $C_{1-4}$ alkyl, $C_{1-2}$ alkenyl, $C_{1-4}$ alkoxy, and phenyl substituted with 0-2 $R^c$;

$R^4$ is independently selected from: phenyl, naphthyl, tetrahydronaphthyl, pyrrolidinyl, thienyl, pyrrolyl, pyrazolyl, imidazolyl, 1,2,3-thiadiazolyl, 1,2,4-oxadiazolyl, tetrazolyl, piperidinyl, piperazinyl, morpholinyl, indolyl, indolinyl, and benzimidazolyl; wherein each moiety is substituted with 0-2 $R^d$;

L is independently a hydrocarbon or hydrocarbon-heteroatom linker optionally substituted with 0-1 $R^g$; wherein said hydrocarbon linker has one to six carbon atoms and may be straight or branched, and saturated or unsaturated; and said hydrocarbon-heteroatom linker has one to six carbon atoms and one group selected from O, —CO—, S, —SO—, —SO_2—, NH, and N($C_{1-4}$ alkyl);

alternatively, L is $X_1$—Y—$X_2$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to four carbon atoms and may be saturated or unsaturated; and said hydrocarbon-heteroatom linker has zero to three carbon atoms and one group selected from O, —CO—, S, —SO—, —SO_2—, NH, and N($C_{1-4}$ alkyl);

$X_2$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to five carbon atoms and may be saturated or unsaturated; and said hydrocarbon-heteroatom linker has zero to four carbon atoms and one group selected from O, —CO—, S, —SO—, —SO_2—, NH, and N($C_{1-4}$ alkyl); and Y is independently selected from the group consisting of: $C_{3-6}$ cycloalkylene, $C_{4-6}$ cycloalkenylene, phenylene, pyridylene, azetidinylene, pyrrolidinylene, piperidinylene, pyrazolylene, thiazolylene, oxadiazolylene, imidazolylene, and benzimidazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy;

alternatively, $R^4$-L- is

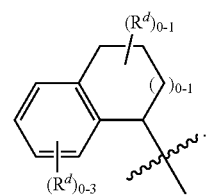

In a sixth aspect, the present invention includes a compound of Formula (II), or a stereoisomer, a tautomer, a pharmaceutically acceptable salt, or a solvate thereof, within the scope of any of the above aspects wherein:

$R^1$ is independently selected from the group consisting of: H, $C_{1-4}$ alkyl, phenyl, 4-halo-phenyl, benzyl, and 2-($C_{1-4}$ alkoxy)-5-halo-benzyl;

$R^{2a}$ is independently selected from the group consisting of: H, halogen, $CF_3$, $OCF_3$, and $C_{1-4}$ alkyl;

$R^{2b}$ is independently selected from the group consisting of: H and halogen;

$R^{2c}$ is independently selected from the group consisting of: H, halogen, $CF_3$, $OCF_3$, $C_{1-4}$ alkyl, $C_{1-4}$ alkoxy, CN, $NH_2$, $NO_2$, $CONH_2$, and 4-halo-Ph; and $R^4$ is independently selected from the group consisting of: phenyl, 2-halo-phenyl, 3-halo-phenyl, 4-halo-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2(C_{1-4}$ alkyl)-phenyl, 4-$CO_2(C_{1-4}$ alkyl)-phenyl, 2-$NO_2$-phenyl, 3-$NO_2$-phenyl, 4-$NO_2$-phenyl, 2-($C_{1-4}$ alkyl)-6-($C_{1-4}$ alkyl)-phenyl, 2-halo-3-halo-phenyl, 2-halo-4-halo-phenyl, 3-halo-4-halo-phenyl, 2-halo-6-halo-phenyl, 2-$CF_3$-4-halo-phenyl, 1-naphthyl, 2-naphthyl, 1-pyrrolidinyl, 2-thienyl, 1-pyrrolyl, 1-pyrazolyl, 1,2,3-thiadiazol-4-yl, tetrazol-1-yl, 5-($C_{1-4}$ alkyl)-1,2,4-oxadiazol-3-yl, 1-piperidinyl, 3-($C_{1-4}$ alkyl)-piperidin-1-yl, 4-($C_{1-4}$ alkyl)-piperidin-1-yl, 4-OH-piperidin-1-yl, 4-phenyl-piperidin-1-yl, 4-phenyl-4-OH-piperidin-1-yl, 4-$CO_2(C_{1-4}$ alkyl)-piperazin-1-yl, 4-Cbz-piperazin-1-yl, 4-($C_{1-4}$ alkyl)-piperazin-1-yl, 4-$CH_2CH_2$OH-piperazin-1-yl, 4-morpholinyl, 1H-indol-4-yl,

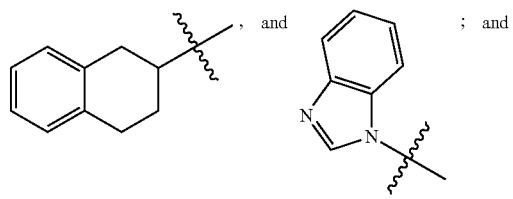 [SMILES: *C1CCc2ccccc2C1 ; *n1cnc2ccccc21]

L is independently selected from the group consisting of: $C_{1-4}$ alkylene, —O—$C_{2-4}$ alkylene-, —S—$C_{2-4}$ alkylene-, —$C_{0-2}$ alkylene-(1,2-phenylene)-$C_{0-2}$ alkylene-, —$C_{0-2}$ alkylene-(1,3-phenylene)-C$_{0-2}$ alkylene-, —C$_{0-2}$ alkylene-(1,4-phenylene)-C$_{0-2}$ alkylene-, —NH-(1,3-phenylene)-C$_{0-2}$ alkylene-, —O-(1,4-phenylene)-C$_{0-2}$ alkylene-, -(1,2-phenylene)-O—C$_{0-3}$ alkylene-, -(1,3-phenylene)-O—C$_{0-3}$ alkylene-, -(1,4-phenylene)-O—C$_{0-3}$ alkylene-, —O-(1,4-phenylene)-O—C$_{0-3}$ alkylene-, —SO$_2$-(1,4-phenylene)-C$_{0-2}$ alkylene-,

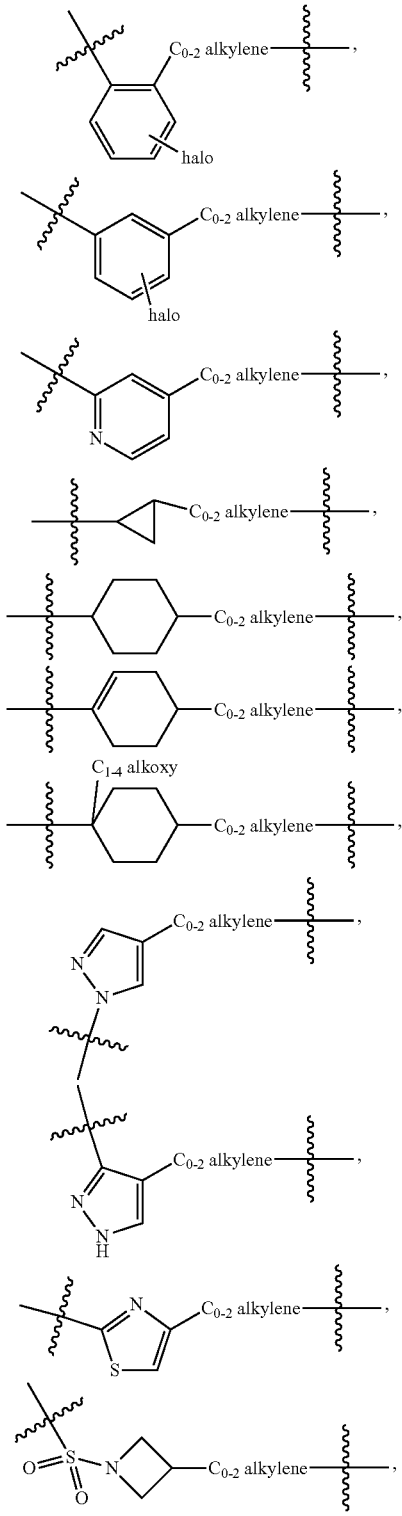

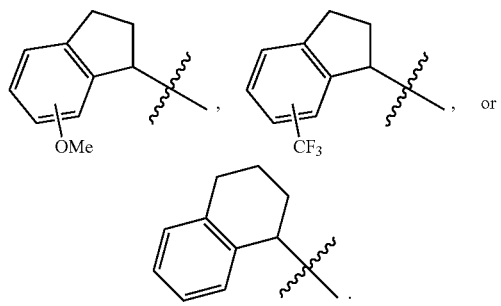

wherein each said alkylene may be straight or branched; alternatively, R$^4$-L- is

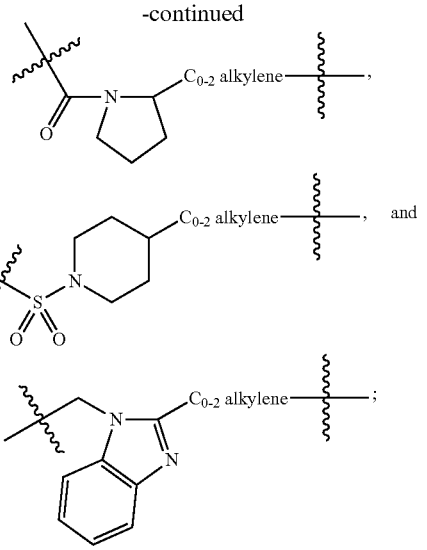

In a seventh aspect, the present invention includes a compound of Formula (II), or a stereoisomer, a tautomer, a pharmaceutically acceptable salt, or a solvate thereof, within the scope of any of the above aspects wherein:

R$^1$ is independently selected from the group consisting of: H, methyl, isopropyl, isobutyl, phenyl, 4-Br-phenyl, benzyl, and 2-OCH$_3$-5-Cl-benzyl;

R$^{2a}$ is independently selected from the group consisting of: H, F, CF$_3$, OCF$_3$, and methyl;

R$^{2b}$ is independently selected from the group consisting of: H and Cl;

R$^{2c}$ is independently selected from the group consisting of: H, F, Cl, Br, I, CF$_3$, OCF$_3$, methyl, methoxy, CN, NH$_2$, NO$_2$, CONH$_2$, and 4-F-Ph;

R$^4$ is independently selected from the group consisting of: phenyl, 2-F-phenyl, 3-F-phenyl, 4-F-phenyl, 2-Cl-phenyl, 3-Cl-phenyl, 4-Cl-phenyl, 3-methyl-phenyl, 4-methyl-phenyl, 2-methoxy-phenyl, 3-methoxy-phenyl, 4-methoxy-phenyl, 2-CF$_3$-phenyl, 3-CF$_3$-phenyl, 4-CF$_3$-phenyl, 3-OCF$_3$-phenyl, 4-OCF$_3$-phenyl, 3-CO$_2$Me-phenyl, 4-CO$_2$Me-phenyl, 2-NO$_2$-phenyl, 3-NO$_2$-phenyl, 4-NO$_2$-phenyl, 2,6-dimethyl-phenyl, 2,3-dichloro-phenyl, 2,4-dichloro-phenyl, 3,4-dichloro-phenyl, 2,6-dichloro-phenyl, 2-CF$_3$-4-F-phenyl, 1-naphthyl, 2-naphthyl, 1-pyrrolidinyl, 2-thienyl, 1-pyrrolyl, 1-pyrazolyl, 1,2,3-thiadiazol-4-yl, 5-methyl-1,2,4-oxadiazol-3-yl, 1-piperidinyl, 4-phenyl-piperidin-1-yl, 4-phenyl-4-OH-piperidin-1-yl, 4-methyl-piperidin-1-yl, 4-Boc-piperazin-1-yl, 4-Cbz-1-piperazinyl, 4-CH$_2$CH$_2$OH-piperazin-1-yl, 4-morpholinyl,

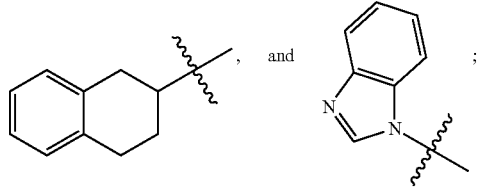 [SMILES: *C1CCc2ccccc2C1 ; *n1cnc2ccccc21], and 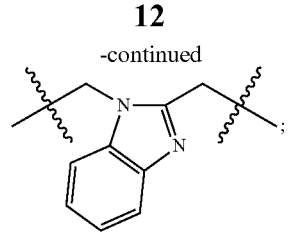

and

L is independently selected from the group consisting of: —CH$_2$—, —CH(CH$_3$)—, —CH(CH$_2$CH$_3$)—, —(CH$_2$)$_2$—, —(CH$_2$)$_3$—, —(CH$_2$)$_2$CH(CH$_3$)—, —OCH(CH$_3$)CH$_2$—, —OCH$_2$CH(CH$_3$)—, —O—(CH$_2$)$_2$CH(CH$_3$)—, —O—(CH$_2$)$_2$—, —O(CH$_2$)$_3$—, —O(CH$_2$)$_4$—, —S(CH$_2$)$_3$—, -(1,2-phenylene)-CH$_2$—, -(1,3-phenylene)-CH$_2$—, -(1,4-phenylene)-CH$_2$—, -(1,4-phenylene)-(CH$_2$)$_2$—, —CH$_2$-(1,3-phenylene)-CH$_2$—, —CH$_2$-(1,4-phenylene)-CH$_2$—, -(1,3-phenylene)-CH(CH$_3$)—, —NH-(1,3-phenylene)-CH(CH$_3$)—, —O-(1,4-phenylene)-CH$_2$—, -(1,2-phenylene)-O(CH$_2$)$_3$—, -(1,3-phenylene)-O(CH$_2$)$_3$—, -(1,4-phenylene)-O(CH$_2$)$_3$—, —O-(1,4-phenylene)-O(CH$_2$)$_3$—, —(CH$_2$)$_2$O-(1,3-phenylene)-CH$_2$—, —SO$_2$-(1,4-phenylene)-CH$_2$—

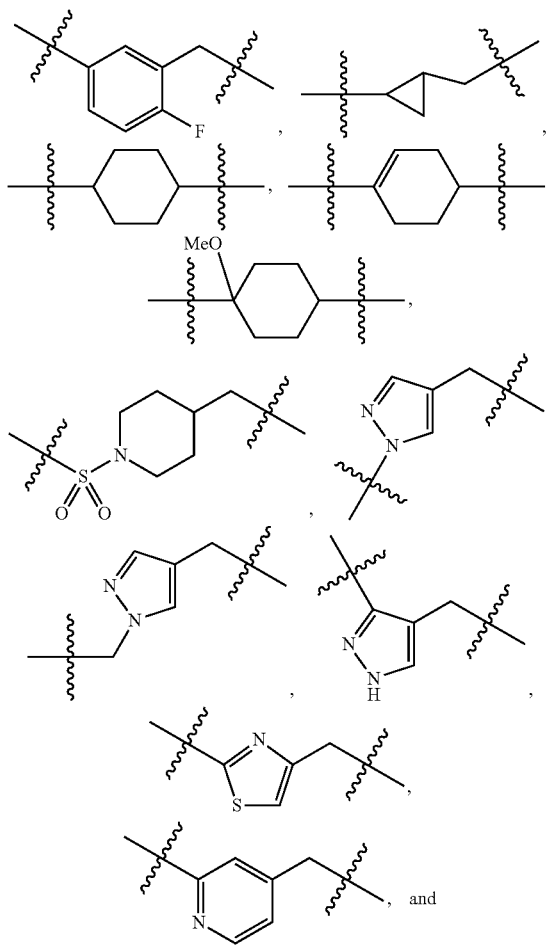

-continued

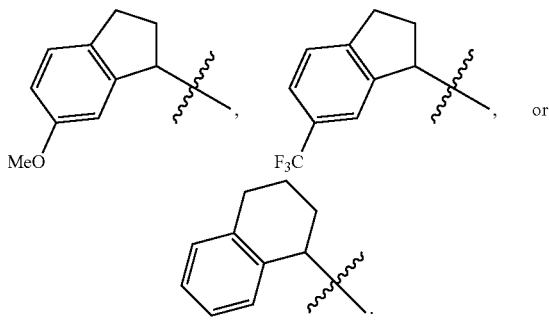

alternatively, R$^4$-L- is

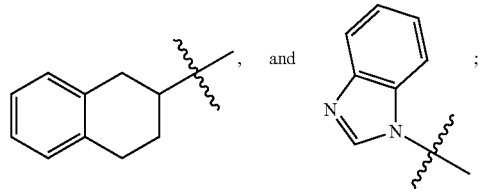 [SMILES: *C1CCc2ccccc2C1 ; *n1cnc2ccccc21]

In an eighth aspect, the present invention includes a compound of Formula (II), or a stereoisomer, a tautomer, a pharmaceutically acceptable salt, or a solvate thereof, within the scope of any of the above aspects wherein:

R$^1$ is independently selected from the group consisting of: H, methyl, isopropyl, isobutyl, phenyl, 4-Br-phenyl, benzyl, and 2-OCH$_3$-5-Cl-benzyl;

R$^{2a}$ is independently selected from the group consisting of: H, F, OCF$_3$, and methyl;

R$^{2b}$ is independently selected from the group consisting of: H and Cl;

R$^{2c}$ is independently selected from the group consisting of: H, F, Cl, Br, I, CF$_3$, OCF$_3$, methyl, methoxy, CN, NH$_2$, and NO$_2$;

R$^4$ is independently selected from the group consisting of: phenyl, 2-F-phenyl, 3-F-phenyl, 4-F-phenyl, 2-Cl-phenyl, 4-Cl-phenyl, 3-methyl-phenyl, 4-methyl-phenyl, 2-methoxy-phenyl, 3-methoxy-phenyl, 4-methoxy-phenyl, 2-CF$_3$-phenyl, 3-CF$_3$-phenyl, 4-CF$_3$-phenyl, 3-OCF$_3$-phenyl, 4-OCF$_3$-phenyl, 3-CO$_2$Me-phenyl, 4-CO$_2$Me-phenyl, 2-NO$_2$-phenyl, 3-NO$_2$-phenyl, 4-NO$_2$-phenyl, 2,6-dimethyl-phenyl, 2,3-dichloro-phenyl, 2,4-dichloro-phenyl, 3,4-dichloro-phenyl, 2,6-dichloro-phenyl, 1-naphthyl, 1-pyrrolyl, 1-piperidinyl, 4-phenyl-4-OH-piperidin-1-yl, 4-Boc-piperazin-1-yl, 4-Cbz-1-piperazinyl,

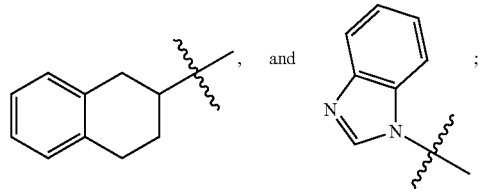 [SMILES: *C1CCc2ccccc2C1 ; *n1cnc2ccccc21]

and

L is independently selected from the group consisting of: —CH$_2$—, —CH(CH$_2$CH$_3$)—, —(CH$_2$)$_2$—, —(CH$_2$)$_3$—, —(CH$_2$)$_2$CH(CH$_3$)—, —OCH$_2$CH(CH$_3$)—, —O(CH$_2$)$_2$CH(CH$_3$)—, —O(CH$_2$)$_3$—, —O(CH$_2$)$_4$—, —S(CH$_2$)$_3$—, -(1,2- phenylene)-CH$_2$—, -(1,3-phenylene)-CH$_2$—, -(1,4-phenylene)-CH$_2$—, -(1,3-phenylene)-CH(CH$_3$)—, —O-(1,4-phenylene)-CH$_2$—, -(1,2-phenylene)-O(CH$_2$)$_3$—, -(1,3-phenylene)-O(CH$_2$)$_3$—, -(1,4-phenylene)-O(CH$_2$)$_3$—, —O-(1,4-phenylene)-O(CH$_2$)$_3$—,

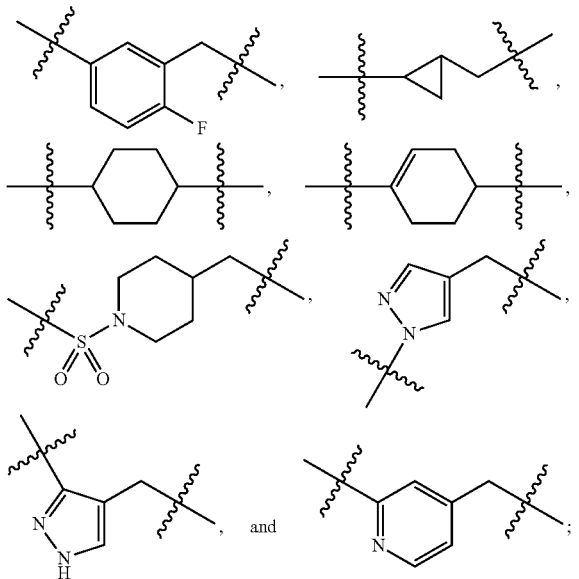

alternatively, R$^4$-L- is

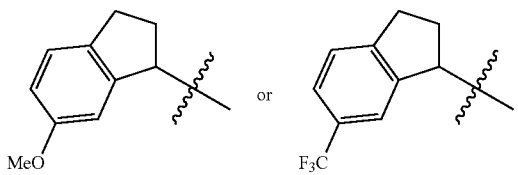

In a ninth aspect, the present invention includes a compound of Formula (II), or a stereoisomer, a tautomer, a pharmaceutically acceptable salt, or a solvate thereof, within the scope of any of the above aspects wherein:

R$^4$ is independently selected from the group consisting of: phenyl, 2-F-phenyl, 3-F-phenyl, 4-F-phenyl, 2-Cl-phenyl, 3-Cl-phenyl, 4-Cl-phenyl, 3-methyl-phenyl, 4-methyl-phenyl, 2-methoxy-phenyl, 3-methoxy-phenyl, 4-methoxy-phenyl, 2-CF$_3$-phenyl, 3-CF$_3$-phenyl, 4-CF$_3$-phenyl, 3-OCF$_3$-phenyl, 4-OCF$_3$-phenyl, 3-CO$_2$Me-phenyl, 4-CO$_2$Me-phenyl, 2-NO$_2$-phenyl, 3-NO$_2$-phenyl, 4-NO$_2$-phenyl, 2,6-dimethyl-phenyl, 2,3-dichloro-phenyl, 2,4-dichloro-phenyl, 3,4-dichloro-phenyl, 2,6-dichloro-phenyl, 2-CF$_3$-4-F-phenyl, 1-naphthyl, 2-naphthyl, and

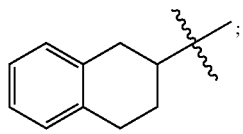

and

L is independently selected from the group consisting of: —CH$_2$—, —CH(CH$_3$)—, —CH(CH$_2$CH$_3$)—, —(CH$_2$)$_2$—, —(CH$_2$)$_3$—, —(CH$_2$)$_2$CH(CH$_3$)—, —OCH(CH$_3$)CH$_2$—, —OCH$_2$CH(CH$_3$)—, —O(CH$_2$)$_2$CH(CH$_3$)—, —O(CH$_2$)$_2$—, —O(CH$_2$)$_3$—, —O(CH$_2$)$_4$—, and —S(CH$_2$)$_3$—.

In a tenth aspect, the present invention includes a compound of Formula (II), or a stereoisomer, a tautomer, a pharmaceutically acceptable salt, or a solvate thereof, within the scope of any of the above aspects wherein:

R$^4$ is independently selected from the group consisting of: phenyl, 4-F-phenyl, 4-Cl-phenyl, 4-methyl-phenyl, 2-CF$_3$-phenyl, 4-CF$_3$-phenyl, 3,4-dichloro-phenyl, 1-pyrrolidinyl, 2-thienyl, 1-pyrrolyl, 1-pyrazolyl, 1,2,3-thiadiazol-4-yl, 5-methyl-1,2,4-oxadiazol-3-yl, 1-piperidinyl, 4-phenyl-piperidin-1-yl, 4-phenyl-4-OH-piperidin-1-yl, 4-methyl-piperidin-1-yl, 4-Boc-piperazin-1-yl, 4-Cbz-1-piperazinyl, 4-CH$_2$CH$_2$OH-piperazin-1-yl, 4-morpholinyl, and

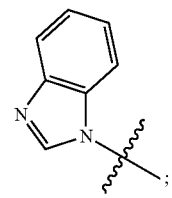 [SMILES: *n1cnc2ccccc21]

and

L is independently selected from the group consisting of: -(1,2-phenylene)-CH$_2$—, -(1,3-phenylene)-CH$_2$—, -(1,4-phenylene)-CH$_2$—, -(1,4-phenylene)-(CH$_2$)$_2$—, —CH$_2$-(1,3-phenylene)-CH$_2$—, —CH$_2$-(1,4-phenylene)-CH$_2$—, -(1,3-phenylene)-CH(CH$_3$)—, —NH-(1,3-phenylene)-CH(CH$_3$)—, —O-(1,4-phenylene)-CH$_2$—, -(1,2-phenylene)-O(CH$_2$)$_3$—, -(1,3-phenylene)-O(CH$_2$)$_3$—, -(1,4-phenylene)-O(CH$_2$)$_3$—, —O-(1,4-phenylene)-O(CH$_2$)$_3$—, —(CH$_2$)$_2$O-(1,3-phenylene)-CH$_2$—, —SO$_2$-(1,4-phenylene)-CH$_2$—,

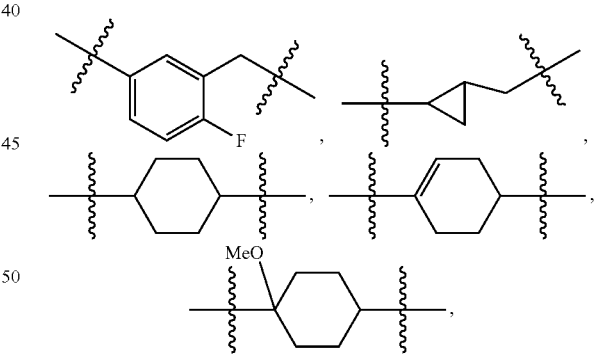

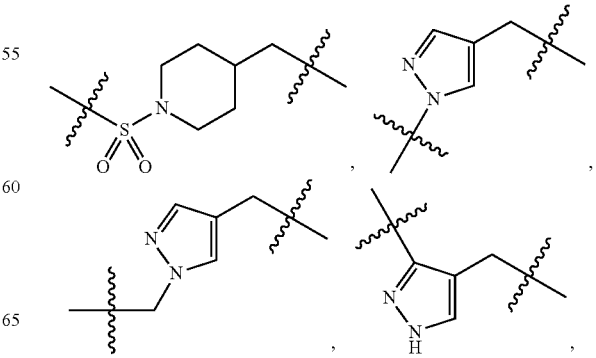

-continued

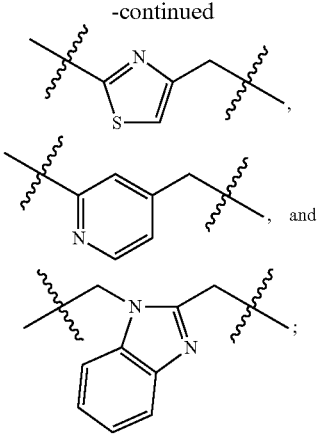

alternatively, $R^4$-L- is

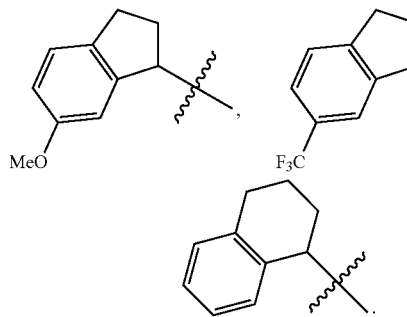

In an eleventh, the present invention includes a compound of Formula (II), or a stereoisomer, a tautomer, a pharmaceutically acceptable salt, or a solvate thereof, within the scope of any of the above aspects wherein:

$R^4$ is independently selected from the group consisting of: phenyl, 2-F-phenyl, 3-F-phenyl, 4-F-phenyl, 2-Cl-phenyl, 4-Cl-phenyl, 3-methyl-phenyl, 4-methyl-phenyl, 2-methoxy-phenyl, 3-methoxy-phenyl, 4-methoxy-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2Me$-phenyl, 4-$CO_2Me$-phenyl, 2-$NO_2$-phenyl, 3-$NO_2$-phenyl, 4-$NO_2$-phenyl, 2,6-dimethyl-phenyl, 2,3-dichloro-phenyl, 2,4-dichloro-phenyl, 3,4-dichloro-phenyl, 2,6-dichloro-phenyl, 1-naphthyl, and

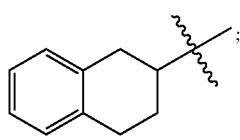 [SMILES: *C1CCc2ccccc2C1]

and

L is independently selected from the group consisting of: —$CH_2$—, —$CH(CH_2CH_3)$—, —$(CH_2)_2$—, —$(CH_2)_3$—, —$(CH_2)_2CH(CH_3)$—, —$OCH_2CH(CH_3)$—, —$O(CH_2)_2CH(CH_3)$—, —$O(CH_2)_3$—, —$O(CH_2)_4$—, and —$S(CH_2)_3$—.

In a twelfth aspect, the present invention includes a compound of Formula (II), or a stereoisomer, a tautomer, a pharmaceutically acceptable salt, or a solvate thereof, within the scope of any of the above aspects wherein:

$R^4$ is independently selected from the group consisting of: phenyl, 4-F-phenyl, 4-methyl-phenyl, 3,4-dichloro-phenyl, 1-pyrrolyl, 1-piperidinyl, 4-phenyl-4-OH-piperidin-1-yl, 4-Boc-piperazin-1-yl, 4-Cbz-1-piperazinyl, and

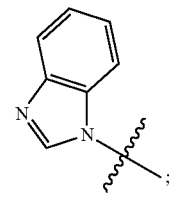 [SMILES: *n1cnc2ccccc21]

and

L is independently selected from the group consisting of: -(1,2-phenylene)-$CH_2$—, -(1,3-phenylene)-$CH_2$—, -(1,4-phenylene)-$CH_2$—, -(1,3-phenylene)-$CH(CH_3)$—, —O-(1,4-phenylene)-$CH_2$—, -(1,2-phenylene)-$O(CH_2)_3$—, -(1,3-phenylene)-$O(CH_2)_3$—, -(1,4-phenylene)-$O(CH_2)_3$—, —O-(1,4-phenylene)-$O(CH_2)_3$—,

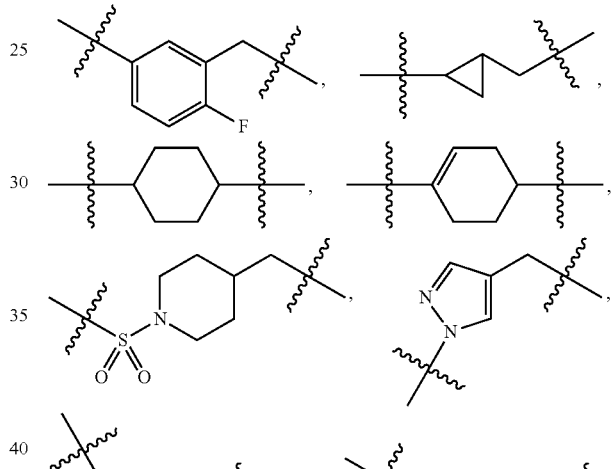

alternatively, $R^4$-L- is

In a thirteenth aspect, the present invention provides a compound selected from the exemplified examples or a stereoisomer, a tautomer, a pharmaceutically acceptable salt, or a solvate thereof.

In another aspect, the present invention provides a compound selected from any subset list of the exemplified examples or any one of the exemplified examples or a stereoisomer, a tautomer, a pharmaceutically acceptable salt, or a solvate thereof, within the scope of the thirteenth aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., Hawley's *Condensed Chemical Dictionary*, 13th Edition, J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH), as shown in the following equation:

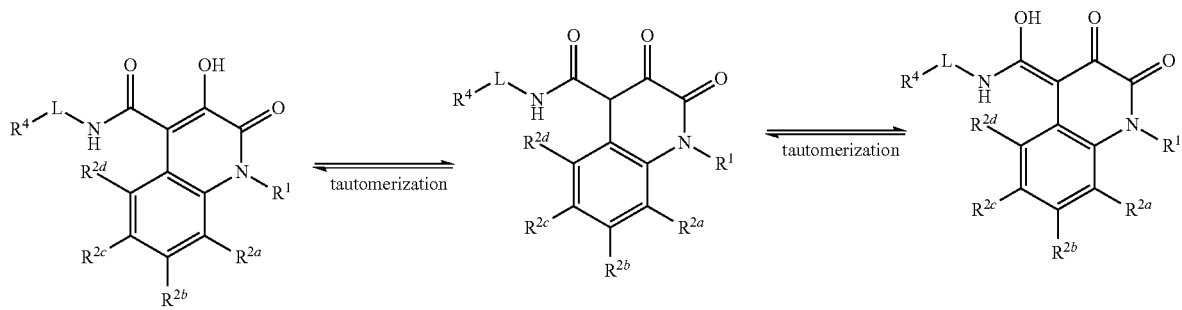

Likewise, an imine (—CH—C═NHR) group in a molecule may tautomerize to its enamine form (—C═C—NHR), as shown in the following equation:

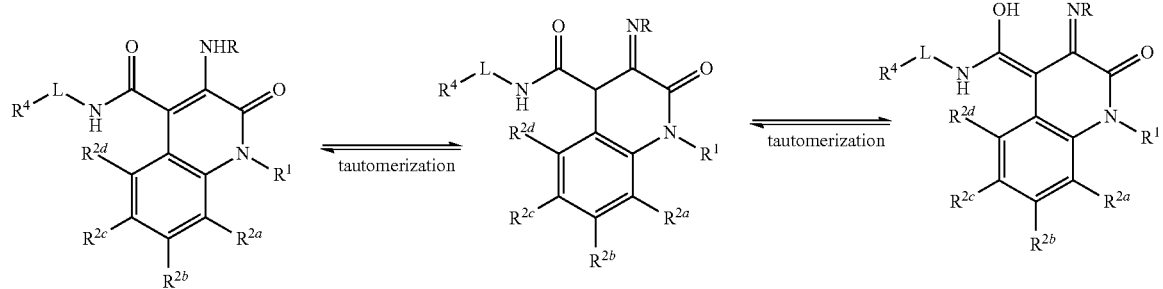

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I), Formula (II), Formula (III), or Formula (IV) may have prodrug forms. Any compound that will be converted in vivo to provide the bioactive agent (i.e., a compound of Formula (I), Formula (II), Formula (III), or Formula (IV)) is a prodrug within the scope and spirit of the invention. Various forms of prodrugs are well known in the art. For examples of such prodrug derivatives, see:

a) *Design of Prodrugs,* Bundgaard, H., ed., Elsevier (1985), and *Methods in Enzymology,* 112:309-396, Widder, K. et al., eds., Academic Press (1985);

b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
AlCl$_3$ aluminum chloride
BBr$_3$ boron tribromide
BCl$_3$ boron trichloride
BOP reagent benzotriazol-1-yloxytris(dimethylamino)phosphonium hexafluorophosphate
Cbz carbobenzyloxy
CH$_2$Cl$_2$ dichloromethane
CH$_3$CN or ACN acetonitrile
CDCl$_3$ deutero-chloroform
CDCl$_3$ chloroform
mCPBA or m-CPBA meta-chloroperbenzoic acid
Cs$_2$CO$_3$ cesium carbonate
Cu(OAc)$_2$ copper (II) acetate
DCE 1,2 dichloroethane
DCM dichloromethane
DEA diethylamine
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimethylaminopropyl)-N'-ethylcarbodiimide
EDTA ethylenediaminetetraacetic acid
Et$_3$N or TEA triethylamine
EtOAc ethyl acetate
Et$_2$O diethyl ether
EtOH ethanol
HCl hydrochloric acid
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS polystyrene
PyBOP (benzotriazol-1-yloxy)tripyrrolidinophosphonium hexafluorophosphate
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons (1991)).

Schemes 1-11 describe synthetic routes for making compounds of the present invention. Schemes 1-3 describe preparations of compounds of the present invention from key intermediates 2, 4 or 5. Schemes 4-5 illustrate several preparations for the acid or ester intermediate 5 from commercially available starting materials. Schemes 6-9 describe preparations of amine intermediates from commercially available starting materials. Scheme 10 exemplifies preparations of compounds of the present invention wherein $R^5$ is not an OH group and Scheme 11 shows the exemplified synthesis of N-1 $R^1$ substituted compounds.

Scheme 1 describes a preparation of compounds of Formula (I) of the present invention from the key intermediate 2. The amine intermediates 3 ($R^4$-L-$NH_2$) or their HCl or TFA salts are either commercially available or can be readily prepared from commercially available materials by methods known to one skilled in the art of organic synthesis. Reaction of amine 3 with acid 2 can occur under standard amide coupling conditions at temperatures between 0° C. and 100° C. in a variety of solvents such as DMF or dichloromethane. The protocols include, but are not limited to, formation of the acid chloride of intermediate 2 using either oxalyl chloride and catalytic DMF in the presence of a suitable solvent such as dichloromethane or thionyl chloride, followed by addition of amine 3 in the presence of a base such as TEA, DIPEA or N-methylmorpholine; or formation of the active ester of intermediate 2 using EDC, HOBt, PyBop and a base, such as TEA, DIPEA or N-methylmorpholine, in the presence of amine 3.

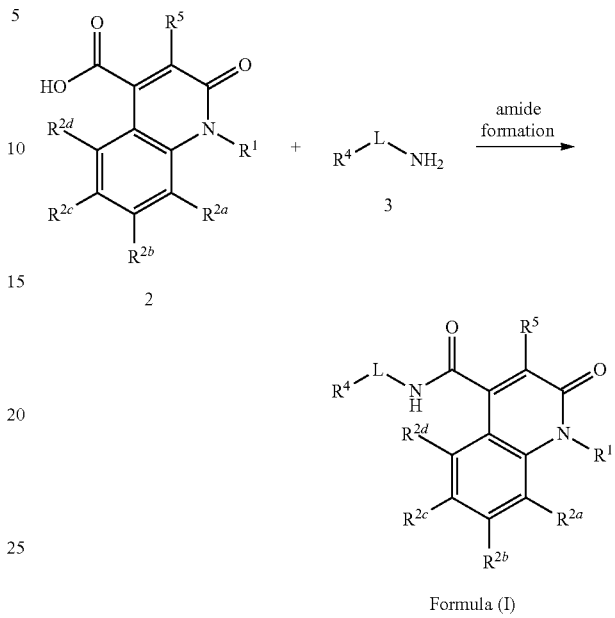

Scheme 1

Formula (I)

Alternatively, compounds of Formula (I) of the present invention can be prepared by displacement of the methyl ester 4 with the amine 3 in polar solvents such as ethanol, DMF, or neat at elevated temperatures or under microwave irradiation as shown in Scheme 2.

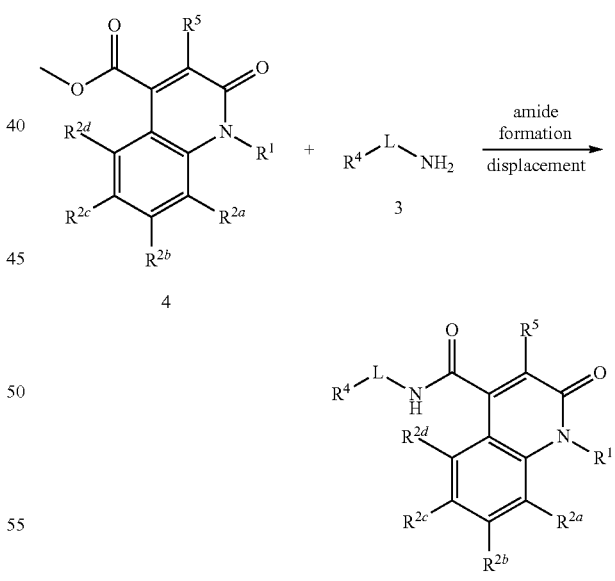

Scheme 2

Formula (I)

Compounds of Formula (I) wherein $R^5$=OH can be made by the general methods described in Schemes 1 and 2. Alternatively, the hydroxyl group in acid 2 can be protected as shown in Intermediate 5 (Scheme 3), wherein the protecting group can be methyl, benzyl, allyl, or silyl-based groups. Amide formation between the acid 5 and the amine 3, followed by deprotection to free the hydroxyl group in Intermediate 6 can afford the compounds of Formula (I) (wherein $R^5$=OH). When the protecting group on the hydroxyl group is methyl, ethyl, isopropyl, or benzyl, deprotection can occur with $BBr_3$, $BCl_3$, $BBr_3.SMe$, $BCl_3.SMe$ $AlCl_3$, or $BCl_3$/TBAI at temperatures between –78° C. and refluxing in a solvent such as $CH_2Cl_2$. When heating is required, the reaction can also occur under microwave irradiation to shorten the reaction time. When the protecting group on the hydroxyl group is a benzyl group, debenzylation can also occur by hydrogenation (such as Pd/C, $H_2$) or by using $AlCl_3$ in $CH_2Cl_2$ in a variety of solvents such as methanol or EtOAc.

or benzyl halide in the presence of an inorganic or organic base (such as $K_2CO_3$, $Cs_2CO_3$, $Et_3N$). Alternatively, isatin 7 can be N-arylated using Ullmann-Goldberg reaction (CuI, base heating), or Buchwald modified Ullman reaction (CuI, ligand, base, heating) or Pd C—N cross-coupling reaction ($Pd(OAc)_2$, or other Pd(0) catalysts, base, ligand, heating) with aryl halides or copper-mediated cross-coupling reaction ($Cu(OAc)_2$, base (such as $Et_3N$, pyridine) with aryl boronic acids. Treatment of the corresponding N—$R^1$ substituted isatin derivative 8 with alkyl diazoacetate in the presence of either a Lewis acid such as zinc chloride or a base such as trimethylamine or diethylamine in solvents such as THF, $Et_2O$, DMF, EtOH or MeOH, followed by ring expansion under acidic conditions, such as aq. HCl gave the 3-hydroxyquinoline ester 5. Alternatively, the alkyl 2-(2-tosylhydrazono)acetate 11 can be obtained from condensation of the aldehyde 9 with the 4-methylbenzene-sulfonohydrazide 10. Treatment of isatin 7 with 11 in the presence of NaOMe in MeOH or NaOEt in EtOH can also provide the ester Intermediate 5.

Scheme 3

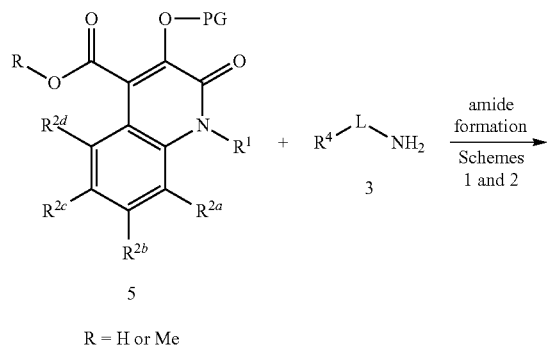

Scheme 4

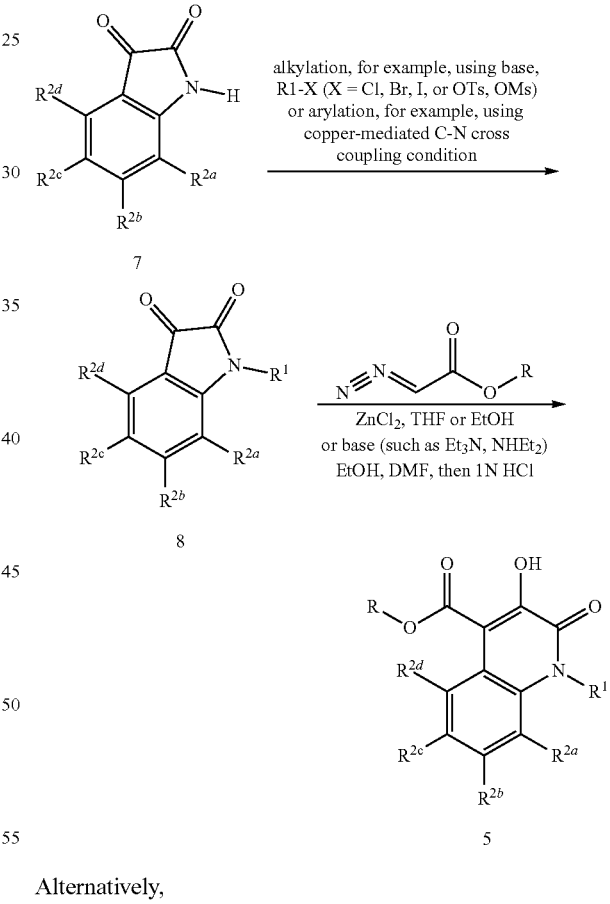

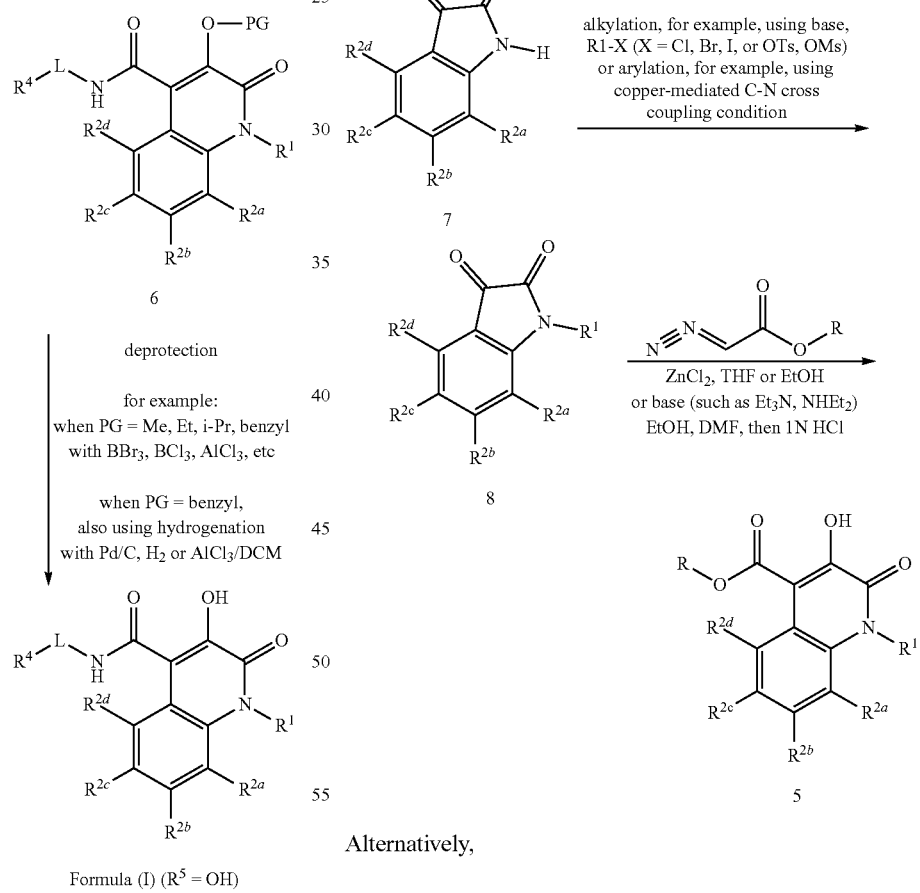

Scheme 4 describes the preparation of 3-hydroxy quinolinone ester Intermediate 5 by ring expansion of the isatin derivative 7. N-1 substituted isatins 8 are commercially available or can be readily prepared from commercially available materials by methods known to one skilled in the art of organic synthesis. Substitution of the NH group in 7 can be performed via either alkylation or C—N cross coupling reactions. For instance, isatin 7 can be alkylated with alkyl halide Alternatively,

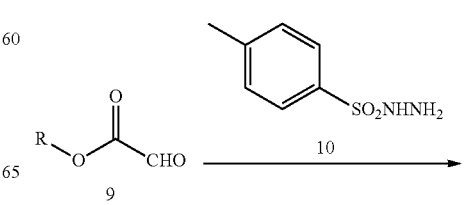

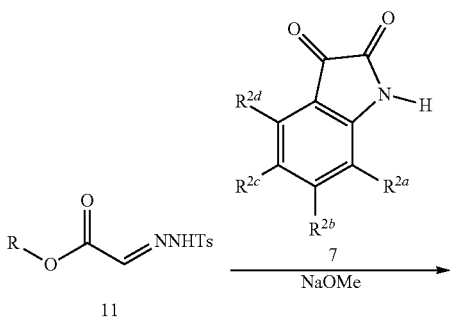

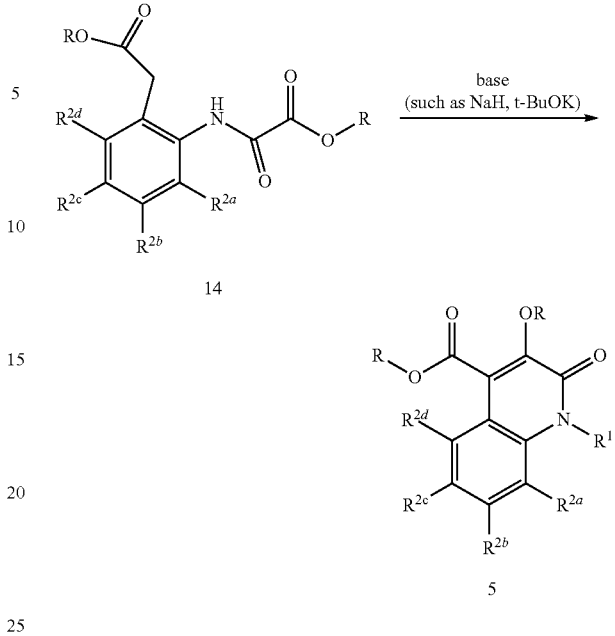

Alternatively, the ester Intermediate 5 can be prepared from commercially available nitro intermediates 12 (Scheme 5). Non-commercially available nitro intermediates can be prepared from known methods by a person skilled in the art of organic synthesis. The ester 13 can be prepared from the nitro Intermediate 12 with electrophiles such as $ClCH_2COOR$ or $CH(COOR)_2$ in the presence of a base such as NaH or t-BuOK via vicarious nucleophilic aromatic substitution reaction (Makosza, *Synthesis*, 103 (1991)). Reduction of the $NO_2$ group in 13 followed by addition of ClCOCOOR in the presence of a base such as $Et_3N$ can afford the oxalamide Intermediate 14, which can be converted to quinolinone Intermediate 5 with a base such as t-BuOK or NaH in solvent such as THF or DMF.

Scheme 5a illustrates examples of amine intermediates $NH_2$-L-$R^4$ (compound 3) that can be used to prepare compounds of the present invention. These intermediates are either commercially available or can be prepared using methods known to those skilled in the art of organic synthesis.

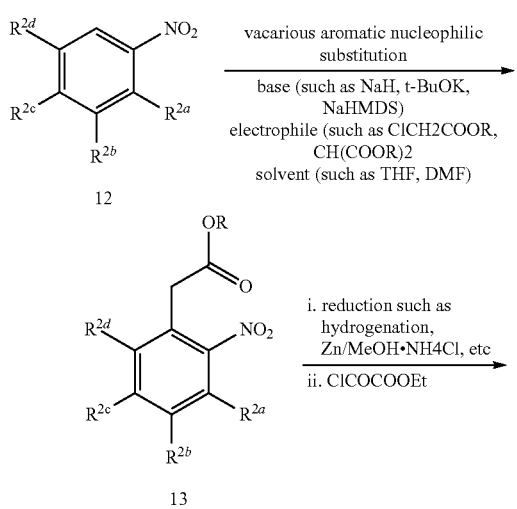

Scheme 5

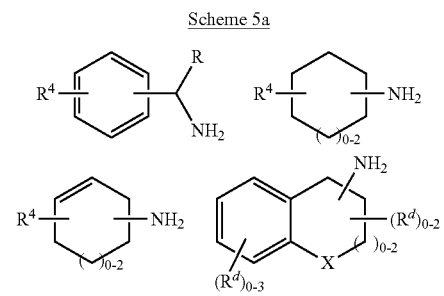

Scheme 5a $R = H, C_{1-3}$ alkyl, or $C_{2-3}$ alkenyl

Scheme 6 outlines one possible preparation of amine intermediates 15, wherein L is a cycloalkyl ring. Reductive amination of the cyclic ketone 16 with diphenylmethanamine followed by separation of the cis- and trans-isomers using silica gel chromatography and then hydrogenation provided the desired cis- or trans-amines 15. Alternatively, the amine 15 can be obtained from reduction of the oxime Intermediate 17. Alternatively, the carbonyl in ketone 16 can be reduced to OH followed by activation and displacement with $NaN_3$ and reduction of the corresponding azide 19. The cyclohexanone starting material 16 is either commercially available or can be readily prepared from commercially available materials by methods known to one skilled in the art of organic synthesis. For examples in Scheme 7, transformation of ketal 20 to vinyl OTf followed by C—C formation of $R^4$—$B(OH)_2$ with the vinyl triflate can afford the corresponding vinyl Intermediate 21. Hydrogenation of 21 followed by deprotection of the ketal group under acidic condition can give the desired ketone 16. Alternatively, treatment of the ketal Intermediate 20 with $R^4$—Li (generated by nBuLi with bromo or iodo $R^4$ species) can give the corresponding alcohol 22, which can be eliminated to give the vinyl intermediate. Alternatively, the alcohol can be directly reduced with triethylsilane followed by deprotection of the ketal group of Intermediate 23 under acidic condition can provide the desired ketone Intermediate 16 (Scheme 7).

-continued

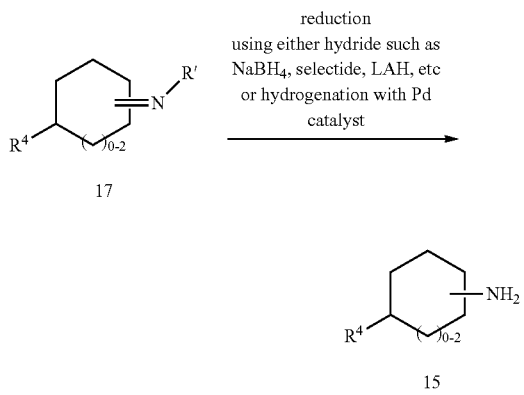

Scheme 6

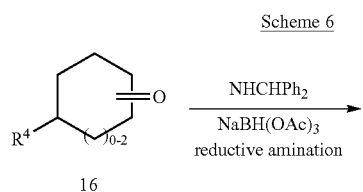

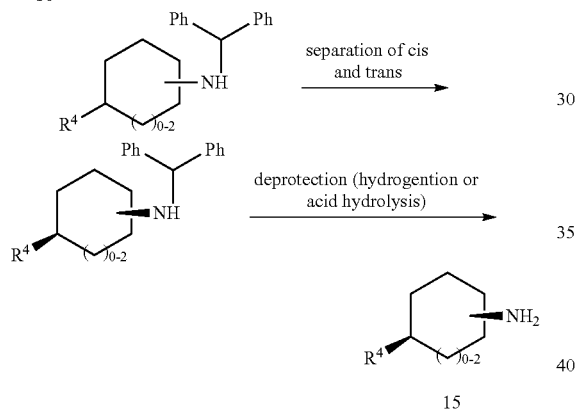

Alternatively,

Scheme 7

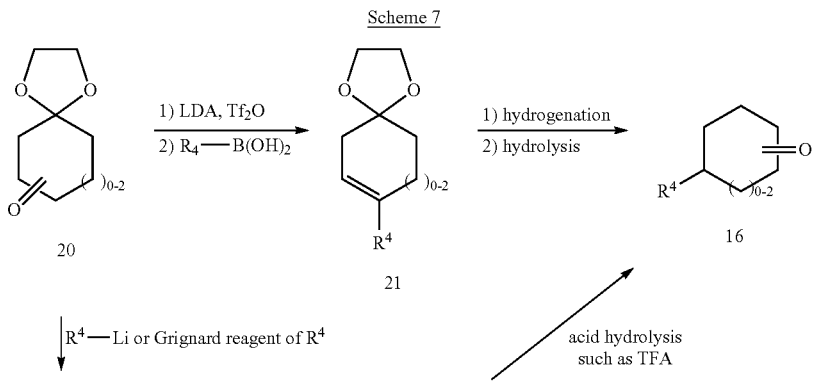

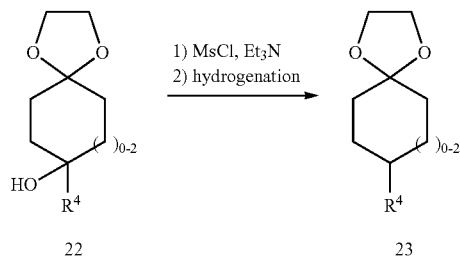

Scheme 8 illustrates bicyclic amines 24 ($R^4$-L-$NH_2$) wherein $R^4$-L is an indane or a tetralin or a 6,7,8,9-tetrahydro-5H-benzo[7]annulene ring. The ketone starting material 25 is either commercially available or can be readily prepared from commercially available materials by methods known to one skilled in the art of organic synthesis. For example, the ketone 25 can be prepared by Friedel-Crafts reaction of acid 26 or by intramolecular cyclization of halide 27 using nBuLi. The desired diastereomers can be obtained by using Ellman's t-butylsulfinamide methodology (Ellman, J. A., *J. Org. Chem.*, 72:626-629 (2007)), reduction of sulfinamide 28 with either $NaBH_4$ or L-selectride at low temperature (for examples, −40 to −50° C.) in THF to give the diastereomer 29 after silica gel column chromatography. Intermediate 29 was hydrolyzed to give the desired enantiopure amine 24.

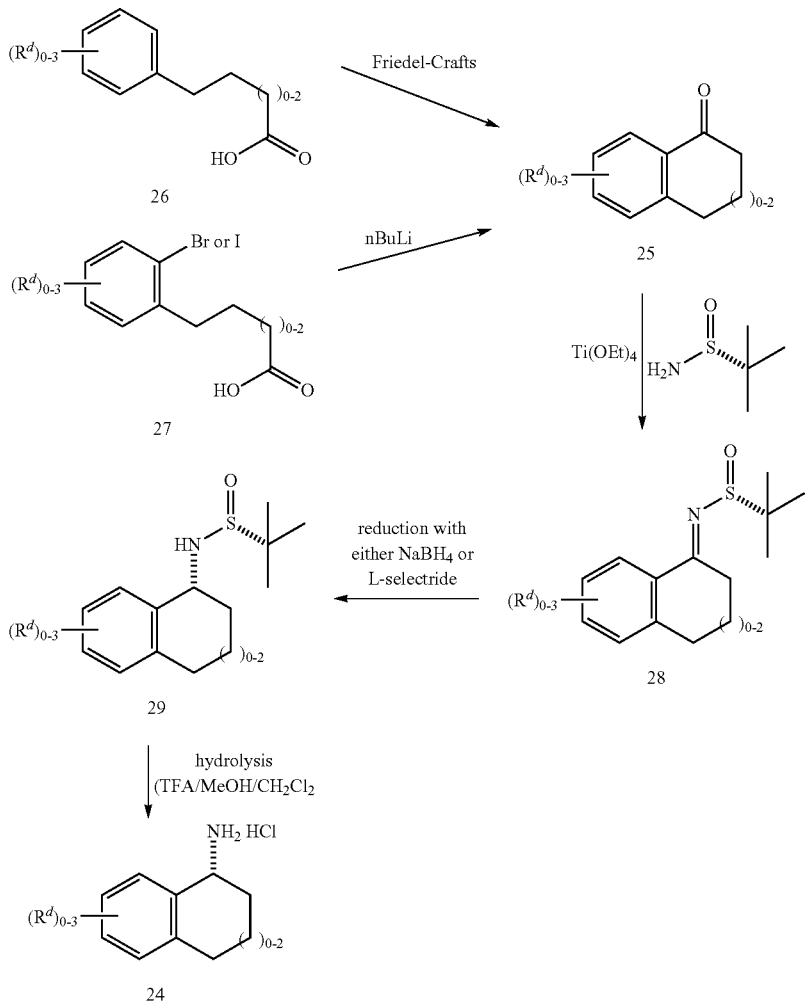

Scheme 9 exemplifies the synthesis of alpha-substituted $C_{2-5}$ alkyl amines 30 (R4-L-NH$_2$) wherein L is an alpha substituted $C_{2-5}$ alkyl group. Compound 30 is either commercially available or can be readily prepared from commercially available materials by methods described in Scheme 9. Ketone 33 is either commercially available or can be readily prepared from commercially available materials by methods described in Scheme 9. For example, Heck reaction of the corresponding aryl halide (bromide or iodide) 31 with the alcohol 32 can give the corresponding aldehyde 34 or ketone 33. The enantiopure amine 30 can be made from the ketone Intermediate 35 by reduction followed by deprotection using methods illustrated in Scheme 8. Treatment of aldehyde 36 with Grignard reagent can give the desired diastereomer sulfinamide 37 by using Ellman's methodology (Ellman, J. A., *Tetrahedron*, 55:8883-8904 (1999); Ellman, J. A., *J. Am. Chem. Soc.*, 119:9913-9914 (1997)).

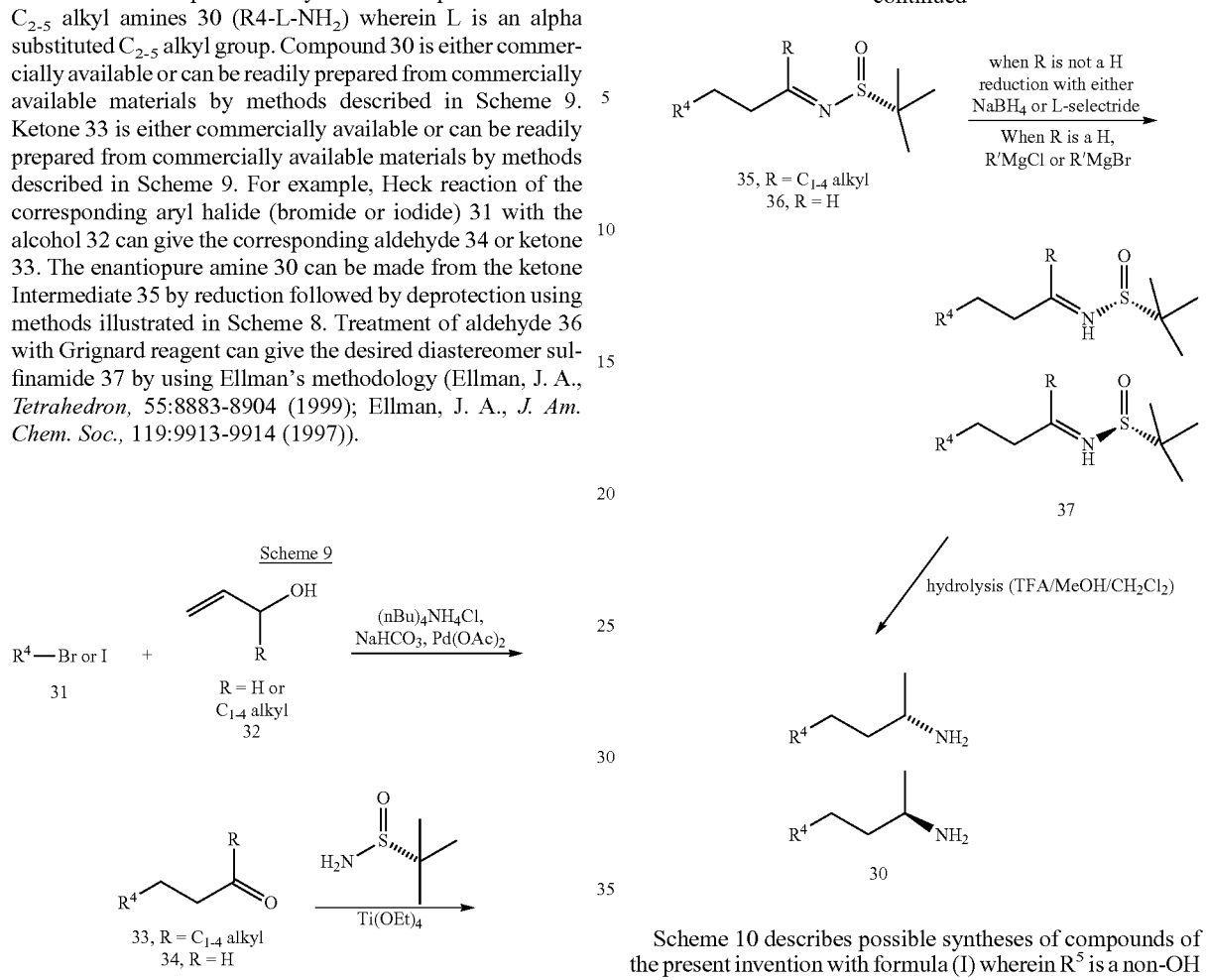

Scheme 10 describes possible syntheses of compounds of the present invention with formula (I) wherein $R^5$ is a non-OH substitution.

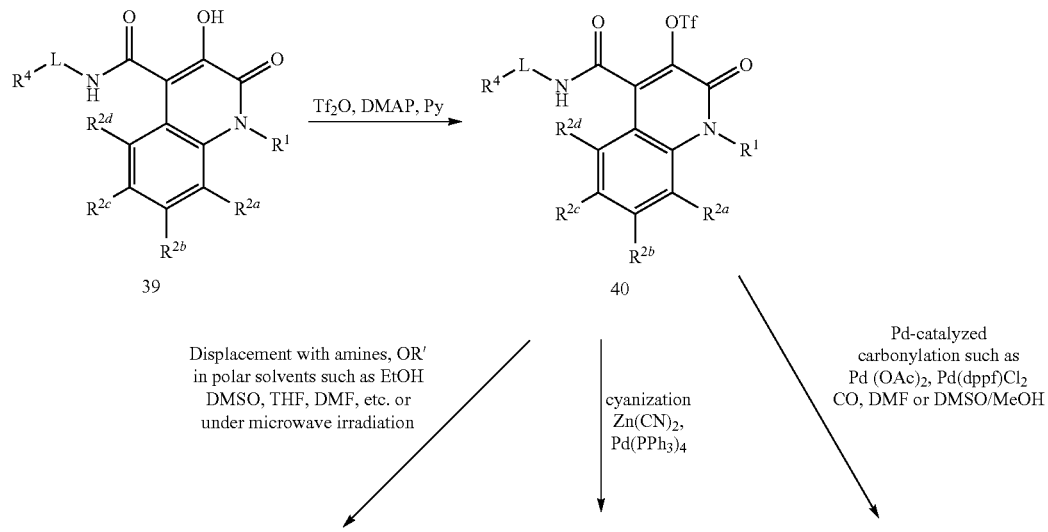

41

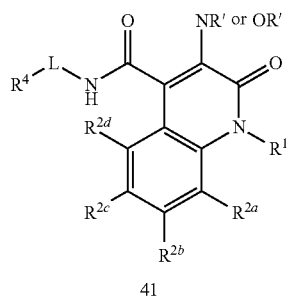

41

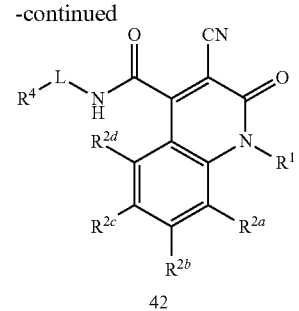

42

42

-continued

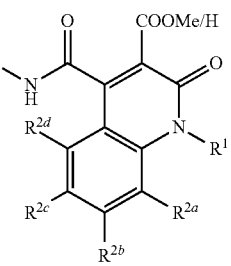

43

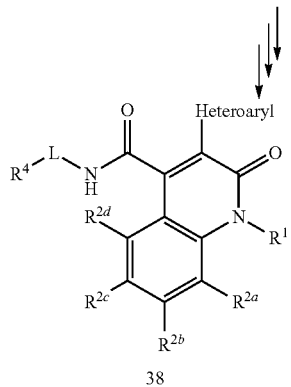

38

Scheme 11 illustrates a preparation of N-1 substituted analog 44 from Intermediate 45. The hydroxyl group in 45 can be selectively protected as OMe or OBn to give Intermediate 46. Alkylation of 46 with R1-X (X=Br, I, Cl, OMs or OTs) can be performed using $K_2CO_3$ or $Cs_2CO_3$ as the base in solvent such as DMF. Arylation of the N-1 NH of 47 can be realized by using Chan-Lam Cu-prompted C—N cross-coupling with $R^1$—$B(OH)_2$ and related boron reagents or Buchwald-Hartwig Pd-catalyzed cross-coupling with R1-halides. Deprotection of 47 can give the desired compound 43.

-continued

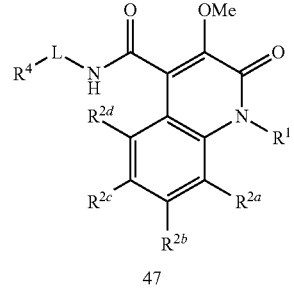

47 demethyaltion
such as BBr₃, BCl₃, etc

Scheme 11

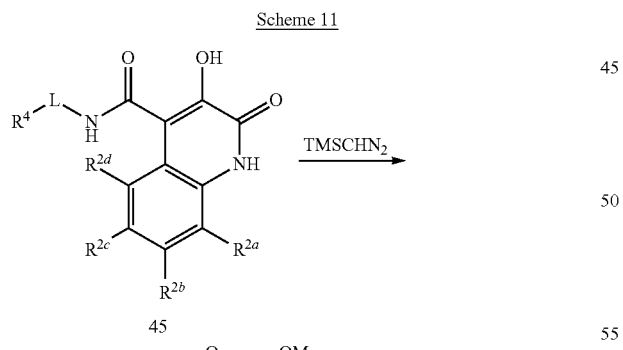

45

TMSCHN₂ →

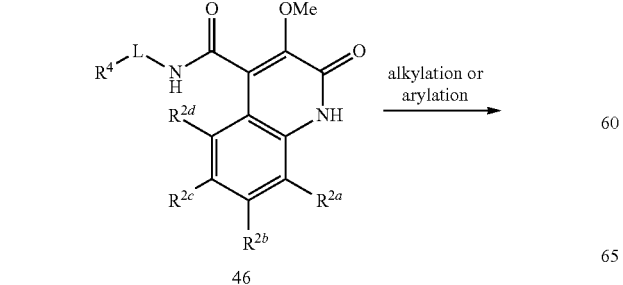

46 alkylation or arylation →

44

General Methods

Products were analyzed by reverse phase analytical HPLC carried out on a Shimadzu Analytical HPLC system running DISCOVERY VP® software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B:

10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm). Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running DISCOVERY VP® software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Luna Axia 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running DISCOVERY VP® software, coupled with a Waters ZQ mass spectrometer running MassLynx version 3.5 software using:

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm) Flow rate was 4 ml/min. and UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5 μm C18 (2.0×30 mm) Flow rate was 1 ml/min. and UV detection was set to 220 nm. The LC column was maintained at room temperature.

Method C: A linear gradient using solvent A (10% acetonitrile, 90% water, 10 mM $NH_4OAc$) and solvent B (90% acetonitrile, 10% water, 10 mM $NH_4OAc$); 0-100% of solvent B over 4 min and then 100% of solvent B over 1 min. Column: PHENOMENEX® Luna 5 μm C18 (4.5×50 mm) Flow rate was 4 ml/min. and UV detection was set to 220 nm. The LC column was maintained at room temperature.

Method D: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: Luna C-18 5 μm (4.5×30 mm) Flow rate was 1 ml/min. and UV detection was set to 220 nm. The LC column was maintained at room temperature.

Method E: A linear gradient using solvent A (10% MeOH, 90% water, 10 mM $NH_4OAc$) and solvent B (90% MeOH, 10% water, 10 mM $NH_4OAc$); 0-100% of solvent B over 4 min and then 100% of solvent B over 1 min. Column: PHENOMENEX® Luna 5 μm C18 (4.5×50 mm) Flow rate was 4 ml/min. and UV detection was set to 220 nm. The LC column was maintained at room temperature.

Method F: A linear gradient using solvent A (10 mM ammonium acetate, 95% water, 5% ACN) and solvent B (10 mM ammonium acetate, 95% ACN, 5% water); 0-100% of solvent B over 4 min and then 100% of solvent B over 1 min. Column. Mac-Mod Halo (C18, 4.6×50 mm) Flow rate was 4 ml/min. and UV detection was set to 220 nm. The LC column was maintained at room temperature.

Preparative HPLC Methods Employed in the Purification of Products

Method G: Linear gradient of 0 to 100% B over 10 min, with 5 min hold time at 100% B Shimadzu LC-8A binary pumps Waters ZQ mass spectrometer using Waters MassLynx 4.0 SP4 MS software UV visualization at 220 nm Column: Waters SunFire 19×100 mm 5 μm C18

Flow rate: 20 ml/min

Peak collection triggered by mass spectrometry

Solvent A: 0.1% TFA, 10% ACN, 90% water

Solvent B: 0.1% TFA, 90% ACN, 10% water

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 μm (4.6×150 mm) Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column. Xbridge Phenyl 3.5 μm (4.6×150 mm) Flow rate was 2 ml/min. and UV detection was set to 220 nm. The LC column was maintained at room temperature.

NMR Employed in Characterization of Examples $^1$H NMR spectra were obtained with Bruker or JEOL fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman et al., *Science*, 235:442-447 (1987); Yanagisawa et al., *Nature*, 332:411-415 (1988); Folkman et al., *J. Biol. Chem.*, 267:10931-10934 (1992); Janssens et al., *J. Biol. Chem.*, 267:14519-14522 (1992); Lamas et al., *Proc. Natl. Acad. Sci. U.S.A.*, 89:6348-6352 (1992); Luscher et al., *Hypertension*, 19:117-130 (1992); Williams et al., *Am. Rev. Respir. Dis.*, 146:545-S50 (1992); and Bevilacqua et al., *J. Clin. Invest.*, 91:379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation*, 79:8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos et al., *Circulation*, 106:1321-1326 (2002)). Notably, the endothelial lipase-mediated binding and uptake of HDL particles and the selective uptake of HDL-derived cholesterol esters have been reported to be independent of its enzymatic lipolytic activity (Strauss et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 uL of 1 mM DMPG in a 1:1 mixture of MeOH and CHCl$_3$ with 15 uL of 1 mM A10070 in a 1:1 mixture of MeOH and CHCl$_3$. The mixture was dried under nitrogen and resuspended in 150 uL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 uL of assay buffer (50 mM HEPES pH 8.0, 50 mM NaCl and 1 mM CaCl$_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 uL of a 1:4 dilution of vesicles. The final total reaction volume was 100 uL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. The EL IC$_{50}$ values measured for the following examples are listed in Table 1.

TABLE 1

| Ex. No. | HLE_EL_CRC IC$_{50}$ (nM) |
|---|---|
| 1 | 10 |
| 2 | 13 |
| 3 | 10 |
| 5 | 11 |
| 26 | 91 |
| 27 | 35 |
| 28 | 35 |
| 42 | 96 |
| 43 | 70 |
| 50 | 12 |
| 51 | 40 |
| 55 | 25 |
| 64 | 64 |
| 85 | 43 |
| 86 | 37 |
| 90 | 83 |
| 92 | 84 |
| 96 | 8526 |
| 103 | 9361 |
| 105 | 100 |
| 107 | 11070 |
| 109 | 2907 |
| 133 | 10 |
| 141 | 1701 |
| 147 | 49 |
| 151 | 75 |
| 155 | 3116 |
| 172 | 10 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, β$_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the

*Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The fol-

Intermediate 1.
3-(3,4-dichlorophenyl)propan-1-amine hydrochloride

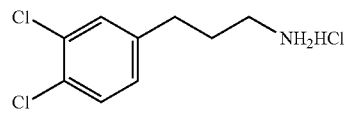

Intermediate 1A.
3-(3,4-dichlorophenyl)propanamide

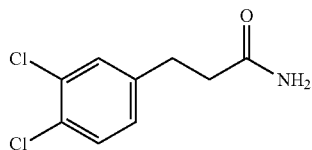 [SMILES: NC(=O)CCc1ccc(Cl)c(Cl)c1]

To a solution of 3-(3,4-dichlorophenyl)propanoic acid (12.4 g, 56.6 mmol) in CH$_2$Cl$_2$ (150 mL) was added oxalyl chloride (5.95 mL, 67.9 mmol) dropwise, followed by addition of DMF (0.044 mL, 0.57 mmol) at 0° C. The ice bath was removed after 30 min, and the mixture was stirred at rt for 3 h. LCMS showed the completion of the reaction. The reaction mixture was concentrated, and dried under vacuum for 0.5 h. The acid chloride was diluted in ca. 20 mL of Et$_2$O. The Et$_2$O solution was added portion-wise to the stirred solution of conc. aq ammonium hydroxide (ca. 30% of NH$_3$, 180 mL) at 0° C. A white precipitate formed during the addition. The ice bath was removed, and the mixture was stirred at rt for 2 h. The white precipitate was filtered, washed with H$_2$O, and dried under vacuum overnight to give Intermediate 1A (11.90 g, 54.6 mmol, 96% yield) as a white crystalline solid. LC-MS: 218.3 (M+H), 216.2 (M−H). RT=2.60 min (Method E).

Intermediate 1

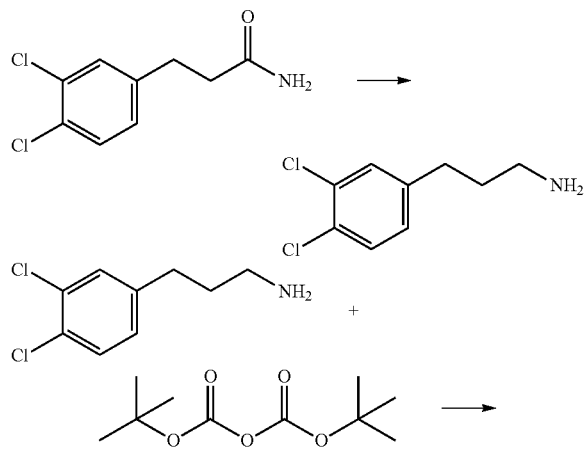

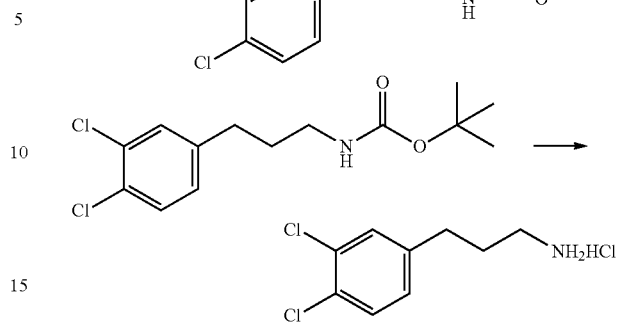

To a solution of Intermediate 1A (8.0 g, 36.7 mmol) in THF (35 mL) was added LAH (40.4 mL, 2 M in THF, 81 mmol) dropwise for 40 min at 0° C. under Ar. The colorless solution turned yellowish brown, and a precipitate formed after stirring at rt for 30 min. The suspension was stirred at rt for 6 h. The reaction mixture was cooled to 0° C. and quenched by careful addition of H$_2$O (3 mL), 15% NaOH (3 mL) and then H$_2$O (9 mL). Et$_2$O (ca. 100 mL) was added. The mixture was stirred at rt for 20 min then filtered through Celite® and rinsed with Et$_2$O (ca. 150 mL). The filtrate was concentrated. The residue was dissolved in Et$_2$O (100 mL) and CH$_2$Cl$_2$ (10 mL), dried over Na$_2$SO$_4$, filtered and concentrated to give a light tan oil after drying under vacuum. 3-(3,4-Dichlorophenyl)propan-1-amine was taken to the next step without further purification. LC-MS: 203.9 (M+H), RT=2.76 min (Method A). TEA (8.36 mL, 60.0 mmol) was added to 3-(3,4-dichlorophenyl)propan-1-amine (6.8 g, 33.3 mmol) in THF (100 mL) followed by the addition of di-tert-butyl dicarbonate (8.22 g, 37.6 mmol) and the reaction mixture was stirred at rt overnight. The solvent was removed under vacuum and Et$_2$O was added. The organic solution was washed with H$_2$O and then brine. The organic layer was dried over MgSO$_4$, filtered and concentrated. The residue was purified by ISCO chromatography using Hexanes/EtOAc to give the product tert-butyl 3-(3,4-dichlorophenyl)propylcarbamate (6.9 g, 23 mmol, 68% yield) as a colorless oil. LC-MS (ESI) 248.0 (M−tBu+H), RT=3.85 min (Method A). tert-Butyl 3-(3,4-dichlorophenyl)propylcarbamate (3.48 g, 11.44 mmol) was stirred in 4N HCl in dioxane (20 mL) at rt for 2 h. The volume of the mixture was reduced under reduced pressure, and Et$_2$O was added. The reaction mixture was stirred at rt for 30 min. The resulting precipitate was filtered and rinsed with Et$_2$O to give Intermediate 1 (1.95 g, 8.11 mmol, 70.9% yield). LCMS=203.9 [M+1], RT=1.51 min (Method B).

Intermediate 2.
3-(2,4-dichlorophenyl)propan-1-amine hydrochloride

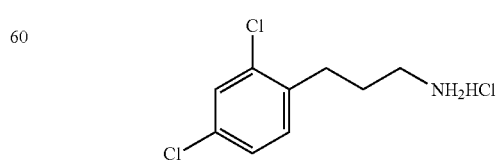

Intermediate 2 was prepared according to the procedures described in Intermediate 1 using 3-(2,4-dichlorophenyl)propanoic acid as the starting material. LC-MS (ESI) m/z 204.0 (M+H)⁺, RT=1.56 min (Method B).

Intermediate 3.
3-(2,6-dichlorophenyl)propan-1-amine hydrochloride

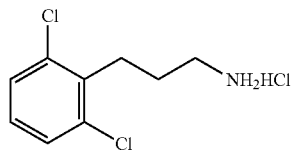

Intermediate 3 was prepared according to the procedures described in Intermediate 1 using 3-(2,6-dichlorophenyl)propanoic acid as the starting material. LC-MS (ESI) m/z 204.0 (M+H)⁺, RT=1.46 min (Method B).

Intermediate 4.
3-(2-(trifluoromethyl)phenyl)propan-1-amine hydrochloride

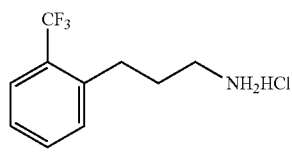

Intermediate 4 was prepared according to the procedures described in Intermediate 1 using 3-(2-(trifluoromethyl)phenyl)propanoic acid as the starting material. LC-MS (ESI) m/z 204.0 (M+H)⁺, RT=1.40 min (Method B).

Intermediate 5.
(R)-1-(2,6-dichlorophenoxy)propan-2-amine, trifluoroacetic acid salt

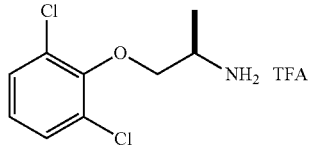

Intermediate 5A. (R)-tert-butyl 1-bromopropan-2-ylcarbamate

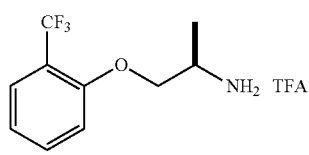

(R)-tert-Butyl 1-hydroxypropan-2-ylcarbamate (1 g, 5.71 mmol) and carbon tetrabromide (2.84 g, 8.56 mmol) were stirred in CH₂Cl₂ (20 mL) at −20° C. under argon. A solution of triphenylphosphine (2.40 g, 9.13 mmol) in CH₂Cl₂ (5 mL) was added dropwise. The reaction was allowed to reach rt and stirred for 14 h. H₂O (50 mL) was added to the reaction mixture and the aqueous layer was removed and the CH₂Cl₂ layer was dried over Na₂SO₄, filtered, and evaporated. The residue was applied to a silica ISCO column and eluted with 5:1 hexanes/EtOAc. Intermediate 5A (0.68 g, 2.86 mmol, 50.0% yield) was isolated as a white solid. LC-MS (ESI) 183.9 (M−tBu+H), RT=1.76 min (Method B).

Intermediate 5B. (R)-tert-butyl 1-(2,6-dichlorophenoxy)propan-2-ylcarbamate

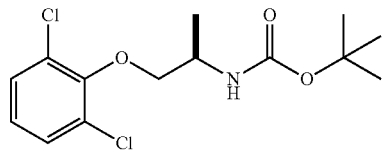 [SMILES: C[C@H](COc1c(Cl)cccc1Cl)NC(=O)OC(C)(C)C]

Intermediate 5A (230 mg, 0.966 mmol), cesium carbonate (409 mg, 1.256 mmol) and 2,6-dichlorophenol (157 mg, 0.966 mmol) were heated in acetone (1 mL) under microwave irradiation at 100° C. for 30 min. The solvents were removed and CH₂Cl₂ was added. The organic phase was washed with H₂O, dried over Na₂SO₄, filtered and concentrated. The colorless oil was purified by ISCO (hexanes/EtOAc) to give 100 mg of Intermediate 5B (100 mg, 0.312 mmol, 32.3% yield). LC-MS 219.9 (M-Boc+H), RT=2.23 min (Method B).

Intermediate 5

Intermediate 5B (95 mg, 0.297 mmol) was stirred in CH₂Cl₂ (1 mL) and TFA (1 mL) was added. The reaction was stirred at rt until LC-MS showed the completion of the reaction. The reaction mixture was concentrated and diluted with CH₂Cl₂. The organic phase was washed with saturated NaHCO₃ and H₂O and brine, dried over Na₂SO₄, filtered, and concentrated. Intermediate 5 was used directly for the next step after vacuum drying as the TFA salt (85 mg, 90%). MS (ESI) m/z 219.9, 222.0 (M+H)⁺, RT=1.34 min (Method B).

Intermediate 6. (R)-1-(2-(trifluoromethyl)phenoxy) propan-2-amine, trifluoroacetic acid salt

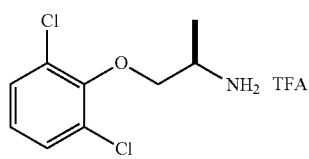

Intermediate 6 was prepared according to the procedures described in Intermediate 5 using (R)-tert-butyl 1-(2-(trifluoromethyl)phenoxyl) propan-2-ylcarbamate as the starting material. LC-MS (ESI) m/z 220.1 (M+H), RT=2.30 min (Method A).

Intermediate 7. 3-(3,4-dichlorophenylthio)propan-1-amine

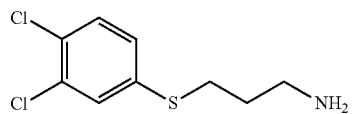 [SMILES: NCCCSc1ccc(Cl)c(Cl)c1]

Intermediate 7A. 2-(3-(3,4-dichlorophenylthio)propyl)isoindoline-1,3-dione

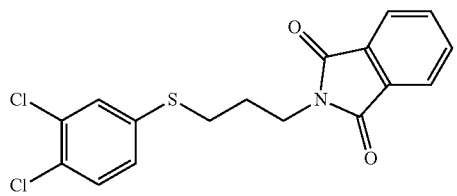 [SMILES: O=C1c2ccccc2C(=O)N1CCCSc1ccc(Cl)c(Cl)c1]

3,4-Dichlorobenzenethiol (500 mg, 2.79 mmol) and 2-(3-bromopropyl)isoindoline-1,3-dione (823 mg, 3.07 mmol) were stirred in DMF (2 mL) at rt. $Cs_2CO_3$ (1.64 g, 5.03 mmol) was added. The reaction mixture was stirred at rt for 14 h. $H_2O$ was added and the aqueous phase was extracted with EtOAc. The organic layer was dried over $MgSO_4$, filtered and concentrated to give crude product. It was then triturated with ether to yield a white precipitate which was filtered and dried to give Intermediate 7A (760 mg, 2.075 mmol, 74.3% yield). LC-MS (ESI) 365.8 (M+H). RT=4.00 min (Method A).

Intermediate 7

To a solution of Intermediate 7A (100 mg, 0.273 mmol) in EtOH (1 mL) was added Hydrazine (0.052 mL, 1.64 mmol). The reaction mixture was stirred at 60° C. for 3 h, diluted with EtOAc, filtered and the filter cake was washed with MeOH. The filtrate was dried over $Na_2SO_4$ and evaporated under reduced pressure to give Intermediate 7 (63 mg, 0.267 mmol, 98% yield). LC-MS (ESI) 237 (M+H). RT=1.68 min (Method B). $^1$H NMR (500 MHz, $CHCl_3$-D) δ 1.64 (s, 2 H) 1.71-1.73 (m, 2 H) 2.79-2.81 (t, J=6.60 Hz, 2 H) 2.98-3.00 (t, J=6.05 Hz, 2 H) 7.42 (s, 2.75 Hz, 1 H) 7.29-7.40 (d, J=2.75 Hz, 2 H).

Intermediate 8. (1-(3,4-dichlorophenylsulfonyl)piperidin-4-yl)methanamine

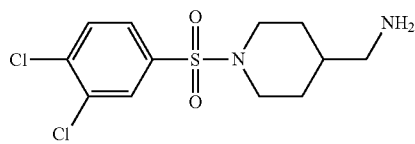 [SMILES: NCC1CCN(S(=O)(=O)c2ccc(Cl)c(Cl)c2)CC1]

Intermediate 8A. tert-butyl (1-(3,4-dichlorophenylsulfonyl)piperidin-4-yl)methylcarbamate

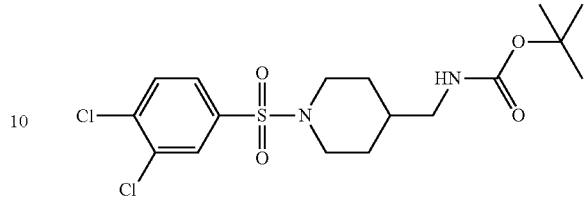

To a solution of 3,4-dichlorobenzene-1-sulfonyl chloride (470 mg, 1.91 mmol) was added tert-butyl piperidin-4-ylmethylcarbamate (410 mg, 1.91 mmol), followed by triethylamine (0.267 mL, 1.91 mmol). The reaction mixture was stirred overnight then diluted with DCM. The organic phase was washed with 1N HCl, $H_2O$, and brine, dried over $Na_2SO_4$, then filtered. The solvent was evaporated under reduced pressure and the residue was purified on a 24 g cartridge using 0 to 100% EtOAc in Hexane and then 0 to 20% MeOH in DCM to yield Intermediate 8A (800 mg, 1.89 mmol, 99% yield). LC-MS (ESI) 324.1. (M+H-Boc), RT=1.55 min (Method B).

Intermediate 8

To a solution of Intermediate 8A (100 mg, 0.236 mmol) in DCM (1 mL) was added HCl (0.118 mL, 0.472 mol). The reaction mixture was stirred at rt for 16 h. The reaction mixture was evaporated to dryness and the residue was titrated with $Et_2O$. The Intermediate 8 was collected by filtration and dried to give Intermediate 8 (75 mg, 0.23 mmol, 98% yield). LC-MS (ESI) 324.1 (M+H), retention time=2.74 min (Method A).

Intermediate 9. 3-(2,6-dichlorophenoxy)propan-1-amine

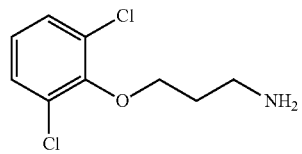 [SMILES: NCCCOc1c(Cl)cccc1Cl]

Intermediate 9A. 2-(3-(2,6-dichlorophenoxy)propyl)isoindoline-1,3-dione

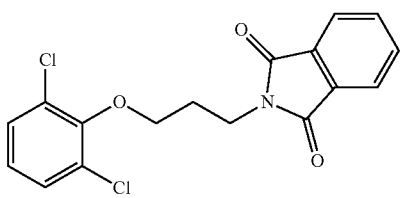 [SMILES: O=C1c2ccccc2C(=O)N1CCCOc1c(Cl)cccc1Cl]

A solution of 2,6-dichlorophenol (500 mg, 3.07 mmol), tetrabutyl ammonium iodide (227 mg, 0.613 mmol) and 2-(3-bromopropyl)isoindoline-1,3-dione (905 mg, 3.37 mmol)

was stirred in THF (5 mL) at rt. Cs$_2$CO$_3$ (1.80 g, 5.52 mmol) was added. The resulting mixture was stirred at 50° C. for 16 h. H$_2$O was added to the reaction mixture and the aqueous layer was extracted with EtOAc. The organic layer was dried over MgSO$_4$, filtered and concentrated. The residue was purified by triturating with Et$_2$O to yield Intermediate 9A (1010 mg, 2.88 mmol, 94% yield) as a white powder. LC-MS (ESI) 365 (M+H), RT=2.23 min (Method B).

Intermediate 9

To a solution of Intermediate 9A (1.01 g, 2.88 mmol) in EtOH (1 mL) was added hydrazine (0.549 mL, 17.3 mmol). The reaction mixture was stirred at 60° C. for 3 h, allowed to cool to RT, and diluted with ether. The resulting precipitate was filtered and washed with ether. The filtrate was evaporated under reduced pressure to give Intermediate 9 (625 mg, 2.84 mmol, 98% yield). LC-MS (ESI) 222 (M+H), RT=1.37 min (Method B).

Intermediate 10.
3-(2-(trifluoromethyl)phenoxy)propan-1-amine

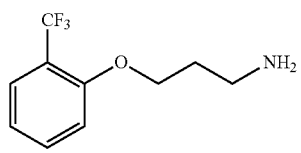 [SMILES: NCCCOc1ccccc1C(F)(F)F]

Intermediate 10 (50 mg, 0.228 mmol, 80% yield) was prepared as a white powder following the procedure described for Intermediate 9 using 2-trifluoromethylphenol and 2,6-dichlorophenol as starting materials. LC-MS (ESI) 220 (M+H), RT=1.36 min (Method B).

Intermediate 11.
3-(4-chlorophenoxy)propan-1-amine

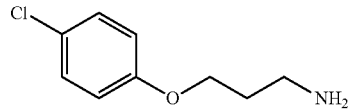 [SMILES: NCCCOc1ccc(Cl)cc1]

Intermediate 11 (150 mg, 0.808 mmol, 85% yield) was prepared as a white powder following the procedure described for Intermediate 9 replacing 2,6-dichlorophenol with 4-chlorophenol as starting material. LC-MS (ESI) 186 (M+H), RT=1.41 min (Method B).

Intermediate 12.
3-(2,3-dichlorophenoxy)propan-1-amine

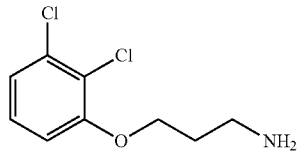 [SMILES: NCCCOc1cccc(Cl)c1Cl]

Intermediate 12 (55 mg, 0.250 mmol, 88% yield) was prepared as a white powder following the procedure described for Intermediate 9 using 2,3-dichlorophenol and 2,6-dichlorophenol as starting materials. LC-MS (ESI) 221 (M+H), RT=1.48 min (Method B).

Intermediate 13.
(R)-4-(2,6-dichlorophenoxy)butan-2-amine

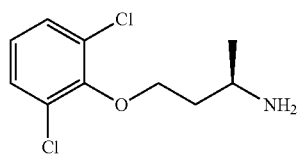

Intermediate 13A. (R)-2-(4-(2,6-dichlorophenoxy)butan-2-yl)isoindoline-1,3-dione

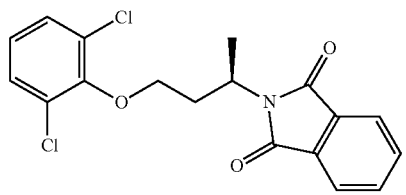 [SMILES: C[C@H](CCOc1c(Cl)cccc1Cl)N1C(=O)c2ccccc2C1=O]

To a solution of 2,6-dichlorophenol (14.9 mg, 0.091 mmol) in THF (1.5 mL) was added (R)-2-(4-hydroxybutan-2-yl)isoindoline-1,3-dione (20 mg, 0.091 mmol) and triphenylphosphine (47.9 mg, 0.182 mmol) and the reaction mixture was cooled to 0° C. in an ice/water bath. DIAD (0.035 mL, 0.182 mmol) was added drop wise and the reaction mixture was stirred at 0° C. for 1 h. The reaction mixture was allowed to warm to rt and was stirred at rt overnight. The reaction mixture was concentrated under vacuum to yield a yellow oil that was diluted with a minimal amount of DCM, loaded onto a 12 g ISCO column and purified by ISCO. Intermediate 13A (0.1003 g, 96% yield) was isolated as a clear oil. LC-MS (ESI) 365 (M+H), RT=2.84 min (Method A). NMR indicated that the final product contained reduced DIAD.

Intermediate 13

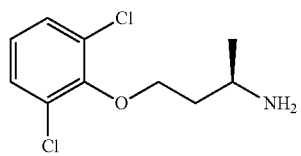

To a solution of Intermediate 13A (33 mg, 0.091 mmol) in EtOH (1 mL) was added hydrazine (0.017 mL, 0.544 mmol). The reaction mixture was stirred at 60° C. for 3 h, allowed to cool to rt, and diluted with EtOAc. The precipitate was filtered and washed with MeOH. The filtrate was dried over Na$_2$SO$_4$ and evaporated under reduced pressure to give Intermediate 13 (18 mg, 0.077 mmol, 85% yield). LC-MS (ESI) 235 (M+H), RT=1.39 min (Method B).

Intermediate 14. (R)-4-(2-(trifluoromethyl)phenoxy)butan-2-amine

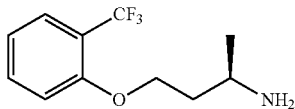

Intermediate 14 (55 mg, 0.250 mmol, 88% yield) was prepared as a white powder following the procedure described for Intermediate 13 by replacing 2,6-dichlorophenol with 2-trifluoromethylphenol. LC-MS (ESI) 221 (M+H), RT=1.48 min (Method B).

Intermediate 15. (R)-6-(trifluoromethyl)-2,3-dihydro-1H-inden-1-amine hydrochloride

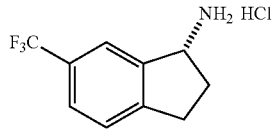 [SMILES: Cl ; N[C@@H]1CCc2ccc(C(F)(F)F)cc21]

Intermediate 15A. (R)-2-methyl-N-(6-(trifluoromethyl)-2,3-dihydro-1H-inden-1-ylidene)propane-2-sulfinamide

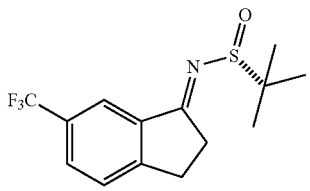 [SMILES: CC(C)(C)[S@@](=O)/N=C1\CCc2ccc(C(F)(F)F)cc21]

To a stirred solution of (R)-2-methylpropane-2-sulfinamide (578 mg, 4.77 mmol) and 6-(trifluoromethyl)-2,3-dihydro-1H-inden-1-one (1000 mg, 5.00 mmol) in THF (4 mL) at rt was added tetraethoxytitanium (1.88 mL, 9.08 mmol). The reaction mixture was heated at 75° C. overnight. The reaction mixture was allowed to cool and used directly in the next step. LC-MS (ESI) 304.0 (M+H), RT=2.20 min (Method B).

Intermediate 15B. (R)-2-methyl-N((R)-6-(trifluoromethyl)-2,3-dihydro-1H-inden-1-yl)propane-2-sulfinamide

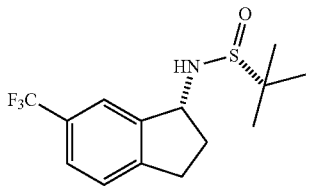 [SMILES: CC(C)(C)[S@@](=O)N[C@@H]1CCc2ccc(C(F)(F)F)cc21]

Sodium borohydride (756 mg, 20.0 mmol) was stirred in a round-bottomed flask under argon at −40 to −50° C. The reaction mixture of Intermediate 15A was added dropwise to the flask, and THF was added to the reaction mixture (ca. 0.6 M). The resulting mixture was allowed to warm up to 0° C. during 1.5 h period. The reaction mixture was cooled in dry ice and MeOH was added dropwise until gas evolution stopped. The mixture was stirred at rt for 20 min, filtered through Celite® and rinsed with EtOAc then CH$_2$Cl$_2$. The filtrate was washed with brine (2×) and dried over MgSO$_4$, filtered and concentrated. The residue was purified on ISCO (hexanes/EtOAc) to give Intermediate 15B (370 mg, 1.21 mmol, 26.7% yield) as colorless crystals. LC-MS (ESI) 306.0 (M+H), RT=2.10 min (Method B).

Intermediate 15

Intermediate 15B (370 mg, 1.21 mmol) was stirred in MeOH (5 mL) at rt. 4N HCl in dioxane (2 mL) was added. The resulting mixture was stirred at rt for 20 min. The solvents were evaporated and CH$_2$Cl$_2$ (3×) was added and evaporated. The resulting white solids were vacuum dried for 1 h to give Intermediate 15 (84 mg, 0.35 mmol, 29% yield) and methyl 2-methylpropane-2-sulfinate. The HCl salt was used directly in the next step. $^1$H NMR (400 MHz, MeOD) δ ppm 7.57 (1 H, d, J=7.8 Hz), 7.47 (1 H, d, J=7.6 Hz), 7.25 (1 H, t, J=7.8 Hz), 4.88 (1 H, dd, J=7.8, 4.8 Hz), 3.09-3.23 (1 H, m), 2.90-3.08 (1 H, m), 2.64 (1 H, dddd, J=14.1, 8.5, 8.3, 5.7 Hz), 2.01-2.23 (1 H, m, J=14.1, 8.7, 5.3, 5.3 Hz).

Intermediate 16. ethyl 3-hydroxy-1-methyl-2-oxo-1,2-dihydroquinoline-4-carboxylate

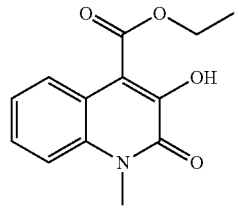 [SMILES: CCOC(=O)c1c(O)c(=O)n(C)c2ccccc12]

1-Methylindoline-2,3-dione (5.0 g, 31.0 mmol) was stirred in DMF (15 mL) and Ethanol (85 mL) at 0° C. Ethyl 2-diazoacetate (4.51 mL, 43.4 mmol) was added. The ice bath was removed and the mixture was stirred at rt for two days. The mixture was evaporated to remove most of the EtOH. 1N HCl (ca. 100 mL) was added. It was stirred at rt for 3 h. LC-MS showed the desired ring expansion product. The precipitate was filtered and rinsed with H$_2$O (2×) and dried under vacuum to give Intermediate 16 (5.05 g, 20.42 mmol, 94% yield) as slightly tan solids. LC-MS (ESI) 248.0 (M+H), RT=2.91 min (Method A).

Intermediate 17. ethyl 3-hydroxy-6-methyl-2-oxo-1,2-dihydroquinoline-4-carboxylate

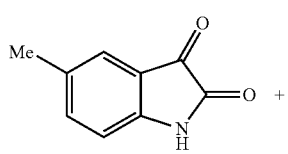

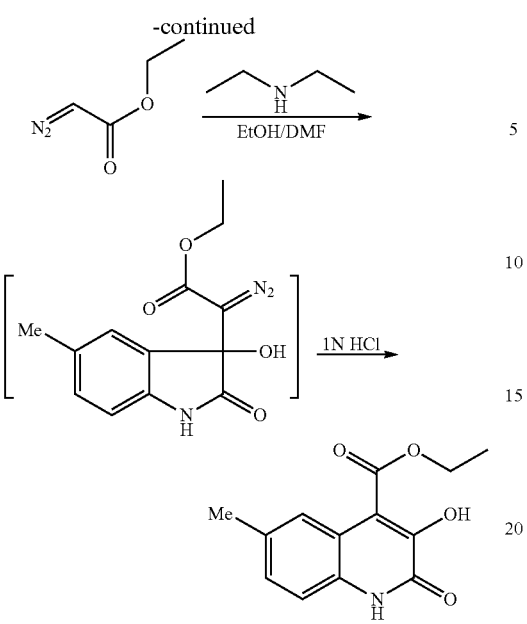

Intermediate 17 was prepared as a white powder following the procedure described for Intermediate 16 by replacing indoline-2,3-dione with 5-methylindoline-2,3-dione. ¹H NMR (400 MHz, chloroform-d) δ ppm 11.23 (1 H, br. s.), 9.64 (1 H, br. s.), 7.83 (1 H, s), 7.01-7.56 (2 H, m), 4.58 (2 H, q, J=7.1 Hz), 2.43 (4 H, s), 1.51 (3 H, t, J=7.1 Hz). LC-MS (ESI) m/z 247.9 (M+H), RT=1.76 min (Method B)

Intermediate 18. ethyl 1-benzyl-3-hydroxy-2-oxo-1,2-dihydroquinoline-4-carboxylate

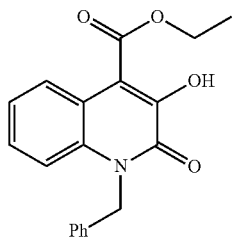 [SMILES: CCOC(=O)c1c(O)c(=O)n(Cc2ccccc2)c2ccccc12]

Intermediate 18 was prepared as a white powder following the procedure described for Intermediate 16 by replacing indoline-2,3-dione with 1-benzylindoline-2,3-dione. LC-MS (ESI) m/z 324.0 (M+H), RT=2.02 min (Method B)

Intermediate 19. ethyl 3-hydroxy-1-isopropyl-2-oxo-1,2-dihydroquinoline-4-carboxylate

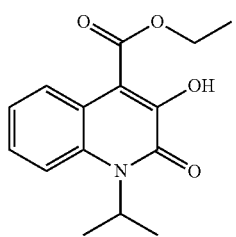 [SMILES: CCOC(=O)c1c(O)c(=O)n(C(C)C)c2ccccc12]

Intermediate 19 was prepared as a white powder following the procedure described for Intermediate 16 by replacing indoline-2,3-dione with 1-isopropylindoline-2,3-dione. ¹H NMR (400 MHz, chloroform-d) δ ppm 8.10 (1 H, br. s.), 7.77 (1 H, d, J=7.8 Hz), 7.60 (1 H, d, J=8.3 Hz), 7.42 (1 H, t, J=7.7 Hz), 7.27 (1 H, t, J=7.5 Hz), 4.53 (2 H, q, J=7.1 Hz), 1.45 (3 H, t, J=7.1 Hz). LC-MS (ESI) m/z 276.0 (M+H), RT=1.93 min (Method B)

Intermediate 20. ethyl 3-hydroxy-2-oxo-1-phenyl-1,2-dihydroquinoline-4-carboxylate

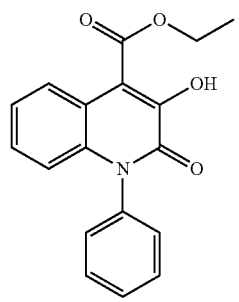 [SMILES: CCOC(=O)c1c(O)c(=O)n(-c2ccccc2)c2ccccc12]

Intermediate 20 was prepared as a white powder following the procedure described for Intermediate 16 by replacing indoline-2,3-dione with 1-phenylindoline-2,3-dione. ¹H NMR (400 MHz, chloroform-d) δ ppm 8.14 (1 H, s), 7.85 (1 H, dd, J=7.7, 1.9 Hz), 7.45-7.66 (3 H, m), 7.01-7.37 (4 H, m), 6.46-6.78 (1 H, m), 4.58 (2 H, q, J=7.2 Hz), 1.49 3 H, t, J=7.2 Hz). LC-MS (ESI) m/z 310.0 (M+H), RT=3.53 min (Method B).

Intermediate 21. ethyl 6-fluoro-3-hydroxy-2-oxo-1,2-dihydroquinoline-4-carboxylate

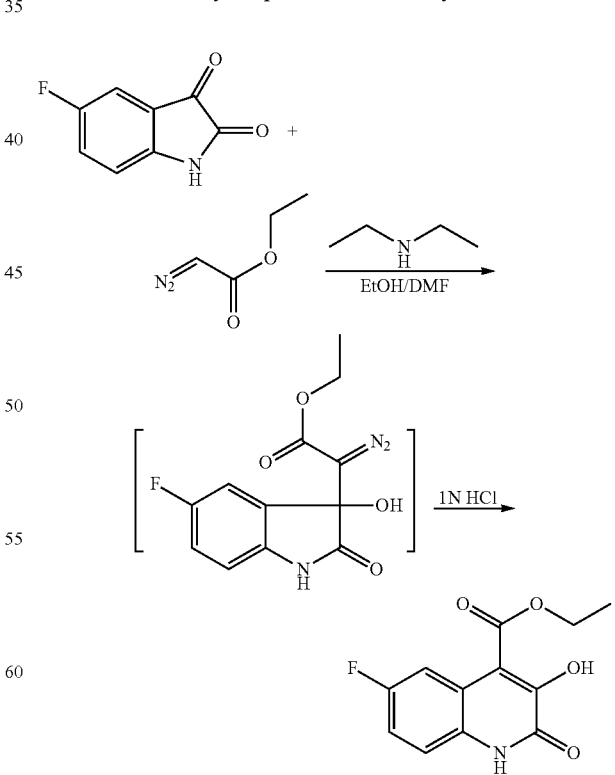

Intermediate 21 was prepared as a white powder following the procedure described for Intermediate 16 by replacing indoline-2,3-dione with 5-fluoroindoline-2,3-dione. LC-MS (ESI) m/z 251.9 (M+H), RT=1.74 min (Method B).

Intermediate 22. ethyl 8-fluoro-3-hydroxy-2-oxo-1,2-dihydroquinoline-4-carboxylate

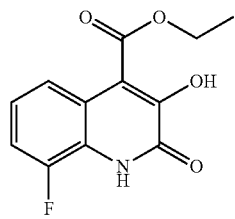 [SMILES: CCOC(=O)c1c(O)c(=O)[nH]c2c(F)cccc12]

Intermediate 22 was prepared as a white powder following the procedure described for Intermediate 16 by replacing indoline-2,3-dione with 2-fluoroindoline-2,3-dione. $^1$H NMR (400 MHz, chloroform-d) δ ppm 10.03 (1H, br. s.), 9.29 (1 H, br. s.), 7.87 (1 H, br. s.), 6.53-7.42 (2 H, m), 4.57 (2 H, q, J=6.8 Hz), 1.50 (3 H, t, J=6.8 Hz). LC-MS (ESI) 251.9 (M+H), RT=1.65 min (Method B).

Intermediate 23. ethyl 3-hydroxy-2-oxo-6-(trifluoromethoxy)-1,2-dihydroquinoline-4-carboxylate

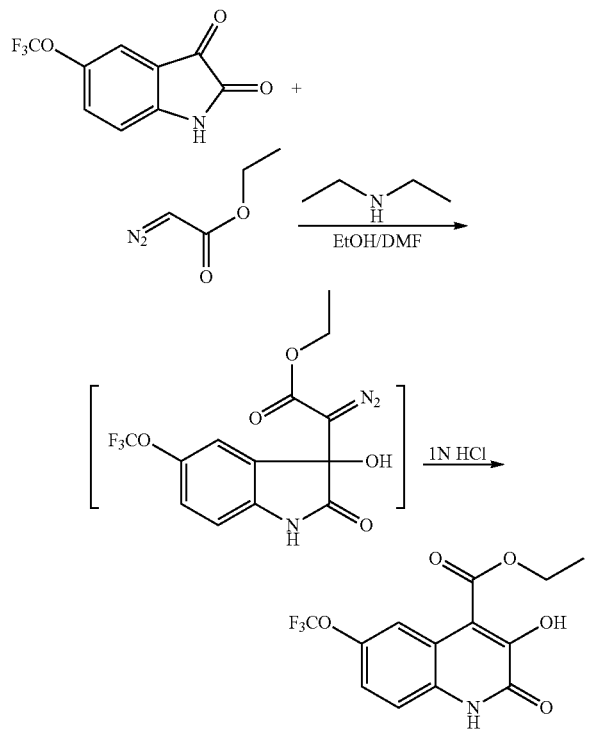

Intermediate 23 was prepared as a white powder following the procedure described for Intermediate 16 by replacing indoline-2,3-dione with 4-trifluoromethoxy-phenylindoline-2,3-dione. $^1$H NMR (400 MHz, chloroform-d) δ ppm 11.90 (1 H, br. s.), 11.28 (1 H, br. s.), 8.22 (1 H, br. s.), 7.36-7.53 (1 H, m), 7.43 (1 H, br. s.), 4.61 (2 H, d, J=7.1 Hz), 1.54 (3 H, t, J=6.9 Hz). LC-MS (ESI) m/z 317.9 (M+H), RT=2.00 min (Method B).

Intermediate 24. ethyl 7-chloro-3-hydroxy-2-oxo-1,2-dihydroquinoline-4-carboxylate

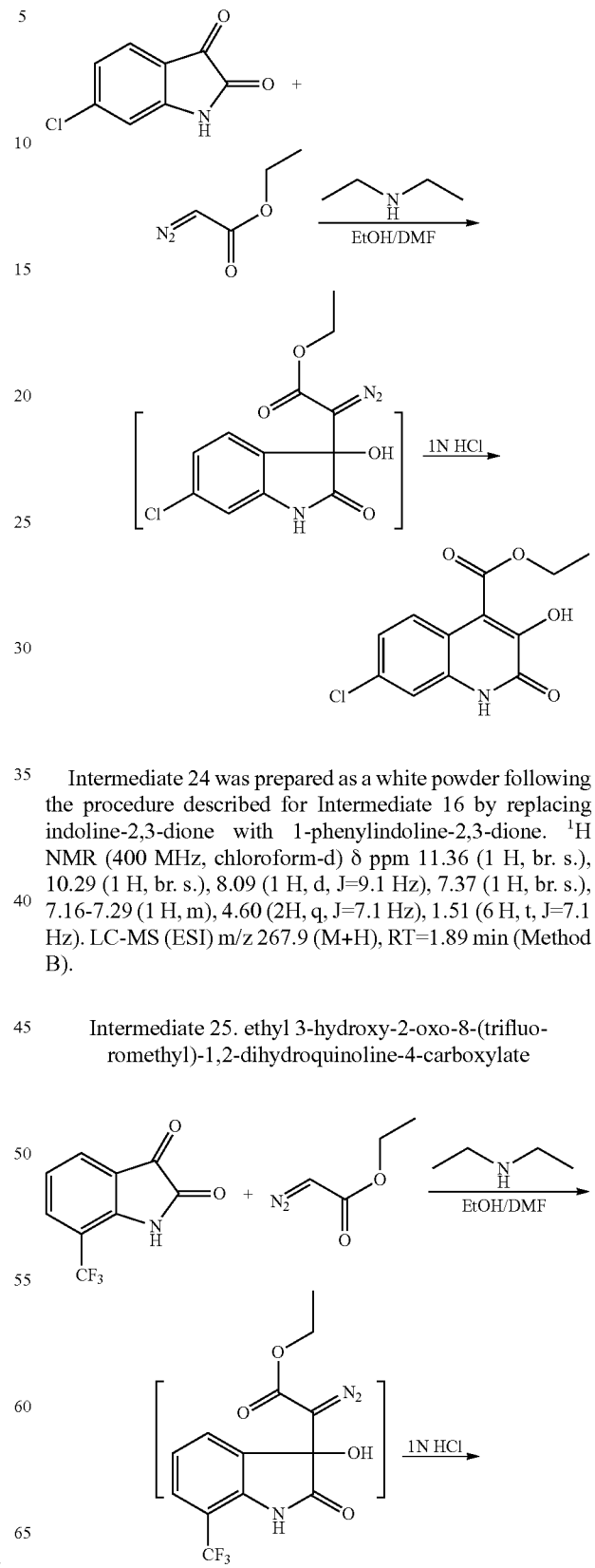

Intermediate 24 was prepared as a white powder following the procedure described for Intermediate 16 by replacing indoline-2,3-dione with 1-phenylindoline-2,3-dione. $^1$H NMR (400 MHz, chloroform-d) δ ppm 11.36 (1 H, br. s.), 10.29 (1 H, br. s.), 8.09 (1 H, d, J=9.1 Hz), 7.37 (1 H, br. s.), 7.16-7.29 (1 H, m), 4.60 (2H, q, J=7.1 Hz), 1.51 (6 H, t, J=7.1 Hz). LC-MS (ESI) m/z 267.9 (M+H), RT=1.89 min (Method B).

Intermediate 25. ethyl 3-hydroxy-2-oxo-8-(trifluoromethyl)-1,2-dihydroquinoline-4-carboxylate -continued

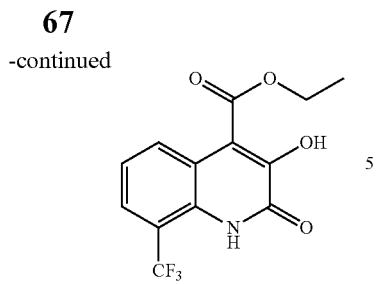

Intermediate 25 was prepared as a white powder following the procedure described for Intermediate 16 by replacing indoline-2,3-dione with 2-trifluoro-phenylindoline-2,3-dione. LC-MS (ESI) 317.9 (M+H), RT=1.90 min (Method B).

Intermediate 26. ethyl 3-hydroxy-6-iodo-2-oxo-1,2-dihydroquinoline-4-carboxylate

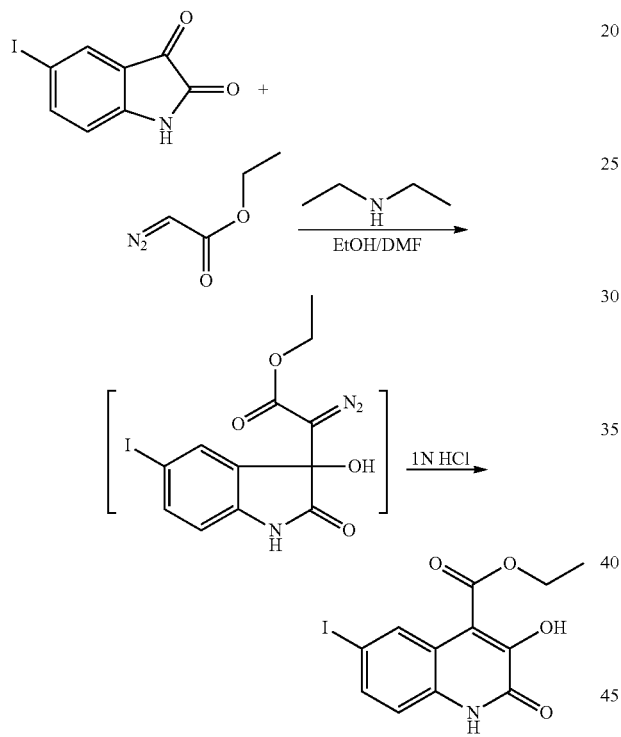

Intermediate 26 was prepared as a white powder the procedure described for Intermediate 16 by replacing indoline-2,3-dione with 4-iodo-phenylindoline-2,3-dione. $^1$H NMR (400 MHz, DMSO-d$_6$) δ ppm 12.41 (1 H, br. s.), 10.52 (1 H, br. s.), 7.33-8.21 (2 H, m), 7.14 (1 H, d, J=8.3 Hz), 4.41 (2 H, q, J=6.9 Hz), 3.34 (1 H, br. s.), 2.51 (1 H, br. s.), 1.33 (3 H, t, J=7.1 Hz). LC-MS (ESI) m/z 359.9 (M+H), RT=3.48 min (Method A).

Intermediate 27. ethyl 3-hydroxy-6-methoxy-2-oxo-1,2-dihydroquinoline-4-carboxylate

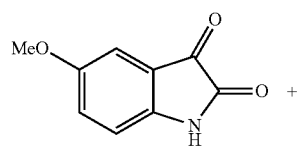

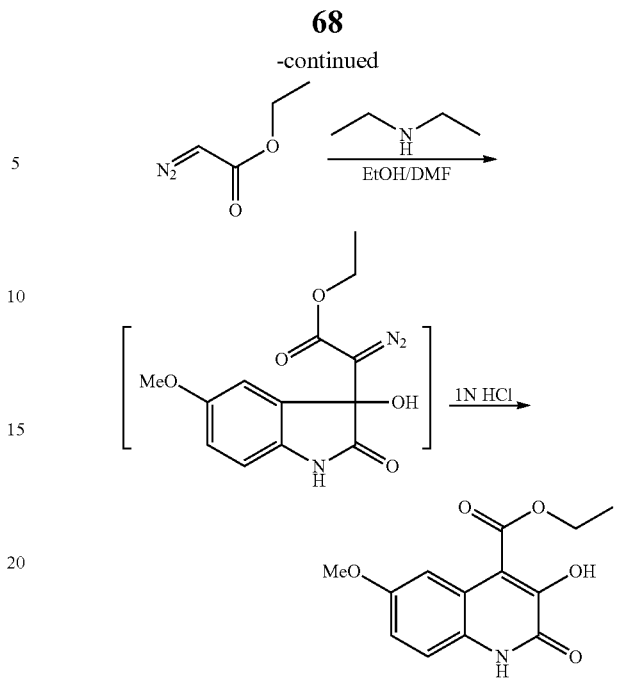

Intermediate 27 was prepared as a white powder following the procedure described for Intermediate 16 by replacing indoline-2,3-dione with 5-methoxyindoline-2,3-dione. $^1$H NMR (400 MHz, DMSO-d$_6$) δ ppm 12.20 (1 H, s), 10.22 (1 H, br. s.), 7.27 (1H, d, J=8.8 Hz), 7.04 (1H, dd, J=9.1, 2.5 Hz), 6.82 (1 H, d, J=2.5 Hz), 4.41 (2 H, q, J=7.1 Hz), 3.32 (3 H, s), 1.35 (3 H, t, J=7.1 Hz). LC-MS (ESI) m/z 264.0 (M+H), RT=1.64 min (Method B).

Intermediate 28. ethyl 3-isobutoxy-1-isobutyl-2-oxo-1,2-dihydroquinoline-4-carboxylate

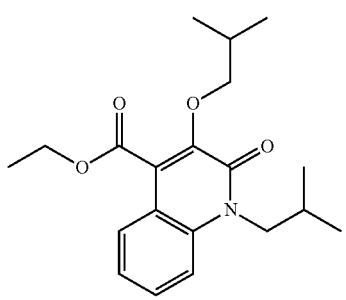 [SMILES: CCOC(=O)c1c(OCC(C)C)c(=O)n(CC(C)C)c2ccccc12]

To a solution of ethyl 3-hydroxy-2-oxo-1,2-dihydroquinoline-4-carboxylate (250 mg, 1.07 mmol) in DMF (6 mL) was added cesium carbonate (908 mg, 2.79 mmol), 1-bromo-2-methylpropane (294 mg, 2.14 mmol). The reaction was heated at 50° C. for 16 h. The reaction mixture was allowed to cool to rt and washed with EtOAc. The organic phase was then washed with H$_2$O and dried over Na$_2$SO$_4$ and concentrated in vacuo to give the crude product. Intermediate 28 was isolated via ISCO flash chromatography using a 40 g silica gel cartridge eluted with a 30-minute gradient from 0 to 100% EtOAc in hexane (350 mg, 1.01 mmol, 95% yield). LC-MS (ESI) m/z 346 (M+H), RT=2.30 min (Method B).

Intermediate 29. (R)-4-(3,4-dichlorophenyl)butan-2-amine hydrochloride

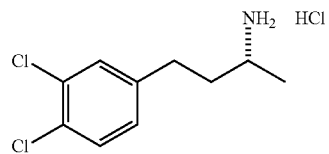

Intermediate 29A. 4-(3,4-dichlorophenyl)butan-2-one

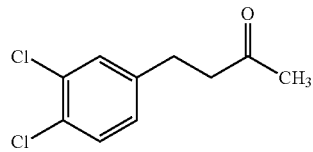

A microwave vial was charged with palladium acetate (0.165 g, 0.733 mmol), 1,2-dichloro-4-iodobenzene (2.00 g, 7.33 mmol), but-3-en-2-ol (0.793 g, 11.0 mmol), tetrabutylammonium chloride, hydrate (2.17 g, 7.33 mmol), and sodium bicarbonate (1.539 g, 18.32 mmol). DMF (5 mL) was added via syringe and the reaction mixture was degassed three times. The mixture was heated at 60° C. overnight. The reaction mixture was allowed to cool to rt, diluted with ether and the organic layer was washed with water. The organic layer was separated, dried with MgSO₄, filtered and concentrated. The crude residue was purified by silica gel chromatography with an eluent of 10% ethyl acetate/hexanes to afford the desired product Intermediate 29A (1.40 g, 6.45 mmol, 88% yield). LC-MS (ESI) m/z 216.9 (M+H), RT=2.01 min (Method B).

Intermediate 29B. (S)-N-((R)-4-(3,4-dichlorophenyl)butan-2-yl)-2-methylpropane-2-sulfinamide

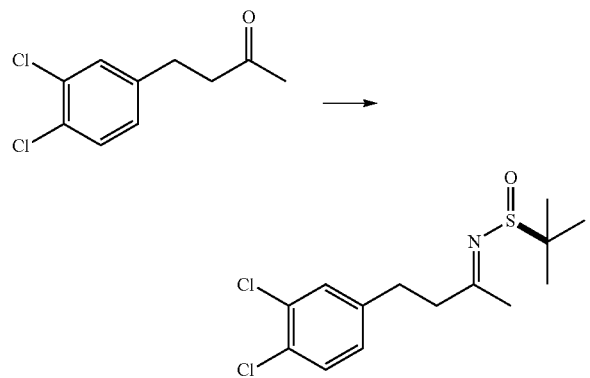

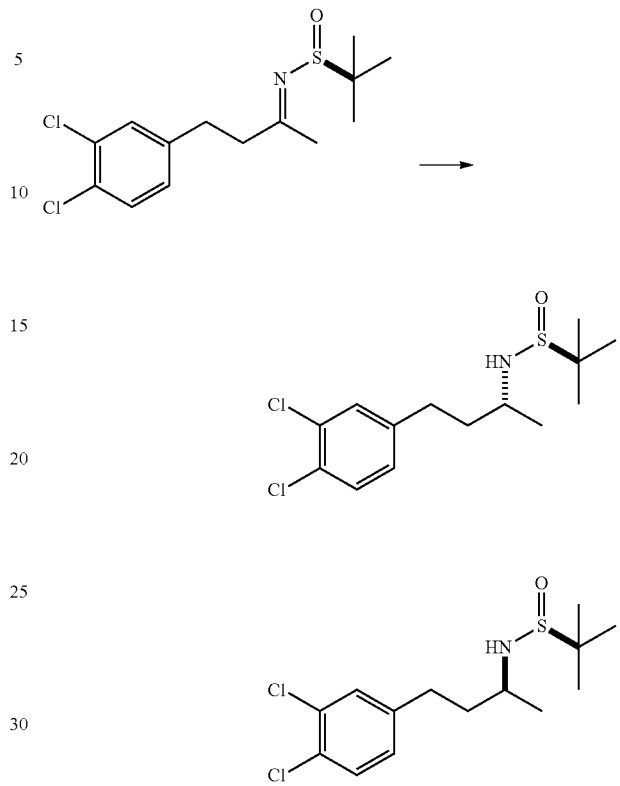

To a stirred solution of (S)-2-methylpropane-2-sulfinamide (373 mg, 3.08 mmol) and 4-(3,4-dichlorophenyl)butan-2-one (700 mg, 3.22 mmol) in THF (2 mL) at rt was added tetraethoxytitanium (1.22 mL, 5.86 mmol). The reaction mixture was heated at 75° C. overnight, and allowed to cool and stay at rt for 72 h. Another equivalent of Ti(OEt)₄ (1.22 mL, 5.86 mmol) and (S)-2-methylpropane-2-sulfinamide (373 mg, 3.08 mmol) were added. The reaction mixture was heated at 75° C. overnight. The THF solution of (S,E)-N-(4-(3,4-dichlorophenyl)butan-2-ylidene)-2-methylpropane-2-sulfinamide (1033 mg, 3.23 mmol) was stirred in a round-bottomed flask under argon at −40 to −50° C. L-Selectride (2016 µL, 2.016 mmol) was added dropwise. The resulting mixture was then warmed up to 0° C. during a 1.5 h period and LC-MS showed the completion of the reaction. It was cooled in dry ice and MeOH was added dropwise until gas evolution stopped. The mixture was stirred at rt for 20 min. It was filtered through Celite® and rinsed with CH₂Cl₂ and the filtrate was washed with brine (2×) and dried over Na₂SO₄, filtered and concentrated. The residue was purified on ISCO flash chromatography (0-100% hexanes/EtOAc) to give (S)-N-((R)-4-(3,4-dichlorophenyl)butan-2-yl)-2-methylpropane-2-sulfinamide (620 mg, 1.924 mmol, 59.6% yield) as slightly tan viscous oil (slow eluent) and an impure (S)-N-((S)-4-(3,4-dichlorophenyl)butan-2-yl)-2-methylpropane-2-sulfinamide. LC-MS (ESI) m/z 322.0 (M+H), RT=2.34 min (Method B).

Intermediate 29

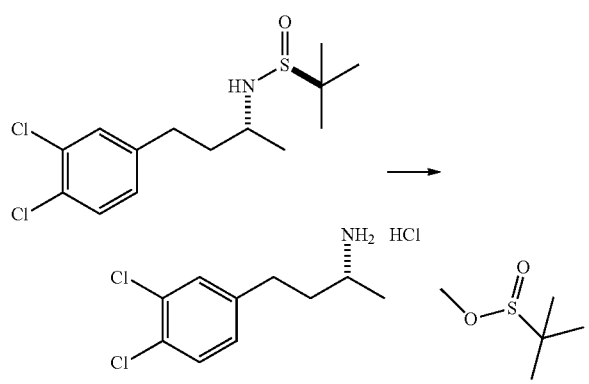

(S)-N-((R)-4-(3,4-Dichlorophenyl)butan-2-yl)-2-methyl-propane-2-sulfinamide (600 mg, 1.862 mmol) was stirred in MeOH (10 mL) at rt. 4N HCl in dioxane (5 mL) was added. The resulting mixture was stirred at rt for 20 min. The solvents were evaporated and $CH_2Cl_2$ (3×) was added and evaporated. The resulting white solids were vacuum dried for 5 h to give (R)-4-(3,4-dichlorophenyl)butan-2-amine hydrochloride (462 mg, 1.815 mmol, 97% yield) as off-white solids and methyl 2-methylpropane-2-sulfinate. The HCl salt was used without further purification. LC-MS (ESI) m/z 218.0 (M+H), RT=1.61 min (Method B).

Intermediate 30. cis-4-phenylcyclohexanamine

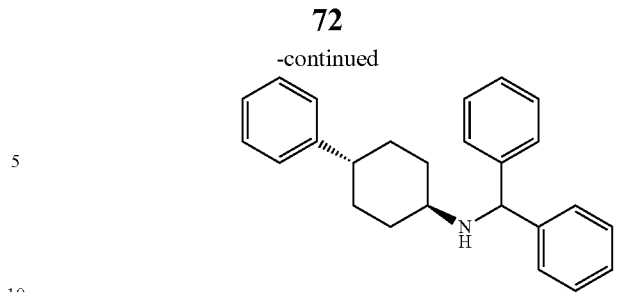

Intermediate 30A.
Cis-N-benzhydryl-4-phenylcyclohexanamine

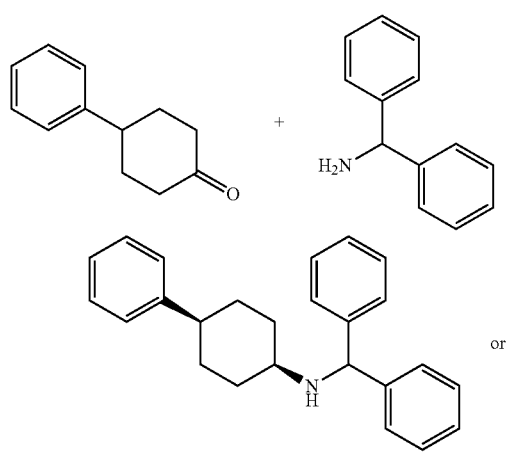

To a solution of 4-phenylcyclohexanone (500 mg, 2.87 mmol) and diphenylmethanamine (526 mg, 2.87 mmol) in DCE (4 mL) at 0° C. was added sodium triacetoxyborohydride (912 mg, 4.30 mmol) by portions slowly. A white suspension resulted and was stirred for 5 min before the ice-water bath was removed. The reaction was stirred at rt for 1.5 h. The reaction was quenched with water carefully, then saturated $NaHCO_3$ was added carefully and the aqueous was extracted with DCM (3×). The organic layers were combined, washed with brine, dried over $Na_2SO_4$, and concentrated. The residue was purified by ISCO flash chromatography (0-100% hexane/EtOAc) to give Intermediate 30A (734 mg, 2.149 mmol, 74.9% yield) and trans-N-benzhydryl-4-phenylcyclohexanamine (191 mg, 0.559 mmol, 19.49% yield), LC-MS (ESI) m/z 342.1 (M+H), RT=1.76 min (Method B). $^1$H NMR (400 MHz, chloroform-d) δ ppm 7.37 (4 H, d, J=7.33 Hz), 7.23-7.31 (6 H, m), 7.11-7.23 (5 H, m), 4.91 (1 H, s), 2.80-2.88 (1 H, m), 2.46-2.56 (1 H, m), 1.74-1.90 (4 H, m), 1.60-1.70 (2H, m), 1.47-1.59 (2 H, m).

Intermediate 30

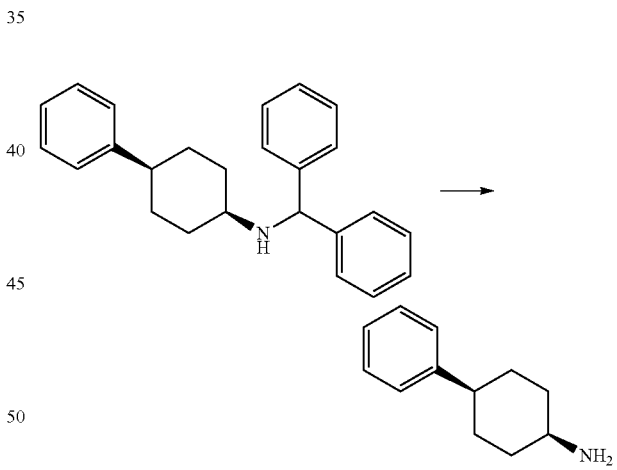

To a solution of Intermediate 30A (714 mg, 2.091 mmol) in MeOH (20 mL) and EtOAc (5 mL) were added 10% palladium on carbon (71.4 mg, 0.067 mmol) and acetic acid (0.120 mL, 2.091 mmol). The reaction was stirred under $H_2$ balloon for 3 h. The reaction mixture was filtered through Celite® and rinsed with EtOAc. The filtrate was concentrated, re-dissolved in DCM, and the organic layer was extracted with 1N HCl. The aqueous layer was made basic with 1N NaOH and extracted with DCM (3×). The combined organic layers were washed with brine, dried over $Na_2SO_4$, decanted, and concentrated to give Intermediate 30 (321 mg, 1.831 mmol, 88% yield) as a colorless wax. LC-MS (ESI) m/z 176.1 (M+H), RT=1.43 min (Method B). $^1$H NMR (400 MHz, DMSO-d) δ ppm 7.24-7.30 (4 H, m), 7.13-7.18 (1 H, m), 3.10-3.16 (1 H, m), 2.42-2.50 (1 H, m), 1.80-1.93 (2 H, m), 1.60-1.66 (4 H, m), 1.44-1.54 (2 H, m).

Intermediate 31.
trans-4-(4-fluorophenyl)-4-methoxycyclohexanamine

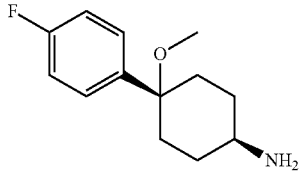

Intermediate 31 (179 mg, 0.802 mmol, 90% yield) was prepared as a white powder following the procedure described for Intermediate 30 by replacing 4-phenylcyclohexanone with 4-(4-fluorophenyl)-4-methoxycyclohexanone. LC-MS (ESI) m/z 224.1 (M+H), RT=1.35 min (Method B). $^1$H NMR (400 MHz, DMSO-$d_6$) δ ppm 7.40-7.47 (2 H, m), 7.12-7.21 (2 H, m), 2.92-3.00 (1 H, m), 2.78-2.83 (3H, m), 2.10-2.19 (2 H, m), 1.71-1.82 (2 H, m), 1.57-1.68 (2 H, m), 1.15-1.28 (2 H, m).

Intermediate 32. (1-(3,4-dichlorophenylsulfonyl)azetidin-3-yl)methanamine

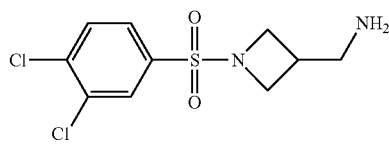 [SMILES: NCC1CN(S(=O)(=O)c2ccc(Cl)c(Cl)c2)C1]

Intermediate 31 (65 mg, 0.22 mmol, 87% yield) was prepared as a white powder following the procedure described for Intermediate 8 by replacing tert-butyl piperidin-4-yl-methylcarbamate with tert-butyl azetidin-3-yl-methylcarbamate. LC-MS (ESI) m/z 295 (M+H)$^+$, RT=1.47 min (Method B).

Intermediate 33 (R)-benzyl 4-(3-(1-aminoethyl)phenyl)piperazine-1-carboxylate

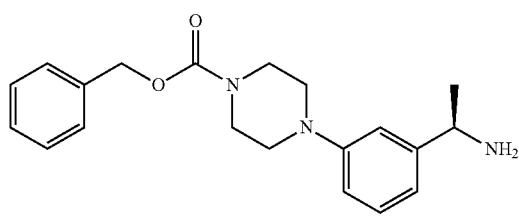 [SMILES: C[C@@H](N)c1cccc(N2CCN(C(=O)OCc3ccccc3)CC2)c1]

Intermediate 33A. (R)-tert-butyl 1-(3-bromophenyl)ethylcarbamate

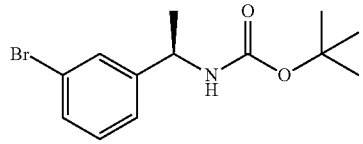 [SMILES: C[C@@H](NC(=O)OC(C)(C)C)c1cccc(Br)c1]

To a solution of (R)-1-(3-bromophenyl)ethanamine (100 mg, 0.500 mmol) in tetrahydrofuran (4 mL) was added Et$_3$N (0.104 mL, 0.750 mmol), followed by di-tert-butyl dicarbonate (131 mg, 0.600 mmol). The reaction mixture was stirred at rt for 3 h. The solvent was removed under reduced pressure. The crude residue was diluted with Et$_2$O and washed with 1N HCl, H$_2$O then dried over Na$_2$SO$_4$. The Et$_2$O layer was concentrated in vacuum to give the crude Intermediate 33A (150 mg, 0.500 mmol, 100% yield). LC-MS (ESI) m/z 245.9 (M−Boc+H), RT=2.13 min (Method B).

Intermediate 33B. (R)-benzyl 4-(3-(1-(tert-butoxycarbonylamino)ethyl)phenyl)piperazine-1-carboxylate

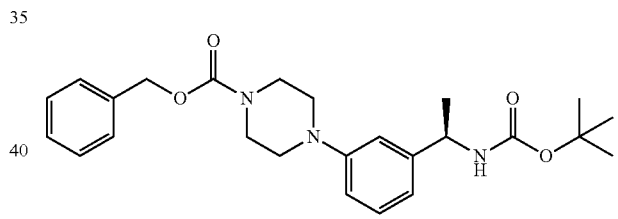

To a suspension of Intermediate 33A (50 mg, 0.167 mmol) and Pd$_2$(dba)$_3$ (15.25 mg, 0.017 mmol) in toluene (2 mL) was added xantphos (28.9 mg, 0.050 mmol), benzyl piperazine-1-carboxylate (36.7 mg, 0.167 mmol), followed by sodium tert-butoxide (48.0 mg, 0.500 mmol). The reaction mixture was stirred at 70° C. for 16 h, and then filtered. The filtrate was concentrated and purified on ISCO using a 15 min gradient from 0 to 100% EtOAc in hexane to give Intermediate 33B (70 mg, 0.159 mmol, 96% yield). LC-MS (ESI) m/z 440.1 (M+H), RT=2.27 min (Method B).

Intermediate 33

To a solution of (R)-benzyl 4-(3-(1-(tert-butoxycarbonylamino)ethyl)phenyl)piperazine-1-carboxylate (35 mg, 0.080 mmol) in DCM (0.2 mL) was added 4 M HCl in dioxanes (100 μL, 0.400 mmol). The reaction mixture was stirred at rt for 2 h. Intermediate 33 (25 mg, 0.074 mmol, 92% yield) was obtained by triturating the crude residue with Et$_2$O. LC-MS (ESI) m/z 340.1 (M+H), RT=1.63 min (Method B).

Intermediate 34. (S)-benzyl 4-(3-(1-aminoethyl)phenyl)piperazine-1-carboxylate

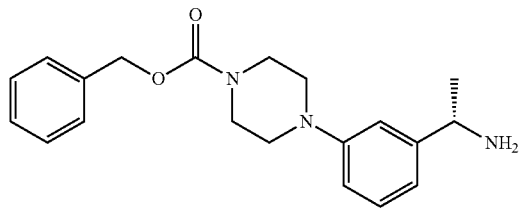 [SMILES: C[C@H](N)c1cccc(N2CCN(C(=O)OCc3ccccc3)CC2)c1]

Intermediate 34 was prepared according to the procedures described in Intermediate 33 using (S)-1-(3-bromophenyl)ethanamine as the starting material. LC-MS (ESI) m/z 340.0 (M+H), RT=1.64 min (Method B).

Example 1

N-(3-(3,4-dichlorophenyl)propyl)-3-hydroxy-1-methyl-2-oxo-1,2-dihydroquinoline-4-carboxamide

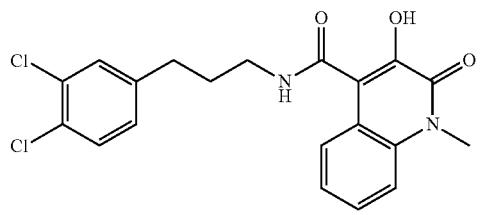 [SMILES: Cn1c(=O)c(O)c(C(=O)NCCCc2ccc(Cl)c(Cl)c2)c2ccccc21]

Example 1A 3-hydroxy-1-methyl-2-oxo-1,2-dihydroquinoline-4-carboxylic acid

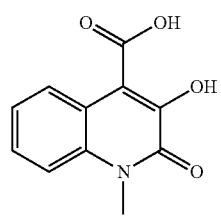 [SMILES: Cn1c(=O)c(O)c(C(=O)O)c2ccccc21]

Ethyl 3-hydroxy-1-methyl-2-oxo-1,2-dihydroquinoline-4-carboxylate (Intermediate 16, 2.10 g, 8.49 mmol) was stirred in NaOH (50 mL, 50 mmol). The mixture was heated at reflux for 2 h. The residue was allowed to cool and acidified with 1N HCl (ca. 50 mL) dropwise through an additional funnel at 0° C. The precipitate was collected by filtration, rinsed with H₂O (2×), and dried to give Example 1A (1.80 g, 8.21 mmol, 97% yield) as a white solid.

Example 1

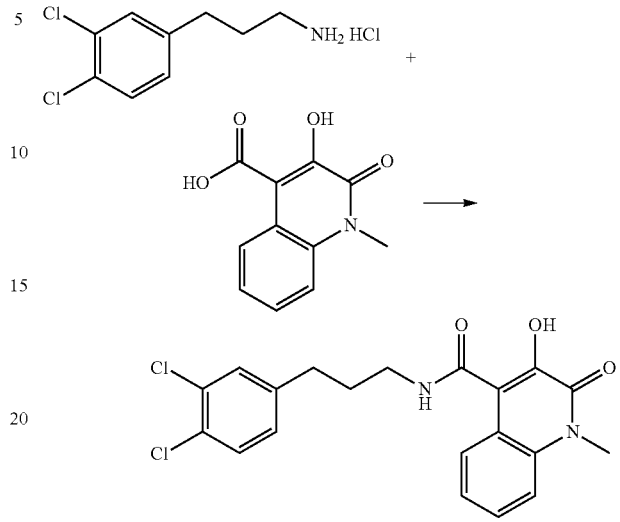

A solution of Example 1A (83 mg, 0.38 mmol) and Intermediate 1 (65 mg, 0.27 mmol) were stirred at rt in DMF (1.5 mL). HOBT (77 mg, 0.50 mmol) and EDC (96 mg, 0.50 mmol) were added followed by the addition of triethylamine (0.215 mL, 1.54 mmol). The mixture was stirred at rt overnight. EtOAc was added and the organic phase was washed with H₂O, brine, and concentrated. The residue was dissolved in MeOH and purified by reverse phase HPLC (MeOH/H₂O/TFA). Example 1 (22 mg, 0.054 mmol, 20% yield) was isolated as a white solid after drying. LC-MS (ESI) m/z 438.8 (M+H), RT=2.22 min (Method B). Orthogonal HPLC RT=10.88 min, 100% (Method A); RT=9.64 min, 98.9% (Method B). $^1$H NMR (400 MHz, acetone) δ ppm 7.76 (1 H, d, J=7.6 Hz), 7.60-7.73 (1 H, m), 7.43-7.59 (4 H, m), 7.23-7.36 (2 H, m), 3.82 (3 H, s), 3.53 (2 H, q, J=6.6 Hz), 2.77-2.93 (2 H, m), 1.91-2.05 (2 H, m).

Example 2

N-(3-(2,4-Dichlorophenyl)propyl)-3-hydroxy-1-methyl-2-oxo-1,2-dihydroquinoline-4-carboxamide

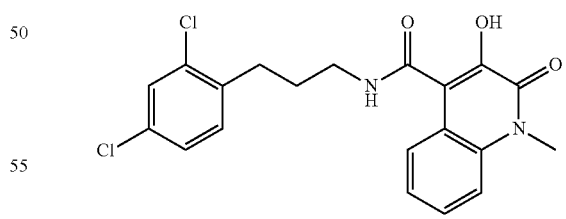

To a solution of Example 1A (67 mg, 0.31 mmol) was added thionyl chloride (66.9 µL, 0.92 mmol). The reaction mixture was stirred at 80° C. for 2 h, allowed to cool and was concentrated under reduced pressure to give the crude 3-hydroxy-1-methyl-2-oxo-1,2-dihydroquinoline-4-carbonyl chloride (62 mg, 0.26 mmol, 85% yield). 3-Hydroxy-1-methyl-2-oxo-1,2-dihydroquinoline-4-carbonyl chloride (0.020 g, 0.084 mmol) was stirred in CH₂Cl₂ (1 mL). Intermediate 2 (0.025 g, 0.084 mmol) was added, followed by the addition of triethylamine (0.035 mL, 0.25 mmol) at 0° C. The mixture was stirred at rt for 1 h, then concentrated under reduced pressure. The residue was dissolved in MeOH and purified by HPLC (MeOH/H$_2$O/TFA). Example 2 (3 mg, 7.40 μmol, 8.8% yield) was isolated as a white solid after drying. LC-MS (ESI) m/z=404.9 (M+H), RT=2.10 min (Method B). Orthogonal RT=9.999 min, 100% (Method A); RT=8.889 min, 100% (Method B). $^1$H NMR (400 MHz, acetone-d$_6$) δ ppm 7.77 (2 H, d, J=6.6 Hz), 7.40-7.60 (4 H, m), 7.12-7.34 (2 H, m), 3.79 (3 H, s), 3.54 (3 H, q), 2.87-3.02 (2 H, m), 1.62-2.00 (2 H, m).

Example 3

6-Chloro-N-(3-(3,4-dichlorophenyl)propyl)-3-hydroxy-1-methyl-2-oxo-1,2-dihydroquinoline-4-carboxamide

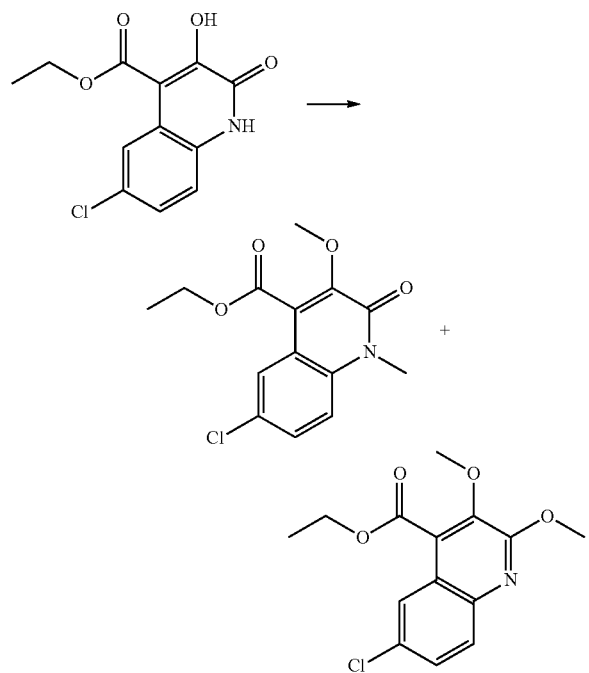

Example 3A ethyl 6-chloro-3-methoxy-1-methyl-2-oxo-1,2-dihydroquinoline-4-carboxylate

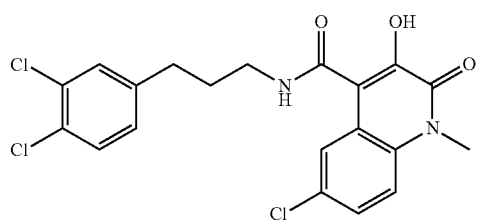 [SMILES: Cn1c(=O)c(O)c(C(=O)NCCCc2ccc(Cl)c(Cl)c2)c2cc(Cl)ccc21]

A solution of ethyl 6-chloro-3-hydroxy-2-oxo-1,2-dihydroquinoline-4-carboxylate (470 mg, 1.76 mmol), prepared following procedure described for Intermediate 16, was stirred in DMF (2 mL) at rt. Cs$_2$CO$_3$ (1430 mg, 4.39 mmol) was added followed by iodomethane (0.220 mL, 3.51 mmol). The resulting mixture was stirred at rt for 72 h. CH$_2$Cl$_2$ was added. The mixture was washed with H$_2$O, brine, dried over MgSO$_4$, filtered and concentrated to give an off-white solid ethyl 6-chloro-3-methoxy-1-methyl-2-oxo-1,2-dihydroquinoline-4-carboxylate (527 mg, 1.78 mmol, 101% yield) as the major product. A small amount of the O-alkylated side product ethyl 6-chloro-2,3-dimethoxyquinoline-4-carboxylate was observed by LC-MS but not isolated (<5%). LC-MS (ESI) 295.9 (M+H), RT=1.97 min (Method B).

Example 3B 6-chloro-3-methoxy-1-methyl-2-oxo-1,2-dihydroquinoline-4-carboxylic acid

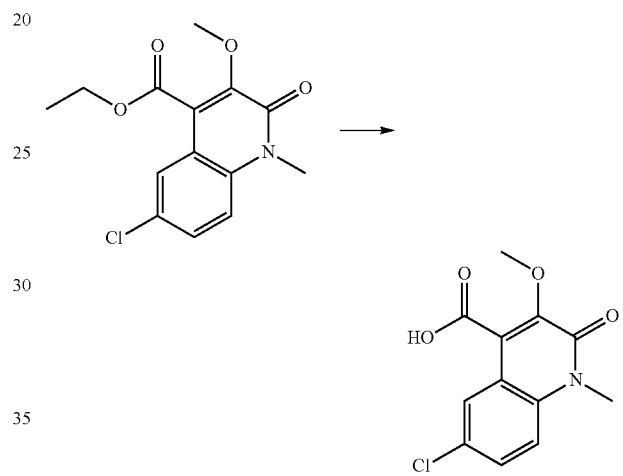

To a solution of Example 3A (400 mg, 1.35 mmol) was stirred in MeOH (20 mL) and water (2 mL) at rt, sodium hydroxide (3.38 mL, 3.38 mmol) was added. The mixture was stirred at rt for 72 h. The mixture was concentrated, and the resulting solution was washed with CH$_2$Cl$_2$. The aqueous layer was acidified with conc. HCl at 0° C., and extracted with CHCl$_3$ (3×). The combined organic layer was washed with brine, dried over MgSO$_4$, filtered and concentrated to give Example 3B (420 mg, 1.57 mmol, 116% yield). LC-MS (ESI) 267.9 (M+H), RT=2.02 (Method A).

Example 3C 6-chloro-N-(3-(3,4-dichlorophenyl)propyl)-3-methoxy-1-methyl-2-oxo-1,2-dihydroquinoline-4-carboxamide

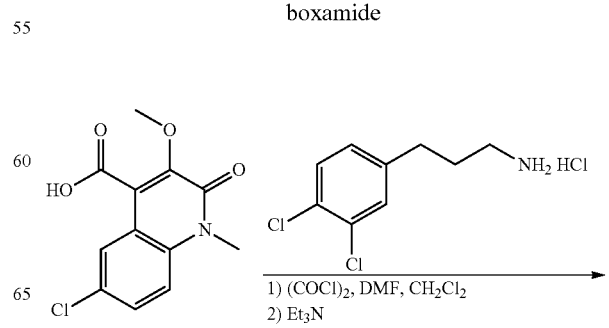

-continued

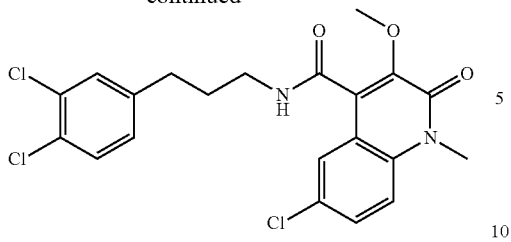

A solution of Example 3B (120 mg, 0.45 mmol) was stirred in CH₂Cl₂ (10 mL) at rt. Oxalyl chloride (21.21 μL, 0.24 mmol) was added dropwise, followed by the addition of DMF (0.330 μL, 4.26 mmol). The resulting mixture was stirred at rt for 4 h. The mixture was concentrated and dried under vacuum to give the acid chloride which was dissolved in CH₂Cl₂ and 3-(3,4-dichlorophenyl) propan-1-amine hydrochloride (Intermediate 1) (53 mg, 0.22 mmol) was added, followed by the addition of triethylamine (46.1 μL, 0.33 mmol). The resulting mixture was stirred for 14 h. EtOAc was added and the organic phase was washed with H₂O, then brine, dried over MgSO₄, filtered and concentrated. Example 3C (65 mg, 0.13 mmol, 59% yield) was obtained by ISCO flash chromatography on silical gel eluting with 0-100% EtOAc/hexane. LC-MS (ESI) 454.8 (M+H), RT=3.61 (Method A). Orthogonal HPLC: RT=10.98 min, 91.4% (Method A); RT=9.69 min, >95% (Method B).

Example 3

To a solution of Example 3C (60 mg, 0.13 mmol) in CH₂Cl₂ (1 mL) at 0° C. under Ar. Tribromoborane (0.198 mL, 0.20 mmol) was added dropwise. The resulting solution was stirred at 0° C. for 1 h. Brine was added and the aqueous phase was extracted with CH₂Cl₂ (2×). The combined organic phase was washed with H₂O, brine, dried over MgSO₄, filtered and concentrated. The residue was dissolved in MeOH and purified by HPLC (MeOH/H₂O/TFA) to yield Example 3 (48 mg, 0.11 mmol, 83% yield) as a white solid. LC-MS (ESI) 440.9 (M+H), RT=1.89 (Method B). Orthogonal HPLC: RT=10.88 min, 100% (Method A); RT=9.63 min, 100% (Method B). ¹H NMR (400 MHz, acetone-d₆) δ ppm 8.30-9.18 (1 H, m), 7.67-7.92 (2 H, m), 7.41-7.60 (4 H, m), 7.29 (1 H, dd, J=8.2, 2.2 Hz), 3.79 (3 H, s), 3.51 (2 H, q, J=6.6 Hz), 2.75-2.86 (2 H, m), 1.88-2.03 (2 H, m).

Example 4

2-(6-chloro-4-(3-(3,4-dichlorophenyl)propylcarbamoyl)-1-methyl-2-oxo-1,2-dihydroquinolin-3-yloxy)acetic acid

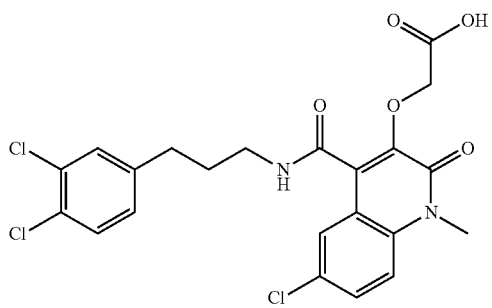 [SMILES: Cn1c(=O)c(OCC(=O)O)c(C(=O)NCCCc2ccc(Cl)c(Cl)c2)c2cc(Cl)ccc21]

Example 4A methyl 2-(6-chloro-4-(3-(3,4-dichlorophenyl)propylcarbamoyl)-1-methyl-2-oxo-1,2-dihydroquinolin-3-yloxy)acetate

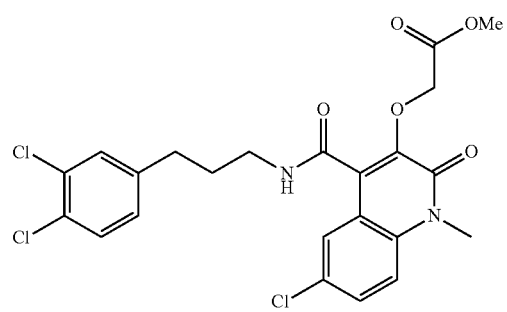 [SMILES: COC(=O)COc1c(C(=O)NCCCc2ccc(Cl)c(Cl)c2)c2cc(Cl)ccc2n(C)c1=O]

To a solution of Example 3 (25 mg, 0.057 mmol) in DMF (0.5 mL) was added Cs₂CO₃ (33.3 mg, 0.10 mmol) followed by methyl 2-bromoacetate (10.44 mg, 0.068 mmol). The resulting mixture was stirred at rt for 2 h. EtOAc was added and the organic phase was washed with H₂O (2×), brine, dried over MgSO₄, filtered and concentrated. The residue was purified by ISCO flash chromatography on silica gel using 0-1005 ethyl acetate and hexane to give Example 4A (22 mg, 0.043 mmol, 76% yield). LC-MS (ESI) 512.9 (M+H), RT=3.73 (Method A). Orthogonal HPLC: RT=11.56 min, 83.6% (Method A); RT=10.16 min, 91.9% (Method B).

Example 4

Example 4A (20 mg, 0.039 mmol) was stirred in MeOH (5 mL). NaOH (0.5 mL, 1.0 M solution, 0.50 mmol) was added. The reaction was heated at 50° C. for 1 h. The reaction mixture was concentrated and the residue was purified by prep HPLC(CH₃CN/H₂O/TFA) to give Example 4 (14 mg, 0.028 mmol, 72% yield) as a white solid. LC-MS (ESI) 498.9 (M+H), RT=3.61 (Method A). Orthogonal HPLC: RT=10.27 min, 100% (Method A); RT=9.27 min, 100% (Method B). ¹H NMR (400 MHz, acetone) δ ppm 8.10-8.18 (1 H, m), 7.71 (2 H, d, J=2.3 Hz), 7.57-7.66 (2 H, m), 7.47-7.52 (2 H, m), 7.28 (1 H, dd, J=8.3, 2.0 Hz), 5.16 (2 H, s), 3.78 (3 H, s), 3.50-3.57 (2H, m), 2.75-2.84 (2H, m), 1.96-2.04 (2 H, m).

Examples 5-61 were prepared according the procedures described for Examples 1-4 by using the appropriate intermediate amines and acids or acid chlorides. The analytical data (retention time, mass and conditions of LC-MS) of Examples 5-61 are listed in the following table.

| Ex. # | Structure | Name | LC-MS [M + 1]/RT | Purity |
|---|---|---|---|---|
| 5 | 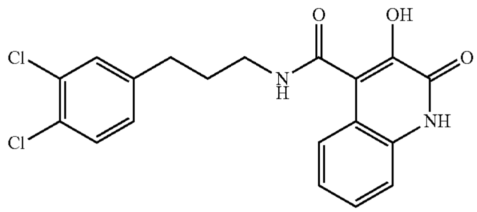 [SMILES: O=C(NCCCc1ccc(Cl)c(Cl)c1)c1c(O)c(=O)[nH]c2ccccc12] | N-(3-(3,4-dichlorophenyl)propyl)-3-hydroxy-2-oxo-1,2-dihydroquinoline-4-carboxamide | 390.1/3.40 min | RT = 8.931 min, 97.3% (Method A) RT = 8.159 min, 97.7% (Method B) |
| 6 | 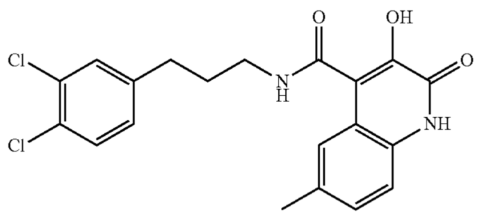 [SMILES: Cc1ccc2[nH]c(=O)c(O)c(C(=O)NCCCc3ccc(Cl)c(Cl)c3)c2c1] | N-(3-(3,4-dichlorophenyl)propyl)-3-hydroxy-6-methyl-2-oxo-1,2-dihydroquinoline-4-carboxamide | 404.9/3.87 min (Method A) | RT = 9.419 min, 97.0% (Method A) RT = 8.52 min, 96.2% (Method B) |
| 7 | 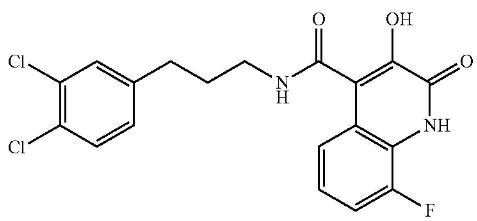 [SMILES: O=C(NCCCc1ccc(Cl)c(Cl)c1)c1c(O)c(=O)[nH]c2c(F)cccc12] | N-(3-(3,4-dichlorophenyl)propyl)-8-fluoro-3-hydroxy-2-oxo-1,2-dihydroquinoline-4-carboxamide | 408.8/2.08 min (Method B) | RT = 9.119 min, 95.8% (Method A) RT = 8.296 min, 98.2% (Method B) |
| 8 | 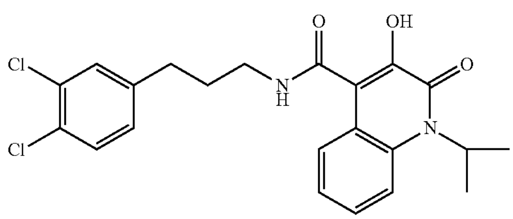 [SMILES: CC(C)n1c(=O)c(O)c(C(=O)NCCCc2ccc(Cl)c(Cl)c2)c2ccccc21] | N-(3-(3,4-dichlorophenyl)propyl)-3-hydroxy-1-isopropyl-2-oxo-1,2-dihydroquinoline-4-carboxamide | 432.8/2.16 min (Method B) | RT = 11.111 min, 92.8% (Method A) RT = 9.848 min, 95.2% (Method B) |
| 9 | 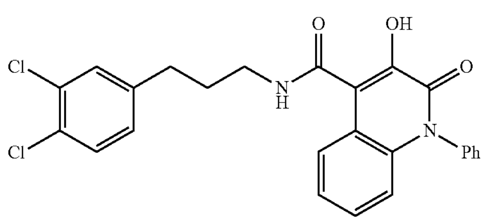 [SMILES: O=C(NCCCc1ccc(Cl)c(Cl)c1)c1c(O)c(=O)n(-c2ccccc2)c2ccccc12] | N-(3-(3,4-dichlorophenyl)propyl)-3-hydroxy-2-oxo-1-phenyl-1,2-dihydroquinoline-4-carboxamide | 466.8, 468.8/2.13 min (Method B) | RT = 11.133 min, 100% (Method A) RT = 9.966 min, 100% (Method B) |
| 10 | 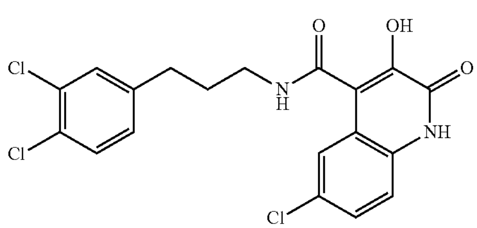 [SMILES: O=C(NCCCc1ccc(Cl)c(Cl)c1)c1c(O)c(=O)[nH]c2ccc(Cl)cc12] | 6-chloro-N-(3-(3,4-dichlorophenyl)propyl)-3-hydroxy-2-oxo-1,2-dihydroquinoline-4-carboxamide | 426.8/4.04 min (Method A) | RT = 9.863 min, 100% (Method A) RT = 8.721 min, 96% (Method B) |
| 11 | 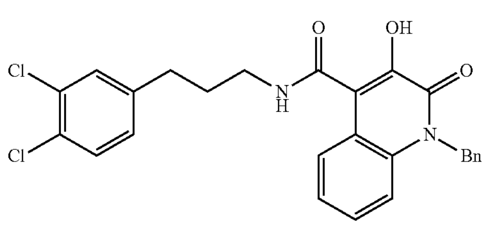 [SMILES: O=C(NCCCc1ccc(Cl)c(Cl)c1)c1c(O)c(=O)n(Cc2ccccc2)c2ccccc12] | 1-benzyl-N-(3-(3,4-dichlorophenyl)propyl)-3-hydroxy-2-oxo-1,2-dihydroquinoline-4-carboxamide | 480.9/4.14 min (Method A) | RT = 11.344 min, 92% (Method A) RT = 10.173 min, 92% (Method B) |

-continued

| Ex. # | Structure | Name | LC-MS [M + 1]/RT | Purity |
|---|---|---|---|---|
| 12 | 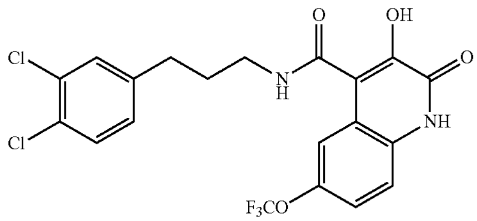 | N-(3-(3,4-dichlorophenyl)propyl)-3-hydroxy-2-oxo-6-(trifluoromethoxy)-1,2-dihydroquinoline-4-carboxamide | 474.9/4.15 min (Method A) | RT = 10.458 min, 100% (Method A) RT = 9.001 min, 100% (Method B) |
| 13 | 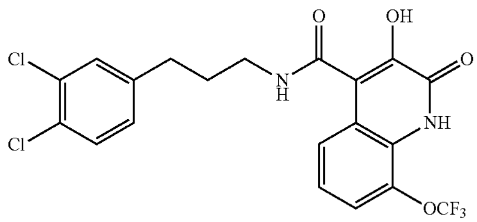 [SMILES: O=C(NCCCc1ccc(Cl)c(Cl)c1)c1c(O)c(=O)[nH]c2c(OC(F)(F)F)cccc12] | N-(3-(3,4-dichlorophenyl)propyl)-3-hydroxy-2-oxo-8-(trifluoromethoxy)-1,2-dihydroquinoline-4-carboxamide | 474.9/4.04 min (Method A) | RT = 10.181 min, 95.4% (Method A) RT = 8.941 min, 95.1% (Method B) |
| 14 | 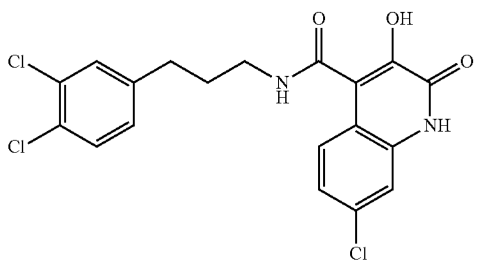 [SMILES: O=C(NCCCc1ccc(Cl)c(Cl)c1)c1c(O)c(=O)[nH]c2cc(Cl)ccc12] | 7-chloro-N-(3-(3,4-dichlorophenyl)propyl)-3-hydroxy-2-oxo-1,2-dihydroquinoline-4-carboxamide | 426.9/4.01 min (Method A) | RT = 9.734 min, 94.1% (Method A) RT = 8.636 min, 95.8% (Method B) |
| 15 | 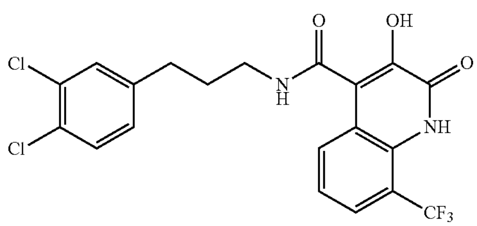 | N-(3-(3,4-dichlorophenyl)propyl)-3-hydroxy-2-oxo-8-(trifluoromethyl)-1,2-dihydroquinoline-4-carboxamide | 459.0/3.99 min (Method A) | RT = 10.059 min, 98.7% (Method A) RT = 8.856 min, 97.9% (Method B) |
| 16 | 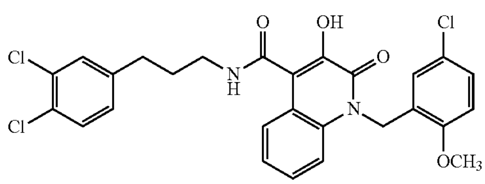 [SMILES: COc1ccc(Cl)cc1Cn1c(=O)c(O)c(C(=O)NCCCc2ccc(Cl)c(Cl)c2)c2ccccc21] | 1-(5-chloro-2-methoxybenzyl)-N-(3-(3,4-dichlorophenyl)propyl)-3-hydroxy-2-oxo-1,2-dihydroquinoline-4-carboxamide | 546.9/4.30 min (Method A) | RT = 12.542 min, 100% (Method A) RT = 11.126 min, 100% (Method B) |
| 17 | 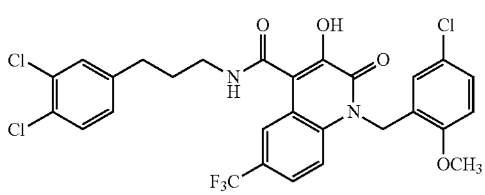 [SMILES: COc1ccc(Cl)cc1Cn1c(=O)c(O)c(C(=O)NCCCc2ccc(Cl)c(Cl)c2)c2cc(C(F)(F)F)ccc21] | 1-(5-chloro-2-methoxybenzyl)-N-(3-(3,4-dichlorophenyl)propyl)-3-hydroxy-2-oxo-6-(trifluoromethyl)-1,2-dihydroquinoline-4-carboxamide | 614.8/2.40 min (Method B) | RT = 8.728 min, 97.5% (Method A) RT = 7.886 min, 97.6% (Method B) |
| 18 | 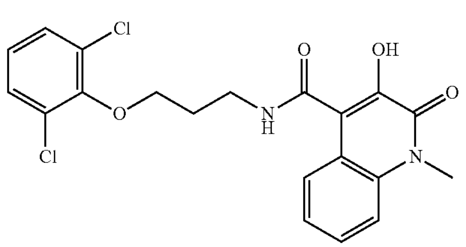 [SMILES: Cn1c(=O)c(O)c(C(=O)NCCCOc2c(Cl)cccc2Cl)c2ccccc21] | N-(3-(2,6-dichlorophenoxy)propyl)-3-hydroxy-1-methyl-2-oxo-1,2-dihydroquinoline-4-carboxamide | 420.8/1.98 min (Method B) | RT = 9.176 min, 98.8% (Method A) RT = 8.359 min, 97.9% (Method B) |

-continued

| Ex. # | Structure | Name | LC-MS [M + 1]/RT | Purity |
|---|---|---|---|---|
| 19 | 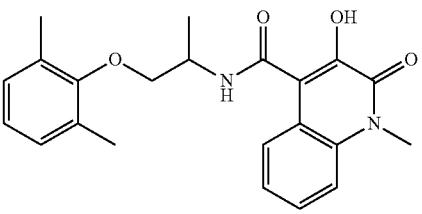 [SMILES: Cc1cccc(C)c1OCC(C)NC(=O)c1c(O)c(=O)n(C)c2ccccc12] | N-(1-(2,6-dimethylphenoxy)propan-2-yl)-3-hydroxy-1-methyl-2-oxo-1,2-dihydroquinoline-4-carboxamide | 381.0/2.01 min (Method B) | RT = 9.334 min, 100% (Method A) RT = 8.388 min, 100% (Method B) |
| 20 | 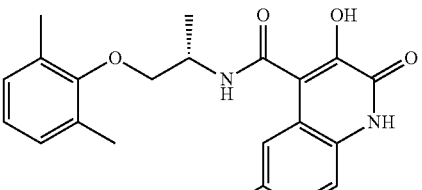 | N-(1-(2,6-dimethylphenoxy)propan-2-yl)-3-hydroxy-2-oxo-6-(trifluoromethoxy)-1,2-dihydroquinoline-4-carboxamide | 451.1/4.00 min (Method A) | RT = 10.104 min, 100% (Method A) RT = 8.751 min, 100% (Method B) |
| 21 | 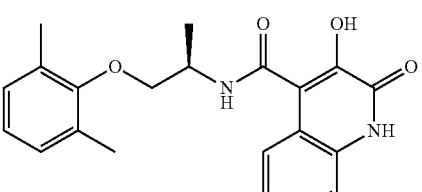 | (R)-N-(1-(2,6-dichlorophenoxy)propan-2-yl)-3-hydroxy-2-oxo-6-(trifluoromethoxy)-1,2-dihydroquinoline-4-carboxamide | 490.9/2.05 min (Method B) | RT = 10.034 min, 100% (Method A) RT = 8.77 min, 100% (Method B) |
| 22 | 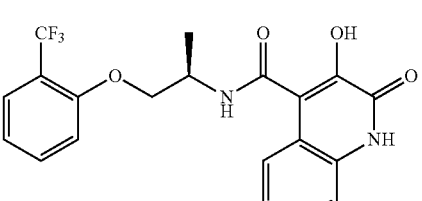 | (R)-3-hydroxy-2-oxo-6-(trifluoromethoxy)-N-(1-(2-(trifluoromethyl)phenoxy)propan-2-yl)-1,2-dihydroquinoline-4-carboxamide | 490.9/2.13 min (Method B) | RT = 9.334 min, 100% (Method A) RT = 8.388 min, 100% (Method B) |
| 23 | 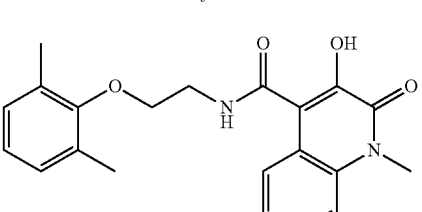 | N-(2-(2,6-dimethylphenoxy)ethyl)-3-hydroxy-1-methyl-2-oxo-1,2-dihydroquinoline-4-carboxamide | 367.0/1.91 min (Method B) | RT = 8.649 min, 98.3 % (Method A) RT = 7.898 min, 98.2% (Method B) |
| 24 | 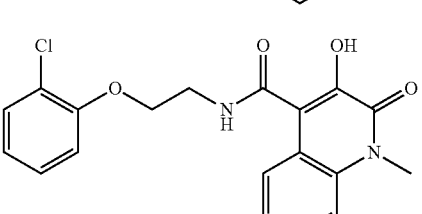 | N-(2-(2-chlorophenoxy)ethyl)-3-hydroxy-1-methyl-2-oxo-1,2-dihydroquinoline-4-carboxamide | 373.0/1.82 min (Method B) | RT = 8.026 min, 97.4% (Method A) RT = 7.511 min, 97.4% (Method B) |
| 25 | 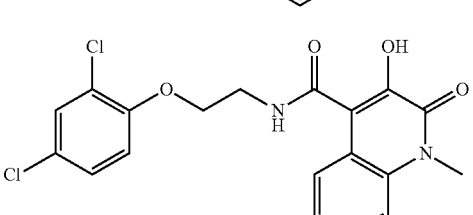 | N-(2-(2,4-dichlorophenoxy)ethyl)-3-hydroxy-1-methyl-2-oxo-1,2-dihydroquinoline-4-carboxamide | 406.9/2.00 min (Method B) | RT = 9.148 min, 100% (Method A) RT = 8.386 min, 100% (Method B) |

-continued

| Ex. # | Structure | Name | LC-MS [M + 1]/RT | Purity |
|---|---|---|---|---|
| 26 | 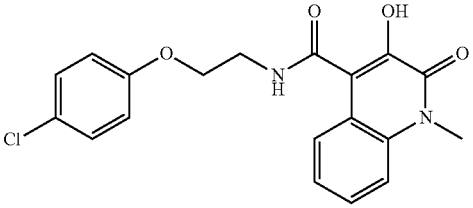 [SMILES: Cn1c(=O)c(O)c(C(=O)NCCOc2ccc(Cl)cc2)c2ccccc21] | N-(2-(4-chlorophenoxy)ethyl)-3-hydroxy-1-methyl-2-oxo-1,2-dihydroquinoline-4-carboxamide | 373.0/1.91 min (Method B) | RT = 8.646 min, 100% (Method A) RT = 7.901 min, 100% (Method B) |
| 27 | 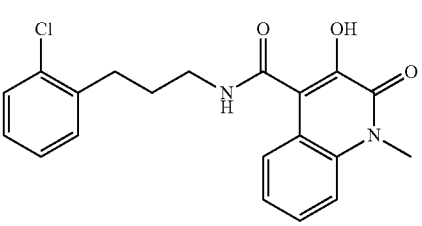 [SMILES: Cn1c(=O)c(O)c(C(=O)NCCCc2ccccc2Cl)c2ccccc21] | N-(3-(2-chlorophenyl)propyl)-3-hydroxy-1-methyl-2-oxo-1,2-dihydroquinoline-4-carboxamide | 371.0/1.94 min (Method B) | RT = 8.858 min, 95.1% (Method A) RT = 8.071 min, 94.5% (Method B) |
| 28 | 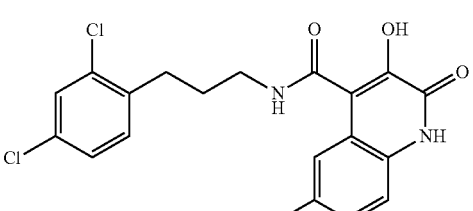 | N-(3-(2,4-dichlorophenyl)propyl)-3-hydroxy-2-oxo-6-(trifluoromethoxy)-1,2-dihydroquinoline-4-carboxamide | 474.9/2.25 min (Method B) | RT = 10.829 min, 100% (Method A) RT = 9.863 min, 100% (Method B) |
| 29 | 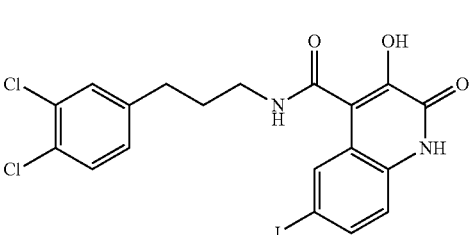 | N-(3-(3,4-dichlorophenyl)propyl)-3-hydroxy-6-iodo-2-oxo-1,2-dihydroquinoline-4-carboxamide | 516.9/2.21 min (Method B) | RT = 10.369 min, 98.9% (Method A) RT = 9.216 min, 98.4% (Method B) |
| 30 | 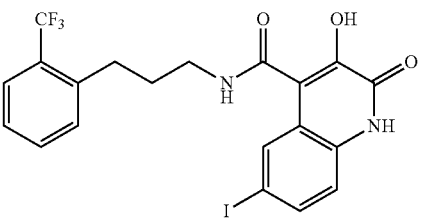 [SMILES: O=C(NCCCc1ccccc1C(F)(F)F)c1c(O)c(=O)[nH]c2ccc(I)cc12] | 3-hydroxy-6-iodo-2-oxo-N-(3-(2-(trifluoromethyl)phenyl)propyl)-1,2-dihydroquinoline-4-carboxamide | 516.9/2.11 min (Method B) | RT = 9.639 min, 100% (Method A) RT = 8.594 min, 100% (Method B) |
| 31 | 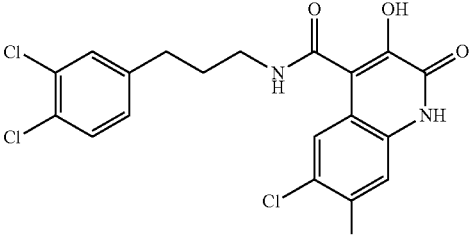 | 6,7-dichloro-N-(3-(3,4-dichlorophenyl)propyl)-3-hydroxy-2-oxo-1,2-dihydroquinoline-4-carboxamide | 460.8/4.15 min (Method A) | RT = 9.80 min, 96.4% (Method A) RT = 8.55 min, 92.7% (Method B) |

-continued

| Ex. # | Structure | Name | LC-MS [M + 1]/RT | Purity |
|---|---|---|---|---|
| 32 | 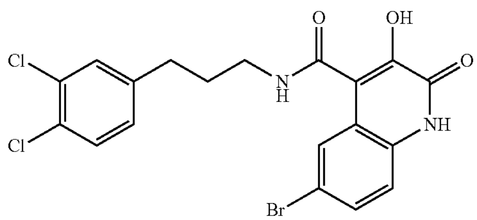 | 6-bromo-N-(3-(3,4-dichlorophenyl)propyl)-3-hydroxy-2-oxo-1,2-dihydroquinoline-4-carboxamide | 470.9/3.95 min (Method A) | RT = 10.31 min, 100% (Method A) RT = 9.12 min, 99.4% (Method B) |
| 33 | 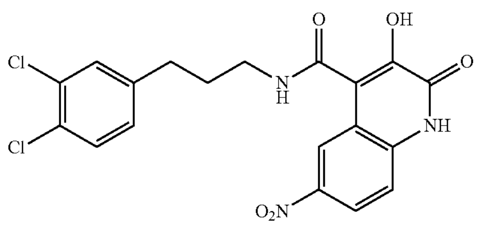 [SMILES: O=C(NCCCc1ccc(Cl)c(Cl)c1)c1c(O)c(=O)[nH]c2ccc([N+](=O)[O-])cc12] | N-(3-(3,4-dichlorophenyl)propyl)-3-hydroxy-6-nitro-2-oxo-1,2-dihydroquinoline-4-carboxamide | 435.9/3.75 min (Method A) | RT = 9.56 min, 100% (Method A) RT = 8.69 min, 88% (Method B) |
| 34 | 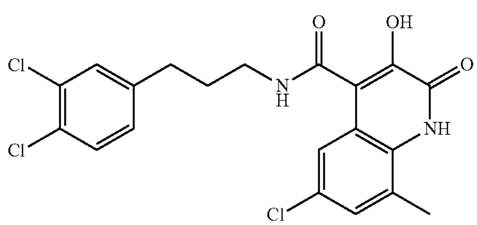 [SMILES: Cc1cc(Cl)cc2c(C(=O)NCCCc3ccc(Cl)c(Cl)c3)c(O)c(=O)[nH]c12] | 6-chloro-N-(3-(3,4-dichlorophenyl)propyl)-3-hydroxy-8-methyl-2-oxo-1,2-dihydroquinoline-4-carboxamide | 440.8/2.15 min (Method B) | RT = 10.71 min, 98.7% (Method A) RT = 9.30 min, 96.4% (Method B) |
| 35 | 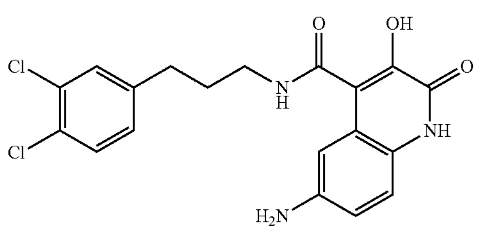 | 6-amino-N-(3-(3,4-dichlorophenyl)propyl)-3-hydroxy-2-oxo-1,2-dihydroquinoline-4-carboxamide | 406.1/2.00 min (Method C) | RT = 5.43 min, 97.8% (Method A) RT = 5.94 min, 100% (Method B) |
| 36 | 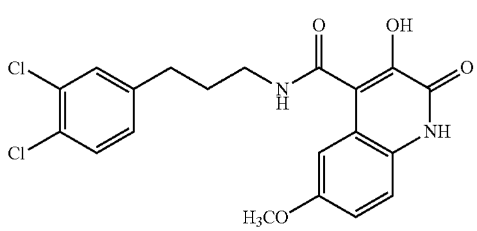 | N-(3-(3,4-dichlorophenyl)propyl)-3-hydroxy-6-methoxy-2-oxo-1,2-dihydroquinoline-4-carboxamide | 420.9/1.98 min (Method B) | {RT = 9.12 min, 94.6% (Method A) RT = 8.38 min, 94.3% (Method B) |
| 37 | 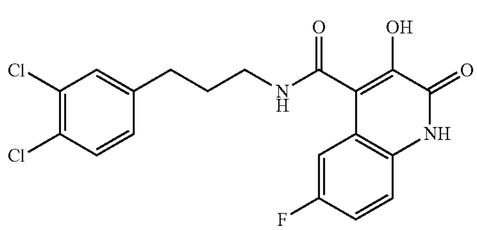 | N-(3-(3,4-dichlorophenyl)propyl)-6-fluoro-3-hydroxy-2-oxo-1,2-dihydroquinoline-4-carboxamide | 409.2/3.74 min (Method B) | RT = 9.55 min, 99.6% (Method A) RT = 8.61 min, 100% (Method B) |

| Ex. # | Structure | Name | LC-MS [M + 1]/RT | Purity |
|---|---|---|---|---|
| 38 | 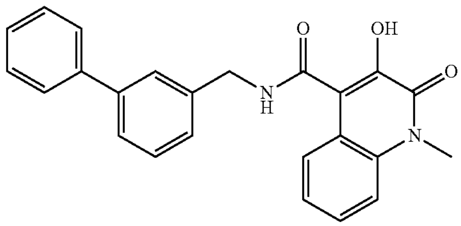 [SMILES: Cn1c(=O)c(O)c(C(=O)NCc2cccc(-c3ccccc3)c2)c2ccccc21] | N-(biphenyl-3-ylmethyl)-3-hydroxy-1-methyl-2-oxo-1,2-dihydroquinoline-4-carboxamide | 385.2/1.57 min (Method D) | RT = 9.46 min, 97.6% (Method A) RT = 8.76 min, 98.2% (Method B) |
| 39 | 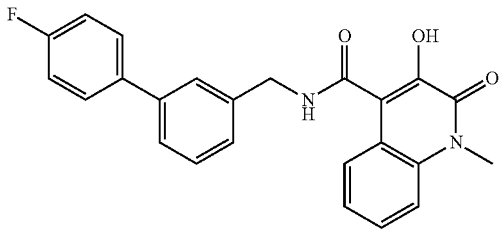 | N-((4'-fluorobiphenyl-3-yl)methyl)-3-hydroxy-1-methyl-2-oxo-1,2-dihydroquinoline-4-carboxamide | 403.2/1.59 min (Method D) | RT = 9.63 min, 97.1% (Method A) RT = 8.89 min, 97.9% (Method B) |
| 40 | 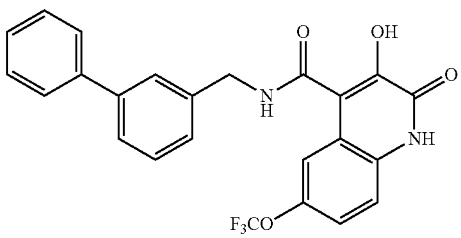 [SMILES: O=C(NCc1cccc(-c2ccccc2)c1)c1c(O)c(=O)[nH]c2ccc(OC(F)(F)F)cc12] | N-(biphenyl-3-ylmethyl)-3-hydroxy-2-oxo-6-(trifluoromethoxy)-1,2-dihydroquinoline-4-carboxamide | 455.0/2.11 min (Method B) | RT = 10.29 min, 93.4% (Method A) RT = 9.20 min, 99.5% (Method B) |
| 41 | 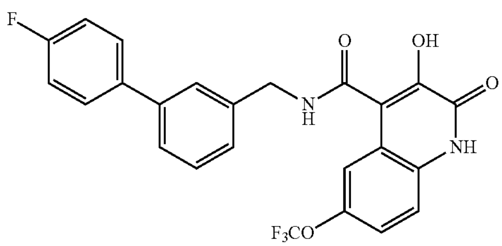 [SMILES: O=C(NCc1cccc(-c2ccc(F)cc2)c1)c1c(O)c(=O)[nH]c2ccc(OC(F)(F)F)cc12] | N-((4'-fluorobiphenyl-3-yl)methyl)-3-hydroxy-2-oxo-6-(trifluoromethoxy)-1,2-dihydroquinoline-4-carboxamide | 473.0/2.12 min (Method B) | RT = 10.35 min, 97.1% (Method A) RT = 9.25 min, 99.7% (Method B) |
| 42 | 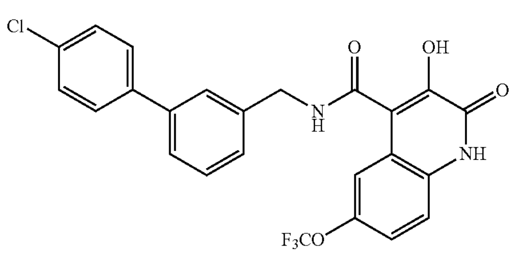 [SMILES: O=C(NCc1cccc(-c2ccc(Cl)cc2)c1)c1c(O)c(=O)[nH]c2ccc(OC(F)(F)F)cc12] | N-((4'-chlorobiphenyl-3-yl)methyl)-3-hydroxy-2-oxo-6-(trifluoromethoxy)-1,2-dihydroquinoline-4-carboxamide | 489.0/2.06 min (Method D) | RT = 11.12 min, 96.1% (Method A) RT = 9.76 min, 92.6% (Method B) |
| 43 | 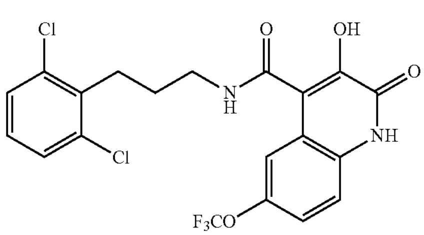 [SMILES: O=C(NCCCc1c(Cl)cccc1Cl)c1c(O)c(=O)[nH]c2ccc(OC(F)(F)F)cc12] | N-(3-(2,6-dichlorophenyl)propyl)-3-hydroxy-2-oxo-6-(trifluoromethoxy)-1,2-dihydroquinoline-4-carboxamide | 474.9/2.34 min (Method B) | RT = 10.47 min, 99.6% (Method A) RT = 9.09 min, 99.8% (Method B) |

| Ex. # | Structure | Name | LC-MS [M + 1]/RT | Purity |
|---|---|---|---|---|
| 44 | 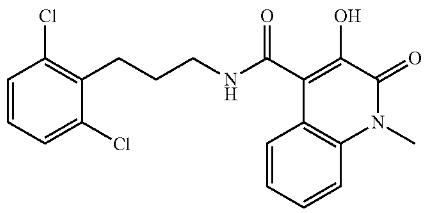 [SMILES: Cn1c(=O)c(O)c(C(=O)NCCCc2c(Cl)cccc2Cl)c2ccccc21] | N-(3-(2,6-dichlorophenyl)propyl)-3-hydroxy-1-methyl-2-oxo-1,2-dihydroquinoline-4-carboxamide | 405.0/2.02 min (Method B) | RT = 9.68 min, 98.7% (Method A) RT = 8.71 min, 99.1% (Method B) |
| 45 | 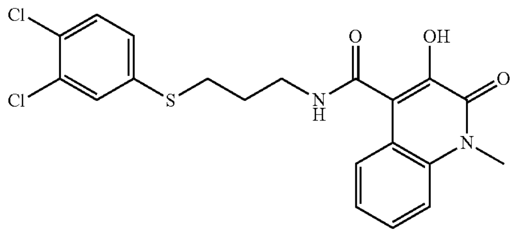 [SMILES: Cn1c(=O)c(O)c(C(=O)NCCCSc2ccc(Cl)c(Cl)c2)c2ccccc21] | N-(3-(3,4-dichlorophenylthio)propyl)-3-hydroxy-1-methyl-2-oxo-1,2-dihydroquinoline-4-carboxamide | 437.1/2.08 min (Method B) | RT = 10.5 min, 99% (Method A) RT = 9.4 min, 98% (Method B) |
| 46 | 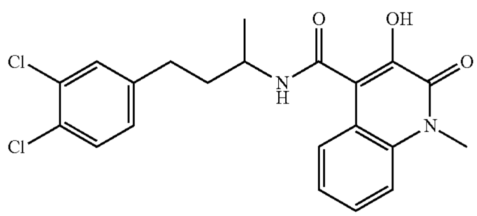 | N-(3-(3,4-dichlorophenylthio)propyl)-3-hydroxy-1-methyl-2-oxo-1,2-dihydroquinoline-4-carboxamide, enantiomer 1 | 420/2.07 min (Method B) | RT = 10.5 min, 98% (Method A) RT = 9.3 min, 97% (Method B) |
| 47 | 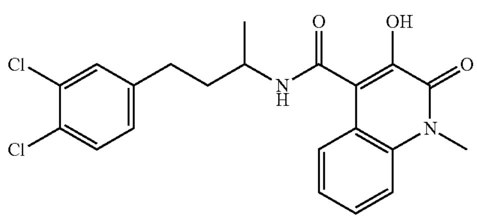 | N-(3-(3,4-dichlorophenylthio)propyl)-3-hydroxy-1-methyl-2-oxo-1,2-dihydroquinoline-4-carboxamide, enantiomer 2 | 420/2.09 min (Method B) | RT = 10.5 min, 99% (Method A) RT = 9.3 min, 97% (Method B) |
| 48 | 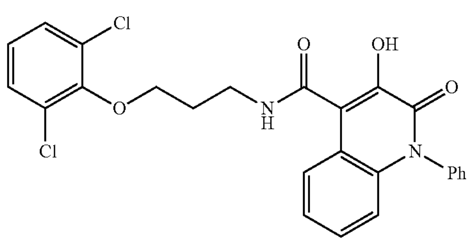 [SMILES: O=C(NCCCOc1c(Cl)cccc1Cl)c1c(O)c(=O)n(-c2ccccc2)c2ccccc12] | N-(3-(2,6-dichlorophenoxy)propyl)-3-hydroxy-2-oxo-1-phenyl-1,2-dihydroquinoline-4-carboxamide | 484.1/2.04 min (Method B) | RT = 10.7 min, 100% (Method A) RT = 9.2 min, 100% (Method B) |
| 49 | 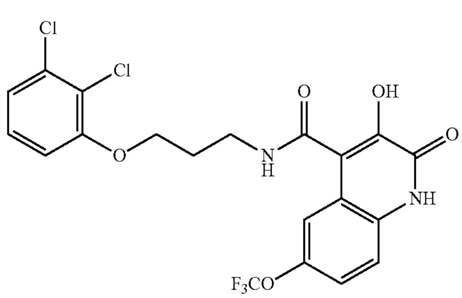 [SMILES: O=C(NCCCOc1cccc(Cl)c1Cl)c1c(O)c(=O)[nH]c2ccc(OC(F)(F)F)cc12] | N-(3-(2,3-dichlorophenoxy)propyl)-3-hydroxy-2-oxo-6-(trifluoromethoxy)-1,2-dihydroquinoline-4-carboxamide | 492.1/2.11 min (Method B) | RT = 10.17 min, 100% (Method A) RT = 8.97 min, 91% (Method B) |

| Ex. # | Structure | Name | LC-MS [M + 1]/RT | Purity |
|---|---|---|---|---|
| 50 | 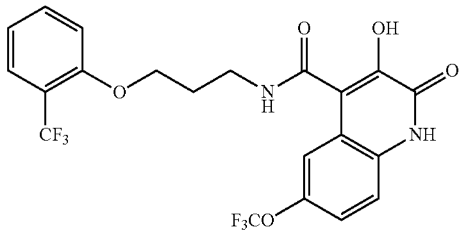 [SMILES: O=C(NCCCOc1ccccc1C(F)(F)F)c1c(O)c(=O)[nH]c2ccc(OC(F)(F)F)cc12] | 3-hydroxy-2-oxo-6-(trifluoromethoxy)-N-(3-(2-(trifluoromethyl)phenoxy)propyl)-1,2-dihydroquinoline-4-carboxamide | 492.1/3.82 min (Method A) | RT = 9.97 min, 100% (Method A) RT = 8.84 min, 100% (Method B) |
| 51 | 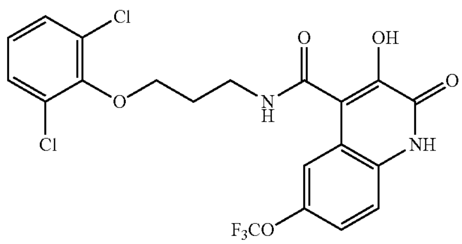 [SMILES: O=C(NCCCOc1c(Cl)cccc1Cl)c1c(O)c(=O)[nH]c2ccc(OC(F)(F)F)cc12] | N-(3-(2,6-dichlorophenoxy)propyl)-3-hydroxy-2-oxo-6-(trifluoromethoxy)-1,2-dihydroquinoline-4-carboxamide | 492.1/3.89 min (Method A) | RT = 10.4 min, 100% (Method A) RT = 9.4 min, 100% (Method B) |
| 52 | 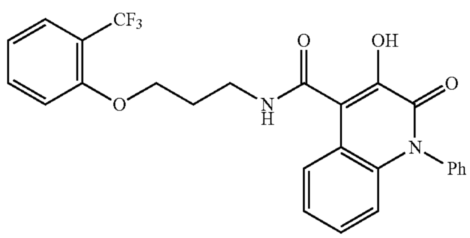 [SMILES: O=C(NCCCOc1ccccc1C(F)(F)F)c1c(O)c(=O)n(-c2ccccc2)c2ccccc12] | 3-hydroxy-2-oxo-1-phenyl-N-(3-(2-(trifluoromethyl)phenoxy)propyl)-1,2-dihydroquinoline-4-carboxamide | 483/2.02 min (Method B) | RT = 10.6 min, 96% (Method A) RT = 9.67 min, 96 % (Method B) |
| 53 | 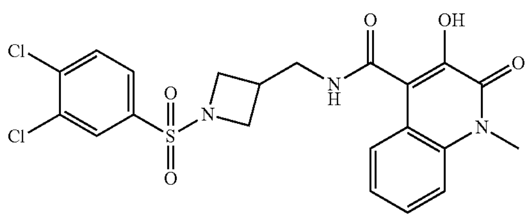 [SMILES: Cn1c(=O)c(O)c(C(=O)NCC2CN(S(=O)(=O)c3ccc(Cl)c(Cl)c3)C2)c2ccccc21] | N-((1-(3,4-dichlorophenylsulfonyl)azetidin-3-yl)methyl)-3-hydroxy-1-methyl-2-oxo-1,2-dihydroquinoline-4-carboxamide | 496/3.4 min (Method A) | RT = 9.03 min, 94% (Method A) RT = 8.42 min, 97.1% (Method B) |
| 54 | 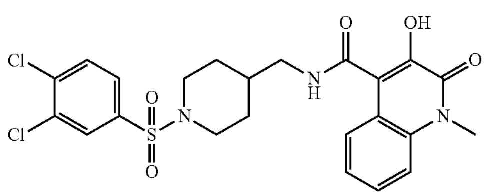 [SMILES: Cn1c(=O)c(O)c(C(=O)NCC2CCN(S(=O)(=O)c3ccc(Cl)c(Cl)c3)CC2)c2ccccc21] | N-((1-(3,4-dichlorophenylsulfonyl)piperidin-4-yl)methyl)-3-hydroxy-1-methyl-2-oxo-1,2-dihydroquinoline-4-carboxamide | 524/3.57 min (Method A) | RT = 9.75 min, 97% (Method A) RT = 9.4 min, 100 % (Method B) |
| 55 | 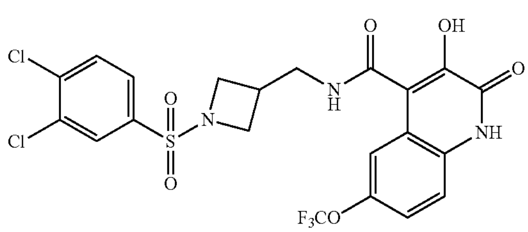 [SMILES: O=C(NCC1CN(S(=O)(=O)c2ccc(Cl)c(Cl)c2)C1)c1c(O)c(=O)[nH]c2ccc(OC(F)(F)F)cc12] | N-((1-(3,4-dichlorophenylsulfonyl)azetidin-3-yl)methyl)-3-hydroxy-2-oxo-6-(trifluoromethoxy)-1,2-dihydroquinoline-4-carboxamide | 565.9/2.03 min (Method B) | RT = 9.7 min, 97% (Method A) RT = 8.8 min, 95% (Method B) |
| 56 | 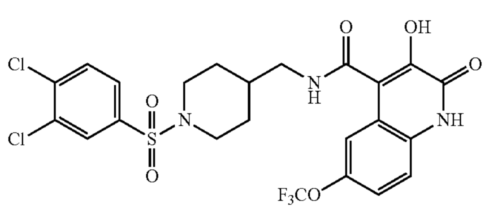 [SMILES: O=C(NCC1CCN(S(=O)(=O)c2ccc(Cl)c(Cl)c2)CC1)c1c(O)c(=O)[nH]c2ccc(OC(F)(F)F)cc12] | N-((1-(3,4-dichlorophenylsulfonyl)piperidin-4-yl)methyl)-3-hydroxy-2-oxo-6-(trifluoromethoxy)-1,2-dihydroquinoline-4-carboxamide | 594.1/3.92 min (Method A) | RT = 10.4 min, 97% (Method A) RT = 9.21 min, 92% (Method B) |

-continued

| Ex. # | Structure | Name | LC-MS [M + 1]/RT | Purity |
|---|---|---|---|---|
| 57 | 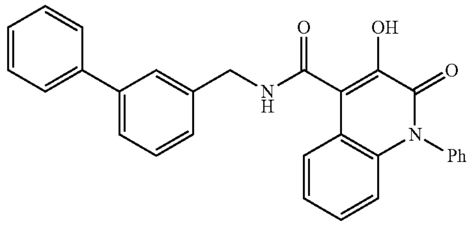 [SMILES: O=C(NCc1cccc(-c2ccccc2)c1)c1c(O)c(=O)n(-c2ccccc2)c2ccccc12] | N-(biphenyl-3-ylmethyl)-3-hydroxy-2-oxo-1-phenyl-1,2-dihydroquinoline-4-carboxamide | 447/2.07 min (Method B) | RT = 10.8 min, 92 % (Method A) RT = 9.97 min, 92 % (Method B) |
| 58 | 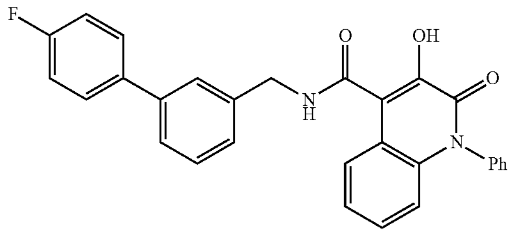 [SMILES: O=C(NCc1cccc(-c2ccc(F)cc2)c1)c1c(O)c(=O)n(-c2ccccc2)c2ccccc12] | N-((4'-fluorobiphenyl-3-yl)methyl)-3-hydroxy-2-oxo-1-phenyl-1,2-dihydroquinoline-4-carboxamide | 465/2.06 min (Method B) | RT = 10.9 min, 92% (Method A) RT = 10.0 min, 92 % (Method B) |
| 59 | 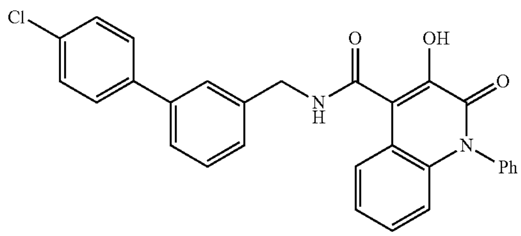 [SMILES: O=C(NCc1cccc(-c2ccc(Cl)cc2)c1)c1c(O)c(=O)n(-c2ccccc2)c2ccccc12] | N-((4'-chlorobiphenyl-3-yl)methyl)-3-hydroxy-2-oxo-1-phenyl-1,2-dihydroquinoline-4-carboxamide | 481.1/2.20 min (Method B) | RT = 11.6 min, 98% (Method A) RT = 10.5 min, 94% (Method B) |
| 60 | 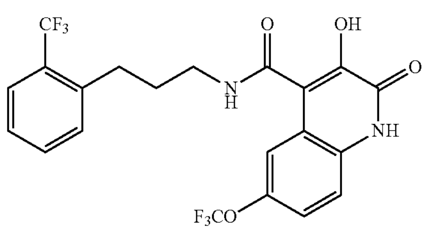 [SMILES: O=C(NCCCc1ccccc1C(F)(F)F)c1c(O)c(=O)[nH]c2ccc(OC(F)(F)F)cc12] | 3-hydroxy-2-oxo-6-(trifluoromethoxy)-N-(3-(2-(trifluoromethyl)phenyl)propyl)-1,2-dihydroquinoline-4-carboxamide | 475/2.22 min (Method A) | RT = 10.1 min, 94% (Method A) RT = 8.8 min, 96% (Method B) |
| 61 | 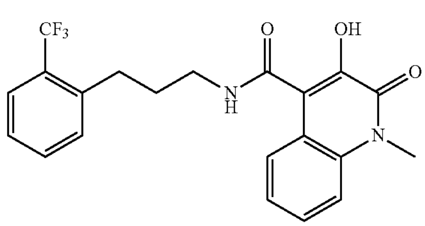 [SMILES: Cn1c(=O)c(O)c(C(=O)NCCCc2ccccc2C(F)(F)F)c2ccccc21] | 3-hydroxy-1-methyl-2-oxo-N-(3-(2-(trifluoromethyl)phenyl)propyl)-1,2-dihydroquinoline-4-carboxamide | 405/3.51 min (Method A) | RT = 9.4 min, 98% (Method A) RT = 8.5 min, 98% (Method B) |

Example 62 (45)

(R)-N-(1-(4'-fluorobiphenyl-3-yl)ethyl)-3-hydroxy-1-methyl-2-oxo-1,2-dihydroquinoline-4-carboxamide

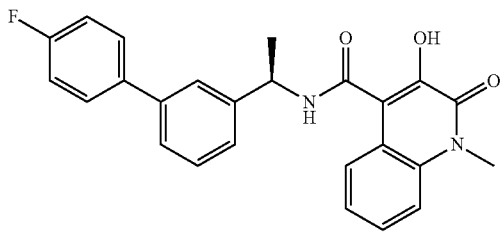 [SMILES: C[C@@H](NC(=O)c1c(O)c(=O)n(C)c2ccccc12)c1cccc(-c2ccc(F)cc2)c1]

Example 62A (45A)

(R)-N-(1-(3-bromophenyl)ethyl)-3-hydroxy-1-methyl-2-oxo-1,2-dihydroquinoline-4-carboxamide

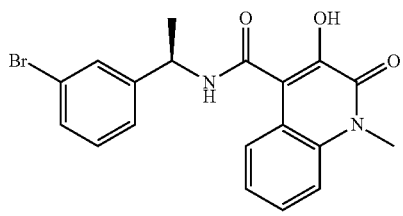 [SMILES: C[C@@H](NC(=O)c1c(O)c(=O)n(C)c2ccccc12)c1cccc(Br)c1]

To a solution of 3-hydroxy-1-methyl-2-oxo-1,2-dihydroquinoline-4-carbonyl chloride (141 mg, 0.593 mmol) in DCM (5 mL) were added TEA (0.25 mL, 1.78 mmol) dropwise at 0° C. and (R)-1-(3-bromophenyl)ethanamine (125 mg, 0.62 mmol) in DCM. The reaction was stirred at rt for 14 h. The reaction was washed with 1N HCl and layers were separated. The aqueous layer was extracted with DCM (2×). The combined organics were washed with brine and dried over Na$_2$SO$_4$ and concentrated. The residue was purified by ISCO flash chromatography on silica gel eluting with 0-10% MeOH in DCM to give Example 62A (159 mg, 0.396 mmol, 67% yield) as a yellow solid.

Example 62

To a solution of Example 62A (50 mg, 0.13 mmol) in DME (1.0 mL) were added 4-fluorophenylboronic acid (34.9 mg, 0.25 mmol), sodium carbonate (0.19 mL, 0.37 mmol), and tetrakis(triphenylphosphine)palladium(0) (29 mg, 0.025 mmol) in a microwave vial. The reaction was degassed and heated at 100° C. for 14 h. The reaction was diluted with DCM, dried over MgSO$_4$, filtered and concentrated. The residue was diluted with MeOH purified by HPLC(CH$_3$CN/H$_2$O/TFA, 30-100% B over 15 min) to give Example 62 (18 mg, 0.043 mmol, 34% yield) as a white solid. LCMS=417.0 [M+1], RT=2.06 min (Method B); Orthogonal HPLC (150×4.6 mm 3.5 µm, 254 nm): Sunfire {RT=9.97 min, 98.6%}; Xbridge {RT=7.50 min, 98.1%). $^1$H NMR (400 MHz, DMSO-d$_6$) δ ppm 9.78 (1 H, br. s.), 9.04 (1 H, d, J=8.08 Hz), 7.74 (1 H, s), 7.61-7.71 (2 H, m), 7.51-7.59 (2 H, m), 7.41-7.51 (5 H, m), 7.32-7.41 (2 H, m), 7.18 (1 H, t, J=7.45 Hz), 5.28 (1 H, qd, J=7.20, 6.95 Hz), 3.74 (3 H, s), 1.49 (3 H, d, J=6.82 Hz).

Example 63

(S)-N-(1-(4'-fluorobiphenyl-3-yl)ethyl)-3-hydroxy-1-methyl-2-oxo-1,2-dihydroquinoline-4-carboxamide

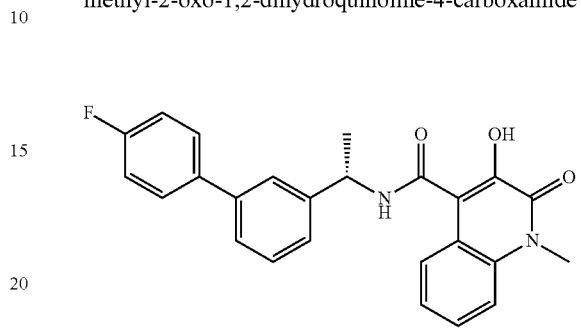

Example 63 was prepared following the procedure described for Example 62 by replacing (R)-1-(3-bromophenyl)ethanamine with (S)-1-(3-bromophenyl)ethanamine LCMS=417.0 [M+1], RT=1.97 min (Method B); Orthogonal HPLC (150×4.6 mm 3.5 µm, 254 nm): Sunfire {RT=10.02 min, 99.7%}; Xbridge {RT=9.18 min, 99.7%). $^1$H NMR (400 MHz, DMSO-d$_6$) δ ppm 9.06 (1H, d, J=8.24 Hz), 7.72 (3 H, dd, J=8.79, 5.50 Hz), 7.50-7.57 (2 H, m), 7.45-7.49 (1 H, m), 7.43 (2 H, d, J=5.50 Hz), 7.33-7.37 (1 H, m), 7.26-7.33 (2 H, m), 7.19 (1 H, t, J=7.15 Hz), 5.27 (1H, qd, J=7.33, 7.15 Hz), 3.74 (3H, s), 1.48 (3 H, d, J=6.60 Hz).

Example 64

(R)-N-(1-(biphenyl-3-yl)ethyl)-3-hydroxy-1-methyl-2-oxo-1,2-dihydroquinoline-4-carboxamide

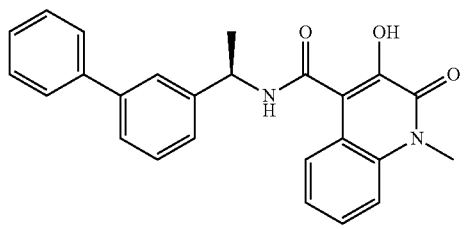 [SMILES: C[C@@H](NC(=O)c1c(O)c(=O)n(C)c2ccccc12)c1cccc(-c2ccccc2)c1]

Example 64 was prepared following the procedure described for Example 62 by replacing 4-fluorophenylboronic acid with phenylboronic acid. LCMS=399.0 [M+1] RT=2.10 min (Method B); Orthogonal HPLC (150×4.6 mm 3.5 µm, 254 nm): Sunfire {RT=9.81 min, 97.2%}; Xbridge {RT=9.90 min, 96.8%). $^1$H NMR (400 MHz, DMSO-d$_6$) δ ppm 9.04 (1 H, d, J=8.08 Hz), 7.74 (1 H, s), 7.61-7.71 (2 H, m), 7.51-7.59 (2 H, m), 7.41-7.51 (5 H, m), 7.32-7.41 (2H, m), 7.18 (1 H, t, J=7.45 Hz), 5.28 (1 H, qd, J=7.20, 6.95 Hz), 3.74 (3 H, s), 1.49 (3 H, d, J=6.82 Hz)

Example 65

N-((4-fluorobiphenyl-3-yl)methyl)-3-hydroxy-1-methyl-2-oxo-1,2-dihydroquinoline-4-carboxamide

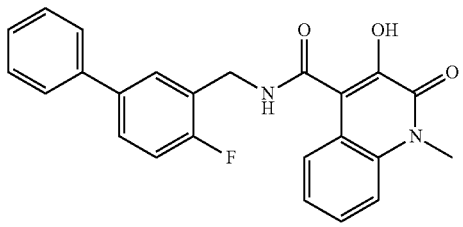 [SMILES: Cn1c(=O)c(O)c(C(=O)NCc2cc(-c3ccccc3)ccc2F)c2ccccc21]

Example 65A

N-(5-bromo-2-fluorobenzyl)-3-hydroxy-1-methyl-2-oxo-1,2-dihydroquinoline-4-carboxamide

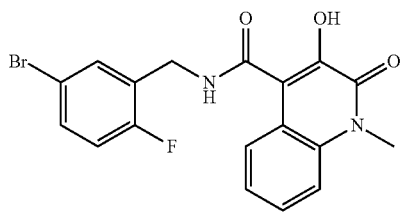 [SMILES: Cn1c(=O)c(O)c(C(=O)NCc2cc(Br)ccc2F)c2ccccc21]

To a solution of 3-hydroxy-1-methyl-2-oxo-1,2-dihydroquinoline-4-carbonyl chloride (150 mg, 0.63 mmol) in DCM (5 mL) were added TEA (0.26 mL, 1.89 mmol) dropwise at 0° C. and (5-bromo-2-fluorophenyl)methanamine (135 mg, 0.66 mmol) in DCM. The reaction was stirred at rt for 14 h. The reaction mixture was washed with 1N HCl and the organic phase was concentrated. The residue was triturated with Et$_2$O and filtered to give Example 65A (217 mg, 0.54 mmol, 85% yield) as a white solid.

Example 65

To a solution of Example 65A (50 mg, 0.12 mmol) in DME (1.0 mL) was added phenylboronic acid (30 mg, 0.25 mmol), 2M sodium carbonate (0.19 mL, 0.37 mmol), and tetrakis(triphenylphosphine)palladium(0) (29 mg, 0.025 mmol) in a microwave vial. The reaction was degassed with argon and heated at 100° C. for 14 h. The cooled reaction mixture was diluted with DCM, dried over MgSO$_4$, filtered and concentrated. The residue was diluted with MeOH purification by HPLC (ACN/H$_2$O/TFA, 5-90% B over 15 min) to give Example 65 (5 mg, 0.012 mmol, 10% yield) as a white solid. LCMS=403.0 [M+1] RT=1.92 min (Method B); Orthogonal HPLC (150×4.6 mm 3.5 μm, 254 nm): Sunfire {RT=9.72 min, 100%}; Xbridge {RT=8.98 min, 100%}. $^1$H NMR (400 MHz, acetone-d$_6$) δ ppm 7.98 (1H, dd, J=7.15, 2.20 Hz), 7.77 (1 H, d, J=7.15 Hz), 7.67 (2 H, d, J=7.70 Hz), 7.59-7.65 (1 H, m), 7.52-7.57 (1 H, m), 7.50 (1 H, d, J=8.24 Hz), 7.45 (2 H, t, J=7.70 Hz), 7.32-7.38 (1 H, m), 7.20-7.29 (2 H, m), 4.83 (2 H, d), 3.80 (3 H, s).

Example 66

N-((4,4'-Difluorobiphenyl-3-yl)methyl)-3-hydroxy-1-methyl-2-oxo-1,2-dihydroquinoline-4-carboxamide

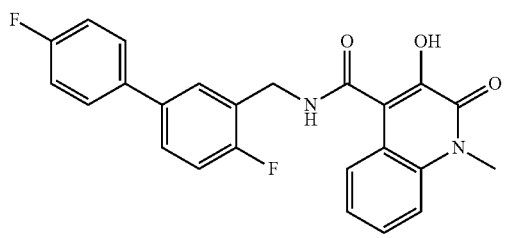 [SMILES: Cn1c(=O)c(O)c(C(=O)NCc2cc(-c3ccc(F)cc3)ccc2F)c2ccccc21]

Example 66 was prepared following the procedure described for Example 65 by replacing phenylboronic acid with 4-fluorophenylboronic acid. LCMS=421.0 [M+1] RT=1.94 min (Method B); Orthogonal HPLC (150×4.6 mm 3.5 μm, 254 nm): Sunfire {RT=9.89 min, 100%}; Xbridge {RT=9.12 min, 100%}. $^1$H NMR (400 MHz, acetone-d$_6$) δ ppm 7.95 (1 H, dd, J=7.15, 2.20 Hz), 7.75 (1 H, d, J=8.24 Hz), 7.66-7.73 (2 H, m), 7.56-7.62 (1 H, m), 7.51-7.55 (1 H, m), 7.46-7.51 (1 H, m), 7.25-7.30 (1 H, m), 7.22-7.25 (1 H, m), 7.17-7.22 (2 H, m), 4.81 (2 H, d), 3.79 (3 H, s)

Example 67

3-hydroxy-1-isobutyl-2-oxo-N-(3-(2-(trifluoromethyl)phenoxy)propyl)-1,2-dihydroquinoline-4-carboxamide

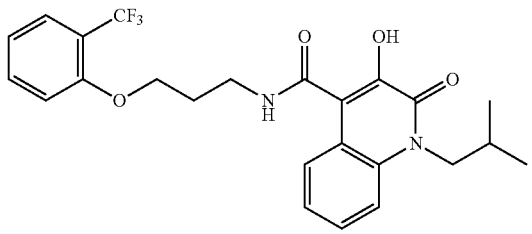 [SMILES: CC(C)Cn1c(=O)c(O)c(C(=O)NCCCOc2ccccc2C(F)(F)F)c2ccccc21]

Example 67A 3-isobutoxy-1-isobutyl-2-oxo-N-(3-(2-(trifluoromethyl)phenoxy)propyl)-1,2-dihydroquinoline-4-carboxamide

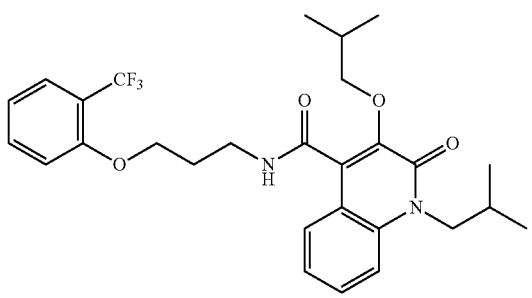 [SMILES: CC(C)COc1c(C(=O)NCCCOc2ccccc2C(F)(F)F)c2ccccc2n(CC(C)C)c1=O]

To a solution of 3-isobutoxy-1-isobutyl-2-oxo-1,2-dihydroquinoline-4-carbonyl chloride (30 mg, 0.089 mmol, made from Intermediate 26 following the procedure described for Example 3) in DCM (1 mL) were added 3-(2-(trifluoromethyl)phenoxy)propan-1-amine (18 mg, 0.081 mmol, Intermediate 10) and Et$_3$N (0.017 mL, 0.12 mmol). The reaction mixture was stirred at rt for 3 h. The reaction mixture was quenched with H$_2$O and concentrated under reduced pressure. Example 67A (25 mg, 0.048 mmol, 59% yield) was purified by HPLC using a 10 min gradient from 10 to 100% B. (Column: PHENOMENEX® Luna Axia 100×20 mm 5 μm (10 min gradient); Solvent A: 10% ACN-90% H$_2$O—0.1% TFA; Solvent B: 90% ACN—10% H$_2$O—0.1% TFA). LCMS=2.22 min; (M+H)$^+$=519 (Method B).

Example 67

To a solution Example 67A (39 mg, 0.075 mmol) in DCM (1 mL) was added boron trichloride-methyl sulfide complex (81 mg, 0.45 mmol). The reaction mixture was stirred at 70° C. for 2 h. Example 67 (15 mg, 0.032 mmol, 43% yield) was purified by HPLC (using a 10 min gradient from 0 to 100% B. Column: PHENOMENEX® Luna Axia 100×20 mm 5 μm (10 min gradient); Solvent A: 10% ACN—90% H$_2$O—0.1% TFA; Solvent B: 90% ACN—10% H$_2$O—0.1% TFA). LCMS=2.07 min [M+1]=463 (Method B); Orthogonal HPLC (150×4.6 mm 3.5 μm, 254 nm): Sunfire {RT=10 min 96%}; Xbridge {RT=8.9 min, 99%}. $^1$H NMR (400 MHz, chloroform-d) δ ppm 8.02 (1H, dd, J=8.1, 1.3 Hz), 7.42-7.56 (3H, m), 7.34-7.37 (1H, m), 7.25-7.30 (1 H, m), 6.99-7.07 (2 H, m), 6.72 (1 H, br. s.), 4.26 (4 H, t, J=5.7 Hz), 3.80 (2 H, q, J=6.1 Hz), 2.21-2.34 (3H, m), 1.01 (6 H, d, J=6.8 Hz).

Examples 68-72 were prepared according the procedures described for Example 67 by using the appropriate intermediate amines and acids or acid chlorides.

| Ex. # | Structure | Name | LC-MS [M + 1]/RT | Purity |
|---|---|---|---|---|
| 68 | 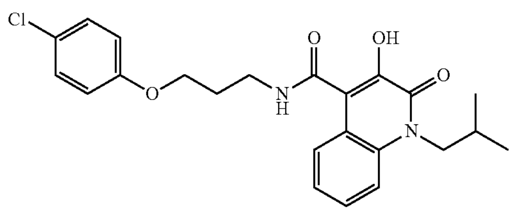 [SMILES: CC(C)Cn1c(=O)c(O)c(C(=O)NCCCOc2ccc(Cl)cc2)c2ccccc21] | N-(3-(4-chlorophenoxy)propyl)-3-hydroxy-1-isobutyl-2-oxo-1,2-dihydroquinoline-4-carboxamide | 429/2.08 min (Method B) | RT = 11.3 min, 99% (Method A) RT = 97.8 min, 99% (Method B) |
| 69 | 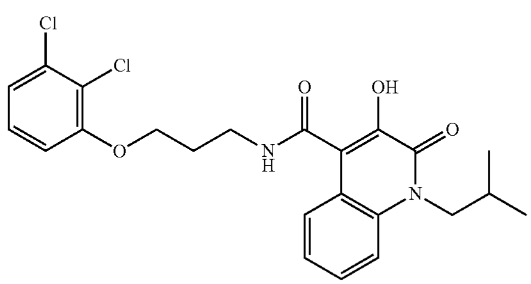 [SMILES: CC(C)Cn1c(=O)c(O)c(C(=O)NCCCOc2cccc(Cl)c2Cl)c2ccccc21] | N-(3-(2,3-dichlorophenoxy)propyl)-3-hydroxy-1-isobutyl-2-oxo-1,2-dihydroquinoline-4-carboxamide | 464/ = 2.14 min (Method B) | RT = 10.8 min, 99% (Method A) RT = 9.7 min, 99% (Method B) |
| 70 | 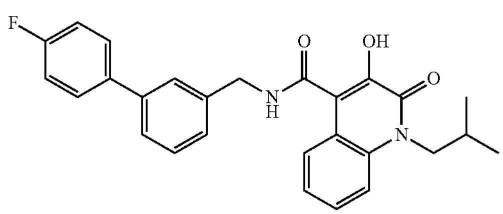 [SMILES: CC(C)Cn1c(=O)c(O)c(C(=O)NCc2cccc(-c3ccc(F)cc3)c2)c2ccccc21] | N-((4'-fluorobiphenyl-3-yl)methyl)-3-hydroxy-1-isobutyl-2-oxo-1,2-dihydroquinoline-4-carboxamide | 445.1/2.13 min (Method B) | RT = 11.2 min, 97.4% (Method A) RT = 10.1 min, 96.8% (Method B) |
| 71 | 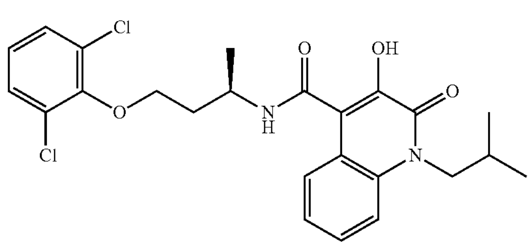 [SMILES: CC(C)Cn1c(=O)c(O)c(C(=O)N[C@H](C)CCOc2c(Cl)cccc2Cl)c2ccccc21] | C(R)-N-(4-(2,6-dichlorophenoxy)butan-2-yl)-3-hydroxy-1-isobutyl-2-oxo-1,2-dihydroquinoline-4-carboxamide | 477/2.14 min (Method B) | RT = 11.2 min, 97.4% (Method A) RT = 10.1 min, 96.8% (Method B) |

| Ex. # | Structure | Name | LC-MS [M + 1]/RT | Purity |
|---|---|---|---|---|
| 72 | 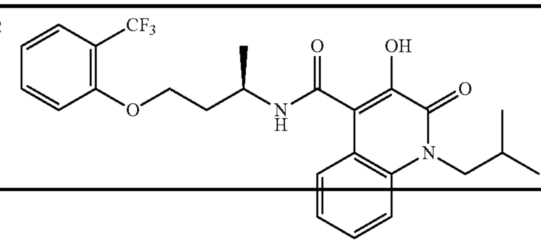 | (R)-3-hydroxy-1-isobutyl-2-oxo-N-(4-(2-(trifluoromethyl)phenoxy)butan-2-yl)-1,2-dihydroquinoline-4-carboxamide | 476.1/2.10 min (Method B) | RT = 11.3 min, 97.4% (Method A) RT = 9.9 min, 98.6% (Method B) |

Example 73

1-(4-bromophenyl)-N-(3-(3,4-dichlorophenyl)propyl)-3-hydroxy-2-oxo-1,2-dihydroquinoline-4-carboxamide

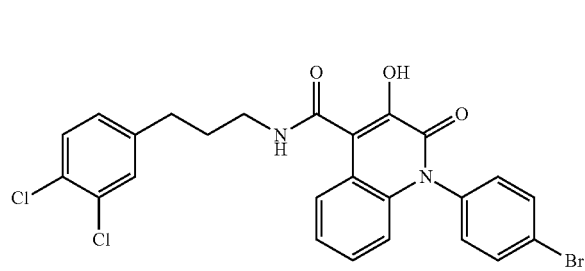 [SMILES: O=C(NCCCc1ccc(Cl)c(Cl)c1)c1c(O)c(=O)n(-c2ccc(Br)cc2)c2ccccc12]

Example 73A 1-(4-bromophenyl)indoline-2,3-dione

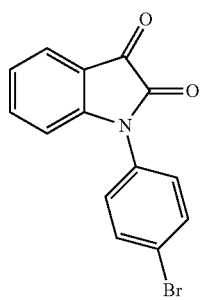 [SMILES: O=C1C(=O)N(c2ccc(Br)cc2)c2ccccc21]

In a 250-mL round bottomed flask attached with a drying tube, was charged with indoline-2,3-dione (0.5 g, 3.40 mmol), 4-bromophenylboronic acid (1.365 g, 6.80 mmol), molecular sieves (ca. 250 mg), copper(II) acetate (0.76 g, 4.18 mmol). CH$_2$Cl$_2$ (15 mL) was added followed by the addition of pyridine (0.687 mL, 8.50 mmol) to the vigorously stirred solution. The mixture was stirred at rt for 2 days, filtered through Celite® and rinsed with CH$_2$Cl$_2$ (2×). The filtrate was washed with H$_2$O (2×), brine (2×), dried (MgSO$_4$), filtered, and concentrated. The residue was dissolved in a small amount of CH$_2$Cl$_2$, and purified by ISCO flash column chromatography (hexanes, then CH$_2$Cl$_2$) to give Example 73A (0.78 g, 2.58 mmol, 76% yield) as reddish yellow solids. LC-MS (ESI) 303.9 (M+H), RT=1.92 min (Method B).

Example 73B ethyl 1-(4-bromophenyl)-3-hydroxy-2-oxo-1,2-dihydroquinoline-4-carboxylate

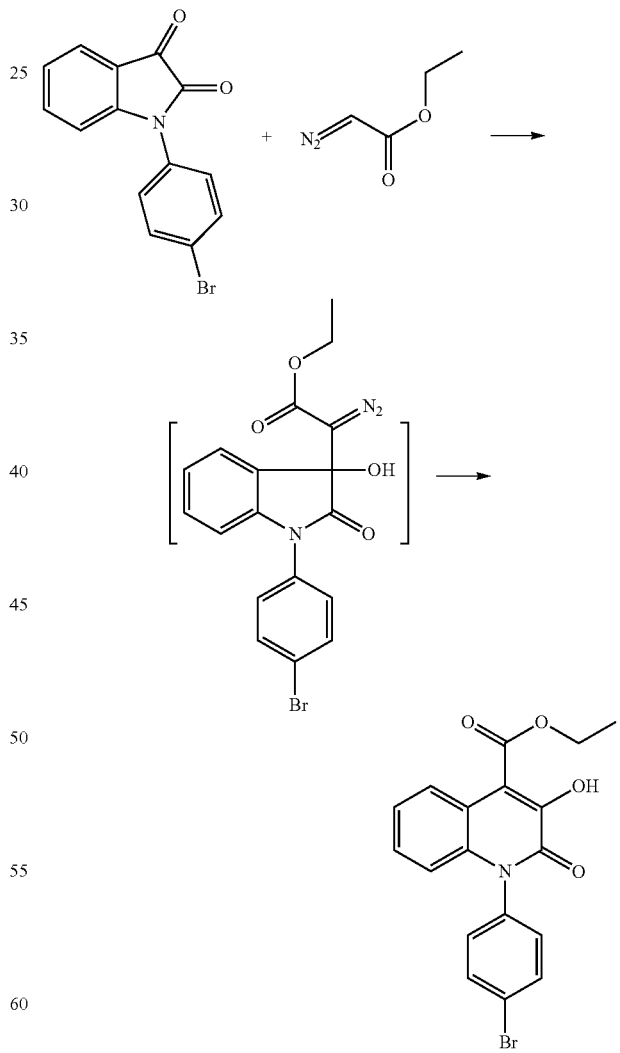

Example 73A (780 mg, 2.58 mmol) was stirred in DMF (3 mL) and ethanol (12 mL) at 0° C. Diethylamine (0.539 mL, 5.16 mmol) was added followed by the addition of ethyl 2-diazoacetate (0.536 mL, 5.16 mmol). The ice bath was removed and the mixture was stirred at rt overnight. The mixture was evaporated to remove most of solvents. 1N HCl (ca. 10 mL) was added to the residue and the resulting slurry was stirred at rt for 2 h. The precipitate was collected by filtration and the solid was rinsed with H₂O (2×) to give Example 73B (0.84 g, 2.164 mmol, 84% yield) as a tan solids.

Example 73C 1-(4-bromophenyl)-3-hydroxy-2-oxo-1,2-dihydro-quinoline-4-carboxylic acid

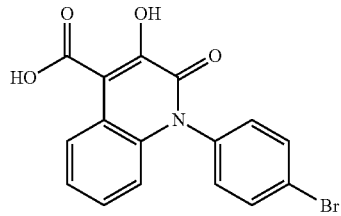 [SMILES: O=C(O)c1c(O)c(=O)n(-c2ccc(Br)cc2)c2ccccc12]

Example 73C was prepared as a white powder following the procedure described for Example 2A by replacing ethyl 3-hydroxy-1-methyl-2-oxo-1,2-dihydroquinoline-4-carboxylate with ethyl 1-(4-bromophenyl)-3-hydroxy-2-oxo-1,2-dihydroquinoline-4-carboxylate. LC-MS (ESI) 361.0 (M+H), RT=1.82 min (Method B).

Example 73D 1-(4-bromophenyl)-3-hydroxy-2-oxo-1,2-dihydro-quinoline-4-carbonyl chloride

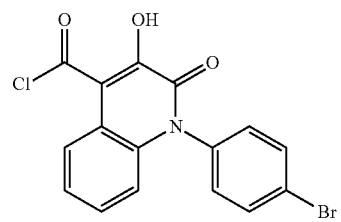 [SMILES: O=C(Cl)c1c(O)c(=O)n(-c2ccc(Br)cc2)c2ccccc12]

Example 73D was prepared following the procedure described for Example 3A.

Example 73

Example 73D (134 mg, 0.35 mmol) was stirred in CH₂Cl₂ (2 mL) at rt. 3-(3,4-dichlorophenyl)propan-1-amine hydrochloride (80 mg, 0.33 mmol) was added, followed by the addition of triethylamine (0.15 mL, 1.06 mmol) at 0° C. The mixture was stirred at rt overnight, then concentrated and the residue was dissolved in MeOH and purified by HPLC (MeOH/H₂O/TFA) to give Example 73 (140 mg, 0.256 mmol, 72% yield). LCMS=546.9 [M+1], RT=2.29 min (Method B); Orthogonal HPLC (150×4.6 mm 3.5 µm, 254 nm): Sunfire {RT=12.034 min, 100%}; Xbridge {RT=10.804 min, 100%}. ¹H NMR (400 MHz, acetone) δ ppm 7.85 (2H, d, J=8.6 Hz), 7.75 (1 H, dd, J=7.5, 1.4 Hz), 7.52 (1 H, d, J=1.5 Hz), 7.48 (1 H, d, J=8.1 Hz), 7.38 (2H, d, J=8.6 Hz), 7.25-7.32 (3 H, m), 6.65-6.68 (1 H, m), 3.55 (2 H, q, J=6.4 Hz), 2.82-2.88 (2 H, m), 1.96-2.01 (2 H, m).

Example 74

(R)-3-hydroxy-1-methyl-2-oxo-N-(1-(3-(piperazin-1-yl)phenyl)ethyl)-1,2-dihydroquinoline-4-carboxamide

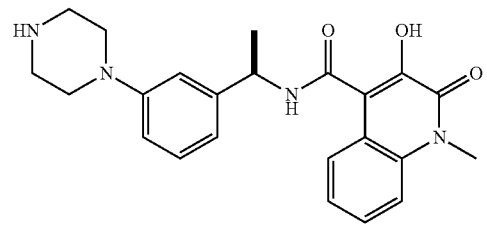 [SMILES: C[C@@H](NC(=O)c1c(O)c(=O)n(C)c2ccccc12)c1cccc(N2CCNCC2)c1]

Example 74A (R)-N-(1-(3-bromophenyl)ethyl)-3-methoxy-1-methyl-2-oxo-1,2-dihydroquinoline-4-carboxamide

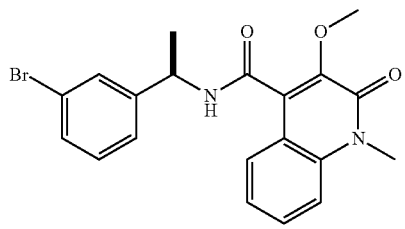 [SMILES: COc1c(C(=O)N[C@H](C)c2cccc(Br)c2)c2ccccc2n(C)c1=O]

(R)-N-(1-(3-Bromophenyl)ethyl)-3-hydroxy-1-methyl-2-oxo-1,2-dihydroquinoline-4-carboxamide (Example 45A, 230 mg, 0.57 mmol) was stirred in acetonitrile (4 mL) and MeOH (1 mL) at rt. Trimethylsilyldiazomethane (0.29 mL, 0.57 mmol) was added dropwise. The mixture was stirred at rt for 1 h. The mixture was concentrated and dried under vacuum to give Example 74A (238 mg, 0.57 mmol, 100% yield). LC-MS (ESI) 416.9 (M+H), RT=1.92 min (Method B).

Example 74B (R)-tert-butyl 4-(3-(1-(3-methoxy-1-methyl-2-oxo-1,2-dihydroquinoline-4-carboxamido)ethyl)phenyl)piperazine-1-carboxylate

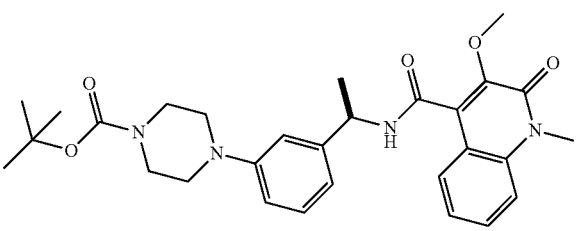 [SMILES: COc1c(C(=O)N[C@H](C)c2cccc(N3CCN(C(=O)OC(C)(C)C)CC3)c2)c2ccccc2n(C)c1=O]

A mixture of tert-butyl piperazine-1-carboxylate (29 mg, 0.16 mmol), Example 74A (50 mg, 0.12 mmol), Pd₂(dba)₃ (11 mg, 0.012 mmol), Xantphos (21 mg, 0.036 mmol) and sodium tert-butoxide (35 mg, 0.36 mmol) in anhydrous dioxane (1 mL) was degassed with argon. The reaction mixture was heated at 90° C. for 2 h. The mixture was allowed to cool and filtered through Celite®. The filtrate was concentrated and purified by chromatography (EtOAc/hexanes) to yield Example 74B. LC-MS (ESI) 420.9 (M-Boc+H), RT=1.95 min (Method B).

Example 74C (R)-3-methoxy-1-methyl-2-oxo-N-(1-(3-(piperazin-1-yl)phenyl)ethyl)-1,2-dihydroquinoline-4-carboxamide

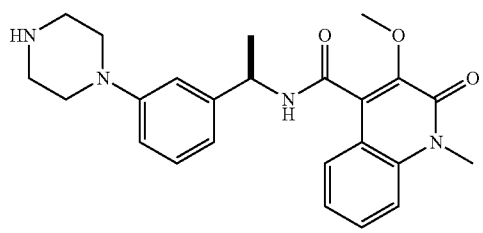 [SMILES: COc1c(C(=O)N[C@H](C)c2cccc(N3CCNCC3)c2)c2ccccc2n(C)c1=O]

Example 74B (80 mg, 0.154 mmol) was stirred in CH$_2$Cl$_2$ and TFA at rt for 30 min. The mixture was concentrated and dried to give Example 74C, which was used directly in the next step. LCMS=421.1 [M+1] RT=1.38 min (Method B).

Example 74

Example 74C (18 mg, 0.043 mmol) was stirred in CH$_2$Cl$_2$ (1 mL) at rt. Trichloroborane (0.086 ml, 0.086 mmol) was added dropwise. The resulting solution was stirred at rt for 0.5 h. MeOH was added and stirred for 20 min. The solvents were removed under reduced pressure and the residue was purified by HPLC (MeOH/H$_2$O/TFA) to give Example 74 (16 mg, 0.038 mmol, 88% yield). LCMS=430.1 [M+1], RT=1.92 min (Method B); Orthogonal HPLC (150×4.6 mm 3.5 µm, 254 nm): Sunfire {RT=4.121 min, 97.3%}; Xbridge {RT=4.825 min, 99.2%). $^1$H NMR (400 MHz, acetone) δ ppm 7.90 (1H, br. s.), 7.58 (1H, d, J=7.8 Hz), 7.30-7.51 (2 H, m), 7.07-7.27 (3 H, m), 6.94 (1 H, d, J=7.3 Hz), 6.84 (1 H, dd, J=8.1, 2.0 Hz), 4.80-5.46 (1 H, m), 3.69 (3 H, s), 3.34-3.54 (8 H, m), 1.48 (3 H, d, J=7.1 Hz).

Example 75

6-(4-fluorophenyl)-3-hydroxy-1-methyl-2-oxo-N-(3-(2-(trifluoromethyl)phenyl)propyl)-1,2-dihydro-quinoline-4-carboxamide

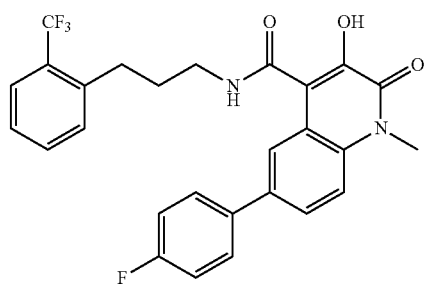 [SMILES: Cn1c(=O)c(O)c(C(=O)NCCCc2ccccc2C(F)(F)F)c2cc(-c3ccc(F)cc3)ccc21]

Example 75A 6-iodo-3-methoxy-1-methyl-2-oxo-N-(3-(2-(trifluoromethyl)phenyl)propyl)-1,2-dihydroquinoline-4-carboxamide

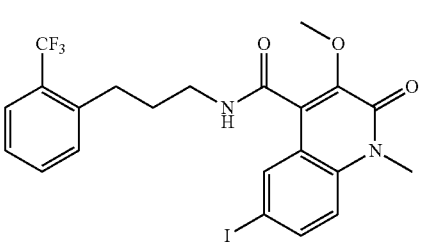 [SMILES: COc1c(C(=O)NCCCc2ccccc2C(F)(F)F)c2cc(I)ccc2n(C)c1=O]

3-Hydroxy-6-iodo-2-oxo-N-(3-(2-(trifluoromethyl)phenyl)propyl)-1,2-dihydroquinoline-4-carboxamide (100 mg, 0.19 mmol), prepared by the method described for Example 3, cesium carbonate (189 mg, 0.58 mmol) and iodomethane (69 mg, 0.48 mmol) were stirred in DMF (2 mL). The sealed reaction was stirred at 80° C. for 1.5 h. After cooling, H$_2$O and EtOAc were added. The organic layer was washed with brine (2×), dried over MgSO$_4$, filtered and concentrated. The residue was purified by ISCO flash chromatography on silica gel (hexanes/EtOAc) to give Example 75A (52 mg, 0.096 mmol, 49% yield). LC-MS (ESI) 545.0 (M+H), RT=2.14 min (Method B).

Example 75B 6-(4-fluorophenyl)-3-methoxy-1-methyl-2-oxo-N-(3-(2-(trifluoromethyl)phenyl) propyl)-1,2-dihydro-quinoline-4-carboxamide

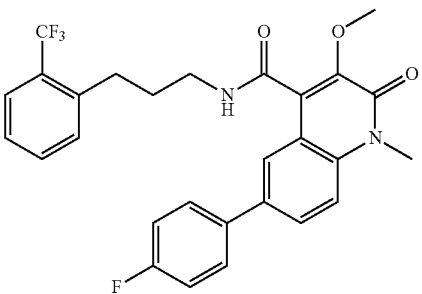 [SMILES: COc1c(C(=O)NCCCc2ccccc2C(F)(F)F)c2cc(-c3ccc(F)cc3)ccc2n(C)c1=O]

4-Fluorophenylboronic acid (21 mg, 0.15 mmol) and Example 75A (40 mg, 0.073 mmol), Na$_2$CO$_3$ (0.18 mL, 0.18 mmol) and PdCl$_2$(dppf)-CH$_2$Cl$_2$Adduct (12 mg, 0.015 mmol) were stirred in dioxane (1 mL) in a sealed microwave vial. The reaction was degassed 2 times with argon and then heated at 100° C. for 1.5 h. EtOAc and H$_2$O were added to the mixture. The organic layer was separated and washed with H$_2$O and brine, dried over MgSO$_4$, filtered and concentrated. The residue was purified by ISCO flash chromatography on silica gel (hexanes/EtOAc) to give pure Example 75B (22 mg, 0.043 mmol, 58.4% yield). LC-MS (ESI) 513.1 (M+H), RT=2.21 min (Method B).

Example 75

Example 75B (22 mg, 0.043 mmol) was stirred in CH$_2$Cl$_2$ (1 mL) at rt. Trichloroborane (0.086 ml, 0.086 mmol) was added dropwise. The resulting solution was stirred at rt for 1 h. MeOH was added and the resulting solution was stirred for an additional 20 min. The precipitate was collected and rinsed with MeOH to give Example 75 (14 mg, 0.027 mmol, 63% yield). LCMS=499.1 [M+1], RT=2.21 min (Method B); Orthogonal HPLC (150×4.6 mm 3.5 μm, 254 nm): Sunfire {RT=10.926 min, 96.2%}; Xbridge {RT=9.691 min, 96.6%). $^1$H NMR (400 MHz, chloroform-d) δ ppm 8.38 (1 H, s), 7.52-7.78 (4 H, m), 7.34-7.52 (3 H, m), 7.25-7.34 (1 H, m), 7.12 (2H, t, J=8.6 Hz), 6.67 (1 H, br. s.), 3.64 (2 H, q, J=6.4 Hz), 2.71-3.05 (2 H, m), 1.85-2.17 (2 H, m).

Example 76

6-cyano-3-hydroxy-1-methyl-2-oxo-N-(3-(2-(trifluoromethyl)phenyl)propyl)-1,2-dihydroquinoline-4-carboxamide

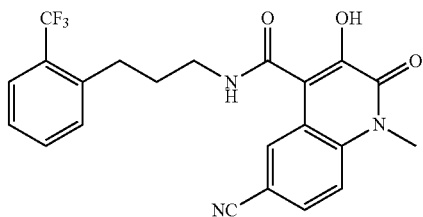 [SMILES: Cn1c(=O)c(O)c(C(=O)NCCCc2ccccc2C(F)(F)F)c2cc(C#N)ccc21]

Example 76A 6-cyano-3-methoxy-1-methyl-2-oxo-N-(3-(2-(trifluoromethyl)phenyl)propyl)-1,2-dihydroquinoline-4-carboxamide

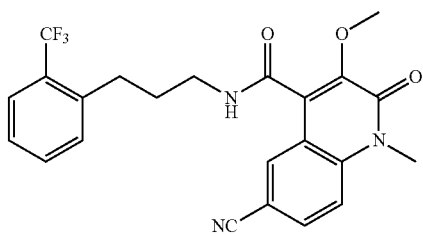 [SMILES: COc1c(C(=O)NCCCc2ccccc2C(F)(F)F)c2cc(C#N)ccc2n(C)c1=O]

Example 75A (20 mg, 0.037 mmol), zinc cyanide (8.63 mg, 0.073 mmol) and tetrakistriphenylphosphine palladium (8.49 mg, 7.35 mmol) were stirred at rt in a sealed microwave vial. DMF (0.5 mL) was added. The mixture was degassed (2×) with argon then heated at 100° C. for 3 h. After cooling, EtOAc was added and the organic solution was washed with H$_2$O, brine, dried (MgSO$_4$), filtered and concentrated. The residue was purified by ISCO flash chromatography on silica gel (Hex/EtOAc) to give Example 76A (15 mg, 0.034 mmol, 92% yield), LC-MS (ESI) 444.0 (M+H), RT=1.89 min (Method B).

Example 76

Example 76A (15 mg, 0.034 mmol) was stirred in CH$_2$Cl$_2$ (1 mL) at rt. Trichloroborane (0.068 mL, 0.068 mmol) was added dropwise. The resulting solution was stirred at rt for 1 h. MeOH was added and stirred for an additional 20 min. The solvents were concentrated and the residue was purified by HPLC to give Example 76 (9 mg, 62% yield). LCMS=430.1 [M+1], RT=1.92 min (Method B); Orthogonal HPLC (150× 4.6 mm 3.5 nm, 254 nm): Sunfire {RT=9.973 min, 100%}; Xbridge {RT=8.206 min, 100%). $^1$H NMR (400 MHz, chloroform-d) δ ppm 8.70 (1 H, d, J=1.5 Hz), 7.77-7.97 (1 H, m), 7.71 (1 H, dd, J=8.8, 1.8 Hz), 7.63 (1 H, d, J=7.8 Hz), 7.35-7.55 (3H, m), 7.31 (1 H, t, J=8.0 Hz), 6.73 (1 H, br. s.), 3.86 (3 H, s), 3.63 (2H, m), 2.68-3.16 (2 H, m), 1.81-2.24 (2 H, m).

Example 77

3-hydroxy-1-methyl-2-oxo-N4-(3-(2-(trifluoromethyl)phenyl)propyl)-1,2-dihydroquinoline-4,6-dicarboxamide

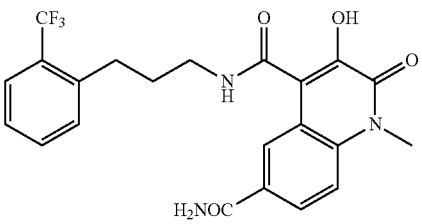 [SMILES: Cn1c(=O)c(O)c(C(=O)NCCCc2ccccc2C(F)(F)F)c2cc(C(N)=O)ccc21]

Example 76 (5 mg, 0.012 mmol) was stirred in DMSO (0.3 mL) at rt. Hydrogen peroxide (4 drops) and 1N NaOH (4 drops) were added. The resulting mixture was stirred at rt for 1 h. The reaction mixture was purified by HPLC (CH$_3$CN/ H$_2$O/TFA) to give Example 77 (4 mg, 8.76 mmol, 75% yield) after drying. LCMS=448.1 [M+1] RT=1.76 min (Method B); Orthogonal HPLC (150×4.6 mm 3.5 μm, 254 nm): Sunfire {RT=6.933 min, 98.5%}; Xbridge {RT=6.461 min, 99.2%).

Examples 78-191 were synthesized following the procedure described for Example 3. The crude mixtures were purified by using Method G and the purity of each compound was obtained by Method F. The analytical data for Examples 78-191 are listed in the following Table.

| Ex. # | Structure | Name | LC-MS [M + 1]/RT | Purity % |
|---|---|---|---|---|
| 78 | ![structure] | 3-hydroxy-1-methyl-2-oxo-N-(4-phenylbutan-2-yl)-1,2-dihydroquinuline-4-carboxamide | 351.2/2.22 min | 94.8 |

| Ex. # | Structure | Name | LC-MS [M + 1]/RT | Purity % |
|---|---|---|---|---|
| 79 | 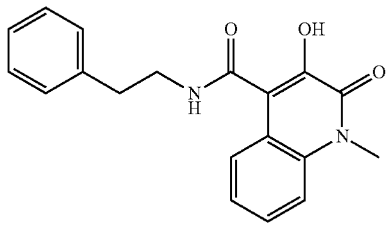 [SMILES: Cn1c(=O)c(O)c(C(=O)NCCc2ccccc2)c2ccccc21] | 3-hydroxy-1-methyl-2-oxo-N-phenethyl-1,2-dihydroquinoline-4-carboxamide | 323.04/1.89 min | 92.4 |
| 80 | 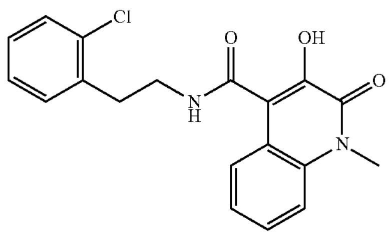 [SMILES: Cn1c(=O)c(O)c(C(=O)NCCc2ccccc2Cl)c2ccccc21] | N-(2-chlorophenethyl)-3-hydroxy-1-methyl-2-oxo-1,2-dihydroquinoline-4-carboxamide | 357.07/2.09 min | 95.3 |
| 81 | 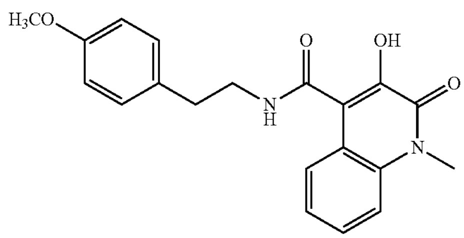 [SMILES: COc1ccc(CCNC(=O)c2c(O)c(=O)n(C)c3ccccc23)cc1] | 3-hydroxy-N-(4-methoxyphenethyl)-1-methyl-2-oxo-1,2-dihydroquinoline-4-carboxamide | 353.15/1.87 min | 92.3 |
| 82 | 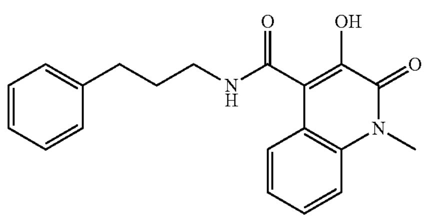 [SMILES: Cn1c(=O)c(O)c(C(=O)NCCCc2ccccc2)c2ccccc21] | 3-hydroxy-1-methyl-2-oxo-N-(3-phenylpropyl)-1,2-dihydroquinoline-4-carboxamide | 337.2/2.08 min | 95.1 |
| 83 | 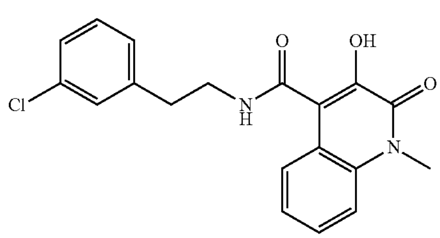 [SMILES: Cn1c(=O)c(O)c(C(=O)NCCc2cccc(Cl)c2)c2ccccc21] | N-(3-chlorophenethyl)-3-hydroxy-1-methyl-2-oxo-1,2-dihydroquinoline-4-carboxamide | 357.06/2.11 min | 94.1 |
| 84 | 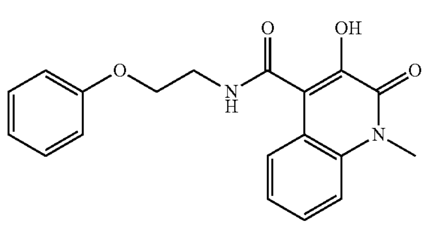 [SMILES: Cn1c(=O)c(O)c(C(=O)NCCOc2ccccc2)c2ccccc21] | 3-hydroxy-1-methyl-2-oxo-N-(2-phenoxyethyl)-1,2-dihydroquinoline-4-carboxamide | 339.13/1.9 min | 92.5 |

-continued

| Ex. # | Structure | Name | LC-MS [M + 1]/RT | Purity % |
|---|---|---|---|---|
| 85 | 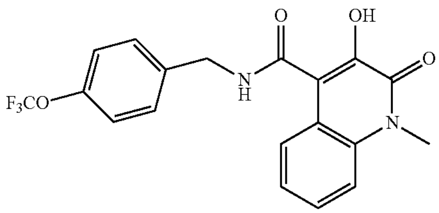 [SMILES: Cn1c(=O)c(O)c(C(=O)NCc2ccc(OC(F)(F)F)cc2)c2ccccc21] | 3-hydroxy-1-methyl-2-oxo-N-(4-(trifluoromethoxy)benzyl)-1,2-dihydroquinoline-4-carboxamide | 393.08/2.27 min | 97.5 |
| 86 | 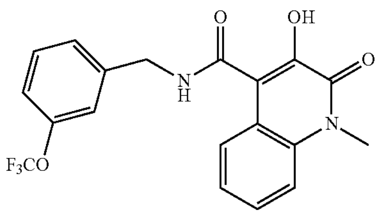 [SMILES: Cn1c(=O)c(O)c(C(=O)NCc2cccc(OC(F)(F)F)c2)c2ccccc21] | 3-hydroxy-1-methyl-2-oxo-N-(3-(trifluoromethoxy)benzyl)-1,2-dihydroquinoline-4-carboxamide | 393.11/2.25 min | 95.0 |
| 87 | 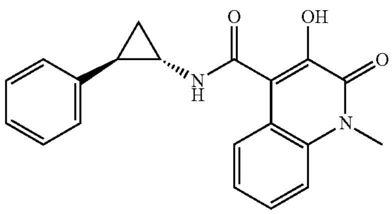 [SMILES: Cn1c(=O)c(O)c(C(=O)N[C@H]2C[C@@H]2c2ccccc2)c2ccccc21] | 3-hydroxy-1-methyl-2-oxo-N-((1S,2R)-2-phenylcyclopropyl)-1,2-dihydroquinoline-4-carboxamide | 335.09/1.99 min | 92.0 |
| 88 | 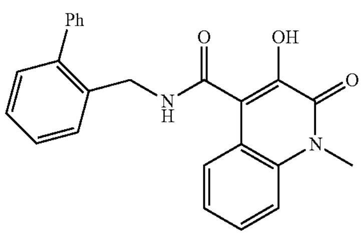 [SMILES: Cn1c(=O)c(O)c(C(=O)NCc2ccccc2-c2ccccc2)c2ccccc21] | N-(biphenyl-2-ylmethyl)-3-hydroxy-1-methyl-2-oxo-1,2-dihydroquinoline-4-carboxamide | 385.13/2.37 min | 93.3 |
| 89 | 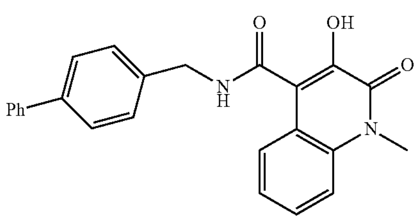 [SMILES: Cn1c(=O)c(O)c(C(=O)NCc2ccc(-c3ccccc3)cc2)c2ccccc21] | 3-hydroxy-1-methyl-2-oxo-N-(4-phenoxybenzyl)-1,2-dihydroquinoline-4-carboxamide | 401.13/5.61 min | 91.6 |
| 90 | 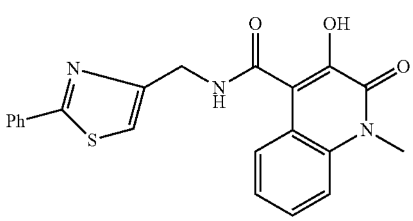 [SMILES: Cn1c(=O)c(O)c(C(=O)NCc2csc(-c3ccccc3)n2)c2ccccc21] | 3-hydroxy-1-methyl-2-oxo-N-((2-phenylthiazol-4-yl)methyl)-1,2-dihydroquinoline-4-carboxamide | 392.08/2.07 min | 97.0 |
| 91 | 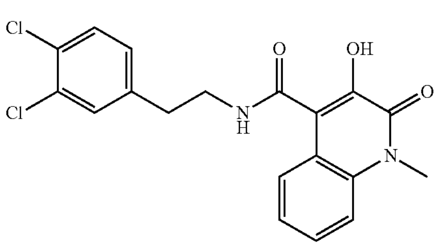 [SMILES: Cn1c(=O)c(O)c(C(=O)NCCc2ccc(Cl)c(Cl)c2)c2ccccc21] | N-(3,4-dichlorophenethyl)-3-hydroxy-1-methyl-2-oxo-1,2-dihydroquinoline-4-carboxamide | 391.04/2.3 min | 96.7 |

| Ex. # | Structure | Name | LC-MS [M + 1]/RT | Purity % |
|---|---|---|---|---|
| 92 | 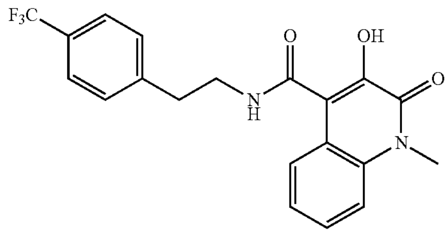 [SMILES: Cn1c(=O)c(O)c(C(=O)NCCc2ccc(C(F)(F)F)cc2)c2ccccc21] | 3-hydroxy-1-methyl-2-oxo-N-(4-(trifluoromethyl)phenethyl)-1,2-dihydroquinoline-4-carboxamide | 391.08/2.24 min | 95.7 |
| 93 | 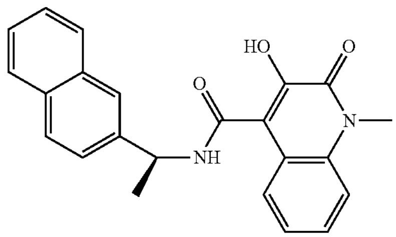 [SMILES: C[C@H](NC(=O)c1c(O)c(=O)n(C)c2ccccc12)c1ccc2ccccc2c1] | (S)-3-hydroxy-1-methyl-N-(1-(naphthalen-2-yl)ethyl)-2-oxo-1,2-dihydroquinoline-4-carboxamide | 373.12/2.28 min | 95.9 |
| 94 | 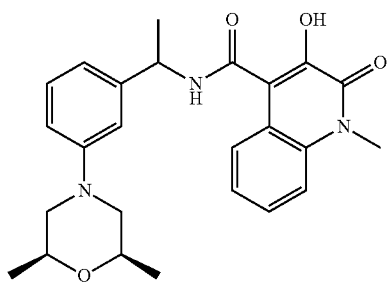 | N-(1-(3-((2S,6R)-2,6-dimethylmorpholino)phenyl)ethyl)-3-hydroxy-1-methyl-2-oxo-1,2-dihydroquinoline-4-carboxamide | 436.18/2.15 min | 95.9 |
| 95 | 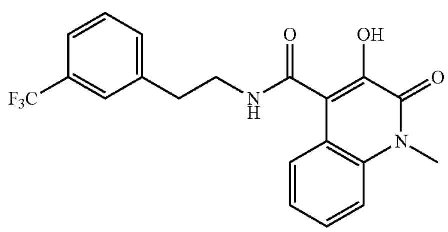 [SMILES: Cn1c(=O)c(O)c(C(=O)NCCc2cccc(C(F)(F)F)c2)c2ccccc21] | 3-hydroxy-1-methyl-2-oxo-N-(3-(trifluoromethyl)phenethyl)-1,2-dihydroquinoline-4-carboxamide | 391.13/2.24 min | 97.93 |
| 96 | 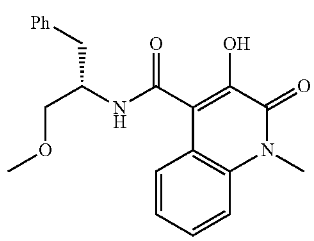 | (S)-3-hydroxy-N-(1-methoxy-3-phenylpropan-2-yl)-1-methyl-2-oxo-1,2-dihydroquinoline-4-carboxamide | 367.18/1.98 min | 88.9 |
| 97 | 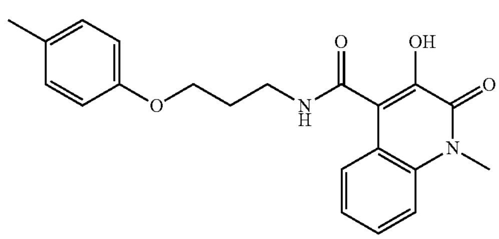 | 3-hydroxy-1-methyl-2-oxo-N-(3-(p-tolyloxy)propyl)-1,2-dihydroquinoline-4-carboxamide | 367.17/2.21 min | 94.4 |

-continued

| Ex. # | Structure | Name | LC-MS [M + 1]/RT | Purity % |
|---|---|---|---|---|
| 98 | 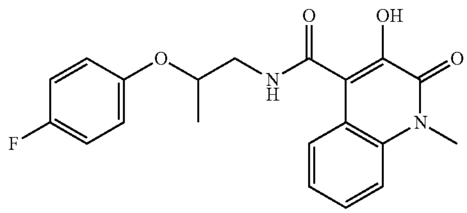 [SMILES: CC(CNC(=O)c1c(O)c(=O)n(C)c2ccccc12)Oc1ccc(F)cc1] | N-(2-(4-fluorophenoxy)propyl)-3-hydroxy-1-methyl-2-oxo-1,2-dihydroquinoline-4-carboxamide | 371.15/2.09 min | 96.1 |
| 99 | 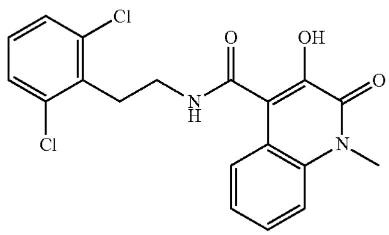 [SMILES: Cn1c(=O)c(O)c(C(=O)NCCc2c(Cl)cccc2Cl)c2ccccc21] | N-(2,6-dichlorophenethyl)-3-hydroxy-1-methyl-2-oxo-1,2-dihydroquinoline-4-carboxamide | 391.04/2.24 min | 95.9 |
| 100 | 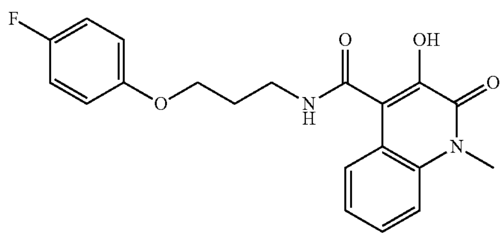 [SMILES: Cn1c(=O)c(O)c(C(=O)NCCCOc2ccc(F)cc2)c2ccccc21] | N-(3-(4-fluorophenoxy)propyl)-3-hydroxy-1-methyl-2-oxo-1,2-dihydroquinoline-4-carboxamide | 371.16/2.07 min | 96.1 |
| 101 | 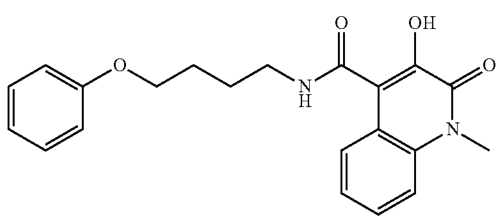 [SMILES: Cn1c(=O)c(O)c(C(=O)NCCCCOc2ccccc2)c2ccccc21] | 3-hydroxy-1-methyl-2-oxo-N-(4-phenoxybutyl)-1,2-dihydroquinoline-4-carboxamide | 367.13/2.15 min | 94.5 |
| 102 | 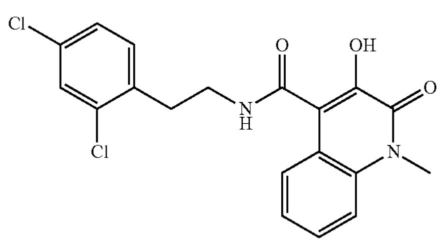 [SMILES: Cn1c(=O)c(O)c(C(=O)NCCc2ccc(Cl)cc2Cl)c2ccccc21] | N-(2,4-dichlorophenethyl)-3-hydroxy-1-methyl-2-oxo-1,2-dihydroquinoline-4-carboxamide | 391.04/2.34 min | 90.1 |
| 103 | 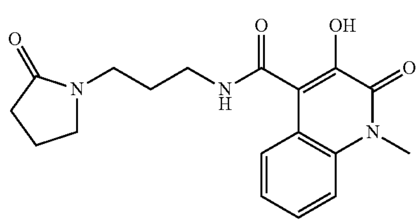 [SMILES: Cn1c(=O)c(O)c(C(=O)NCCCN2CCCC2=O)c2ccccc21] | 3-hydroxy-1-methyl-2-oxo-N-(3-(2-oxopyrrolidin-1-yl)propyl)-1,2-dihydroquinoline-4-carboxamide | 344.13/1.23 min | 100.0 |

| Ex. # | Name | LC-MS [M + 1]/RT | Purity % |
|---|---|---|---|
| 104 | N-(2,2-diphenylethyl)-3-hydroxy-1-methyl-2-oxo-1,2-dihydroquinoline-4-carboxamide | 399.18/2.33 min | 94.0 |
| 105 | 3-hydroxy-1-methyl-2-oxo-N-(4-(trifluoromethyl)benzyl)-1,2-dihydroquinoline-4-carboxamide | 377.08/2.17 min | 94.7 |
| 106 | N-(biphenyl-4-ylmethyl)-3-hydroxy-1-methyl-2-oxo-1,2-dihydroquinoline-4-carboxamide | 385.13/2.36 min | 100.0 |
| 107 | N-(benzo[d]thiazol-2-ylmethyl)-3-hydroxy-1-methyl-2-oxo-1,2-dihydroquinoline-4-carboxamide | 366.03/1.79 min | 96.4 |
| 108 | 3-hydroxy-1-methyl-2-oxo-N-(2-(piperidin-1-yl)benzyl)-1,2-dihydroquinoline-4-carboxamide | 392.22/2.43 min | 94.5 |
| 109 | 3-hydroxy-1-methyl-2-oxo-N-(2-(pyrrolidin-1-yl)benzyl)-1,2-dihydroquinoline-4-carboxamide | 378.21/2.16 min | 93.2 |

-continued

| Ex. # | Structure | Name | LC-MS [M + 1]/RT | Purity % |
|---|---|---|---|---|
| 110 | 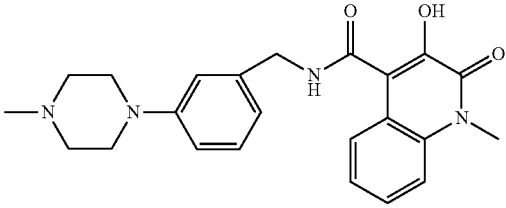 | 3-hydroxy-1-methyl-N-(3-(4-methylpiperazin-1-yl)benzyl)-2-oxo-1,2-dihydroquinoline-4-carboxamide | 407.22/1.27 min | 93.1 |
| 111 | 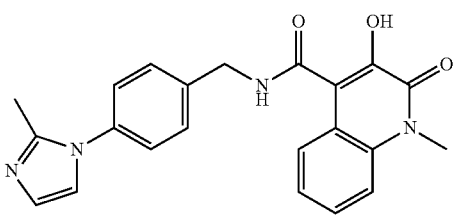 [SMILES: Cc1nccn1-c1ccc(CNC(=O)c2c(O)c(=O)n(C)c3ccccc23)cc1] | 3-hydroxy-1-methyl-N-(4-(2-methyl-1H-imidazol-1-yl)benzyl)-2-oxo-1,2-dihydroquinoline-4-carboxamide | 389.17/1.05 min | 96.4 |
| 112 | 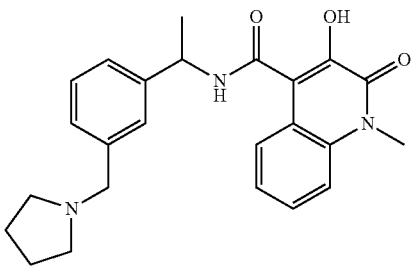 [SMILES: CC(NC(=O)c1c(O)c(=O)n(C)c2ccccc12)c1cccc(CN2CCCC2)c1] | 3-hydroxy-1-methyl-2-oxo-N-(1-(3-(pyrrolidin-1-ylmethyl)phenyl)ethyl)-1,2-dihydroquinoline-4-carboxamide | 406.26/1.19 min | 96.6 |
| 113 | 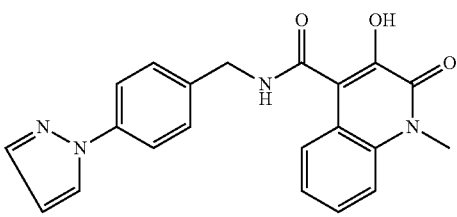 [SMILES: Cn1c(=O)c(O)c(C(=O)NCc2ccc(-n3cccn3)cc2)c2ccccc21] | N-(4-(1H-pyrazol-1-yl)benzyl)-3-hydroxy-1-methyl-2-oxo-1,2-dihydroquinoline-4-carboxamide | 375.16/1.62 min | 94.8 |
| 114 | 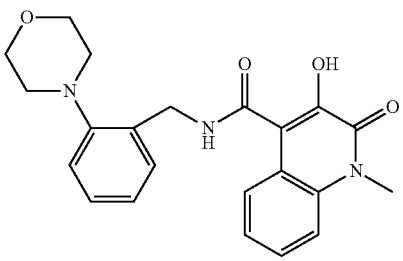 [SMILES: Cn1c(=O)c(O)c(C(=O)NCc2ccccc2N2CCOCC2)c2ccccc21] | 3-hydroxy-1-methyl-N-(2-morpholinobenzyl)-2-oxo-1,2-dihydroquinoline-4-carboxamide | 394.21/1.75 min | 94.2 |
| 115 | 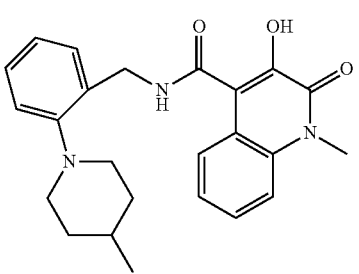 [SMILES: CC1CCN(c2ccccc2CNC(=O)c2c(O)c(=O)n(C)c3ccccc23)CC1] | 3-hydroxy-1-methyl-N-(2-(4-methylpiperidin-1-yl)benzyl)-2-oxo-1,2-dihydroquinoline-4-carboxamide | 406.24/2.64 min | 96.6 |

| Ex. # | Structure | Name | LC-MS [M + 1]/RT | Purity % |
|---|---|---|---|---|
| 116 | 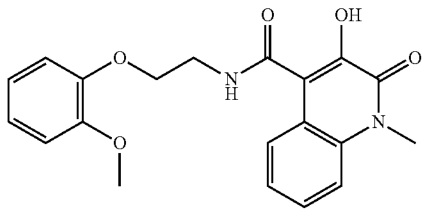 [SMILES: COc1ccccc1OCCNC(=O)c1c(O)c(=O)n(C)c2ccccc12] | 3-hydroxy-N-(2-(2-methoxyphenoxy)ethyl)-1-methyl-2-oxo-1,2-dihydroquinoline-4-carboxamide | 369.17/1.66 min | 97.4 |
| 117 | 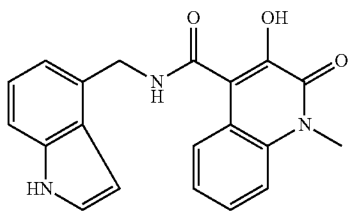 [SMILES: Cn1c(=O)c(O)c(C(=O)NCc2cccc3[nH]ccc23)c2ccccc21] | N-((1H-indol-4-yl)methyl)-3-hydroxy-1-methyl-2-oxo-1,2-dihydroquinoline-4-carboxamide | 348.12/1.53 min | 98.5 |
| 118 | 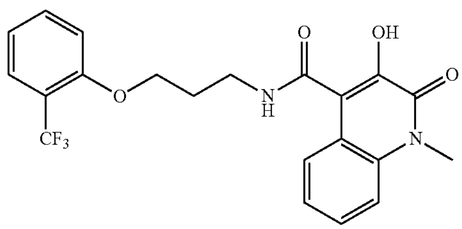 [SMILES: Cn1c(=O)c(O)c(C(=O)NCCCOc2ccccc2C(F)(F)F)c2ccccc21] | 3-hydroxy-1-methyl-2-oxo-N-(3-(2-(trifluoromethyl)phenoxy)propyl)-1,2-dihydroquinoline-4-carboxamide | 421.16/2.19 min | 94.6 |
| 119 | 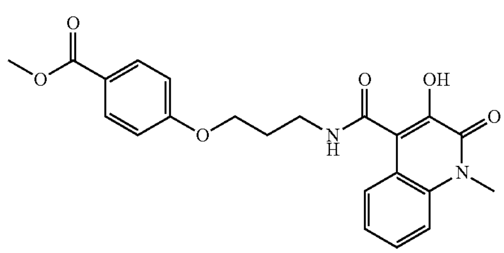 | methyl 4-(3-(3-hydroxy-1-methyl-2-oxo-1,2-dihydroquinoline-4-carboxamido)propoxy)benzoate | 411.18/1.84 min | 92.0 |
| 120 | 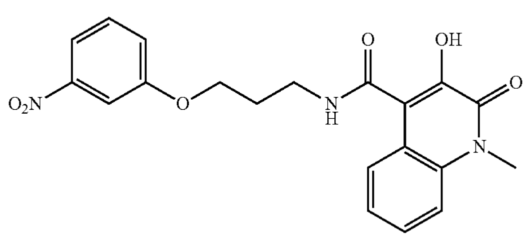 [SMILES: Cn1c(=O)c(O)c(C(=O)NCCCOc2cccc([N+](=O)[O-])c2)c2ccccc21] | 3-hydroxy-1-methyl-N-(3-(3-nitrophenoxy)propyl)-2-oxo-1,2-dihydroquinoline-4-carboxamide | 398.15/1.9 min | 95.4 |
| 121 | 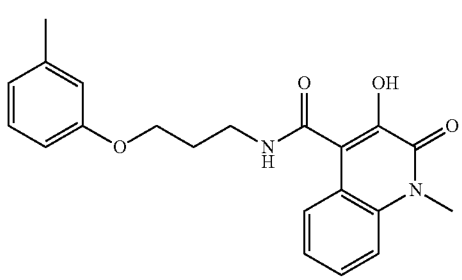 [SMILES: Cc1cccc(OCCCNC(=O)c2c(O)c(=O)n(C)c3ccccc23)c1] | 3-hydroxy-1-methyl-2-oxo-N-(3-(o-tolyloxy)propyl)-1,2-dihydroquinoline-4-carboxamide | 367.2/2.1 min | 98.6 |

-continued

| Ex. # | Structure | Name | LC-MS [M + 1]/RT | Purity % |
|---|---|---|---|---|
| 122 | 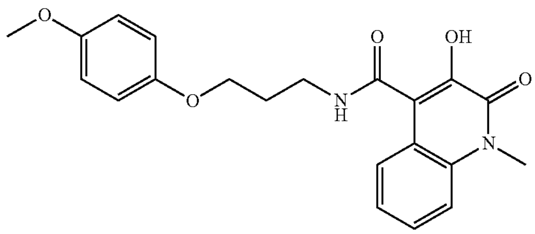 | 3-hydroxy-N-(3-(4-methoxyphenoxy)propyl)-1-methyl-2-oxo-1,2-dihydroquinoline-4-carboxamide | 383.17/1.82 min | 93.0 |
| 123 | 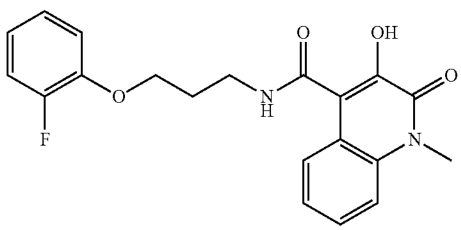 [SMILES: Cn1c(=O)c(O)c(C(=O)NCCCOc2ccccc2F)c2ccccc21] | N-(3-(2-fluorophenoxy)propyl)-3-hydroxy-1-methyl-2-oxo-1,2-dihydroquinoline-4-carboxamide | 371.15/1.89 min | 92.9 |
| 124 | 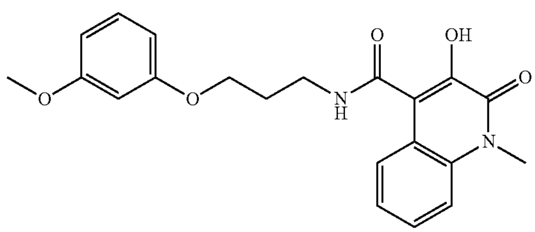 | 3-hydroxy-N-(3-(3-methoxyphenoxy)propyl)-1-methyl-2-oxo-1,2-dihydroquinoline-4-carboxamide | 383.16/1.88 min | 97.6 |
| 125 | 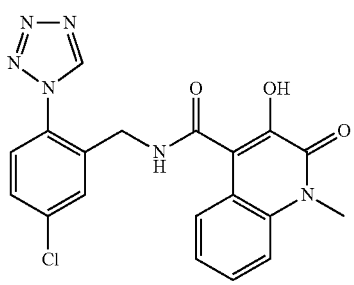 [SMILES: Cn1c(=O)c(O)c(C(=O)NCc2cc(Cl)ccc2-n2cnnn2)c2ccccc21] | N-(5-chloro-2-(1H-tetrazol-1-yl)benzyl)-3-hydroxy-1-methyl-2-oxo-1,2-dihydroquinoline-4-carboxamide | 411.12/1.65 min | 95.6 |
| 126 | 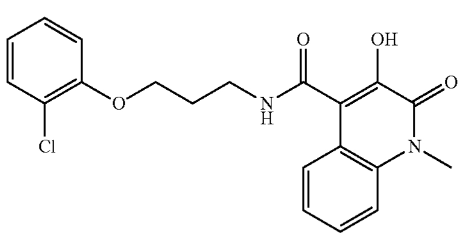 [SMILES: Cn1c(=O)c(O)c(C(=O)NCCCOc2ccccc2Cl)c2ccccc21] | N-(3-(2-chlorophenoxy)propyl)-3-hydroxy-1-methyl-2-oxo-1,2-dihydroquinoline-4-carboxamide | 387.12/2.02 min | 100.0 |
| 127 | 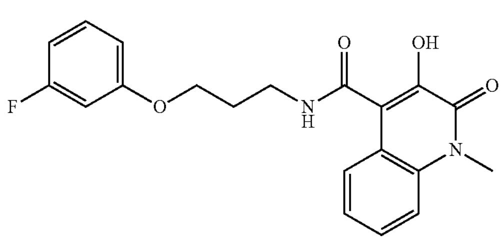 [SMILES: Cn1c(=O)c(O)c(C(=O)NCCCOc2cccc(F)c2)c2ccccc21] | N-(3-(3-fluorophenoxy)propyl)-3-hydroxy-1-methyl-2-oxo-1,2-dihydroquinoline-4-carboxamide | 371.15/1.96 min | 100.0 |

| Ex. # | Structure | Name | LC-MS [M + 1]/RT | Purity % |
|---|---|---|---|---|
| 128 | 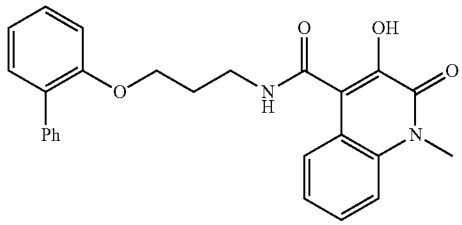 | N-(3-(biphenyl-2-yloxy)propyl)-3-hydroxy-1-methyl-2-oxo-1,2-dihydroquinoline-4-carboxamide | 429.22/2.39 min | 100.0 |
| 129 | 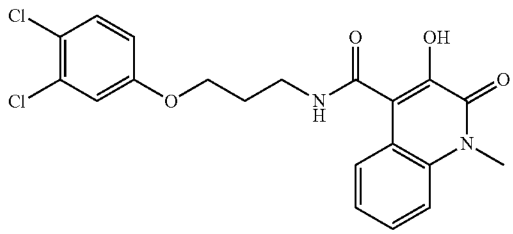 [SMILES: Cn1c(=O)c(O)c(C(=O)NCCCOc2ccc(Cl)c(Cl)c2)c2ccccc21] | N-(3-(3,4-dichlorophenoxy)propyl)-3-hydroxy-1-methyl-2-oxo-1,2-dihydroquinoline-4-carboxamide | 421.1/2.33 | 100.0 |
| 130 | 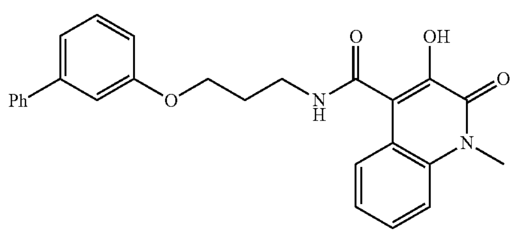 [SMILES: Cn1c(=O)c(O)c(C(=O)NCCCOc2cccc(-c3ccccc3)c2)c2ccccc21] | N-(3-(biphenyl-3-yloxy)propyl)-3-hydroxy-1-methyl-2-oxo-1,2-dihydroquinoline-4-carboxamide | 429.2/2.43 min | 100.0 |
| 131 | 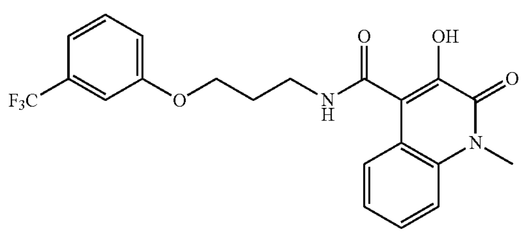 [SMILES: Cn1c(=O)c(O)c(C(=O)NCCCOc2cccc(C(F)(F)F)c2)c2ccccc21] | 3-hydroxy-1-methyl-2-oxo-N-(3-(3-(trifluoromethyl)phenoxy)propyl)-1,2-dihydroquinoline-4-carboxamide | 421.18/2.26 min | 100.0 |
| 132 | 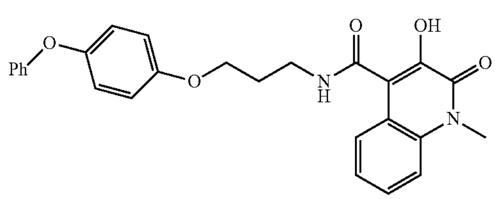 [SMILES: Cn1c(=O)c(O)c(C(=O)NCCCOc2ccc(Oc3ccccc3)cc2)c2ccccc21] | 3-hydroxy-1-methyl-2-oxo-N-(3-(4-phenoxyphenoxy)propyl)-1,2-dihydroquinoline-4-carboxamide | 445.19/2.43 min | 100.0 |
| 133 | 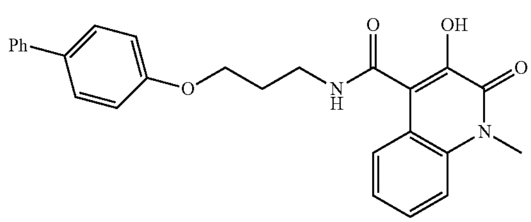 [SMILES: Cn1c(=O)c(O)c(C(=O)NCCCOc2ccc(-c3ccccc3)cc2)c2ccccc21] | N-(3-(biphenyl-4-yloxy)propyl)-3-hydroxy-1-methyl-2-oxo-1,2-dihydroquinoline-4-carboxamide | 429.21 / 2.45 min | 100.0 |

-continued

| Ex. # | Structure | Name | LC-MS [M + 1]/RT | Purity % |
|---|---|---|---|---|
| 134 | 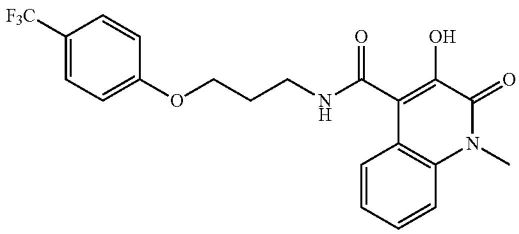 [SMILES: Cn1c(=O)c(O)c(C(=O)NCCCOc2ccc(C(F)(F)F)cc2)c2ccccc21] | 3-hydroxy-1-methyl-2-oxo-N-(3-(4-(trifluoromethyl)phenoxy)propyl)-1,2-dihydroquinoline-4-carboxamide | 421.18/2.26 min | 100.0 |
| 135 | 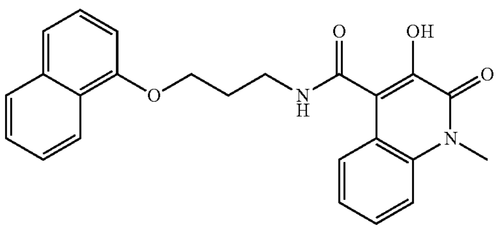 [SMILES: Cn1c(=O)c(O)c(C(=O)NCCCOc2cccc3ccccc23)c2ccccc21] | 3-hydroxy-1-methyl-N-(3-(naphthalen-1-yloxy)propyl)-2-oxo-1,2-dihydroquinoline-4-carboxamide | 403.2/2.25 min | 100.0 |
| 136 | 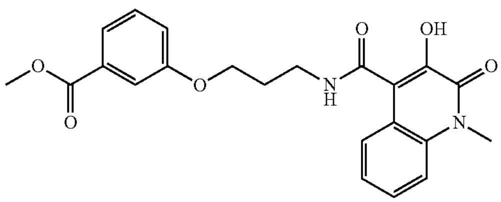 | methyl 3-(3-(3-hydroxy-1-methyl-2-oxo-1,2-dihydroquinoline-4-carboxamido)propoxy)benzoate | 411.19/1.88 min | 100.0 |
| 137 | 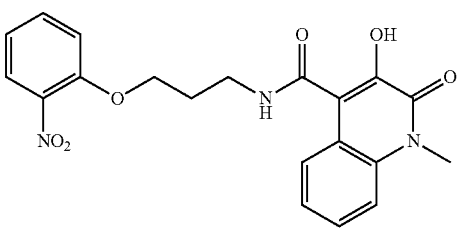 [SMILES: Cn1c(=O)c(O)c(C(=O)NCCCOc2ccccc2[N+](=O)[O-])c2ccccc21] | 3-hydroxy-1-methyl-N-(3-(2-nitrophenoxy)propyl)-2-oxo-1,2-dihydroquinoline-4-carboxamide | 398.16/1.78 min | 100.0 |
| 138 | 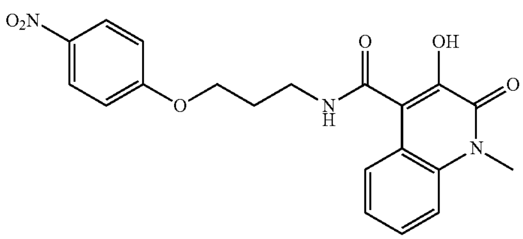 | 3-hydroxy-1-methyl-N-(3-(4-nitrophenoxy)propyl)-2-oxo-1,2-dihydroquinoline-4-carboxamide | 398.18/1.87 min | 100.0 |
| 139 | 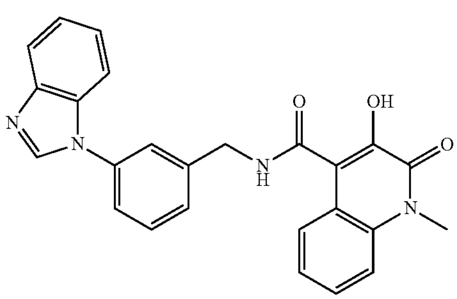 [SMILES: Cn1c(=O)c(O)c(C(=O)NCc2cccc(-n3cnc4ccccc43)c2)c2ccccc21] | N-(3-(1H-benzo[d]imidazol-1-yl)benzyl)-3-hydroxy-1-methyl-2-oxo-1,2-dihydroquinoline-4-carboxamide | 425.19/1.74 min | 100.0 |

-continued

| Ex. # | Structure | Name | LC-MS [M + 1]/RT | Purity % |
|---|---|---|---|---|
| 140 | 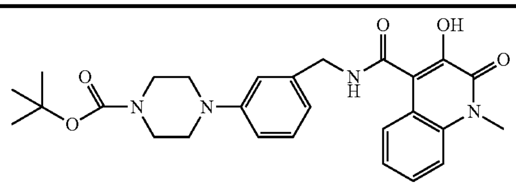 | tert-butyl 4-(3-((3-hydroxy-1-methyl-2-oxo-1,2-dihydroquinoline-4-carboxamido)methyl)phenyl)piperazine-1-carboxylate | 393.22/2.26 min | 100.0 |
| 141 | 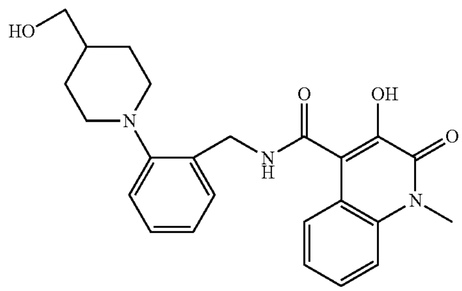 [SMILES: Cn1c(=O)c(O)c(C(=O)NCc2ccccc2N2CCC(CO)CC2)c2ccccc21] | 3-hydroxy-N-(2-(4-(hydroxymethyl)piperidin-1-yl)benzyl)-1-methyl-2-oxo-1,2-dihydroquinoline-4-carboxamide | 422.21/1.77 min | 100.0 |
| 142 | 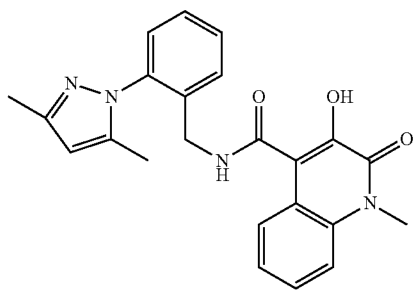 | N-(2-(3,5-dimethyl-1H-pyrazol-1-yl)benzyl)-3-hydroxy-1-methyl-2-oxo-1,2-dihydroquinoline-4-carboxamide | 403.21/1.83 min | 91.9 |
| 143 | 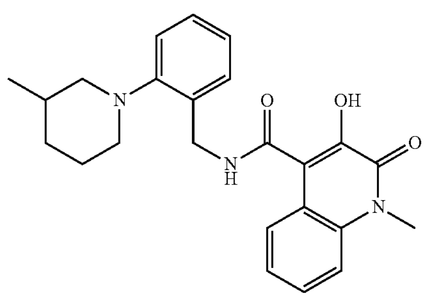 | 3-hydroxy-1-methyl-N-(2-(3-methylpiperidin-1-yl)benzyl)-2-oxo-1,2-dihydroquinoline-4-carboxamide | 406.24/2.64 min | 98.7 |
| 144 | 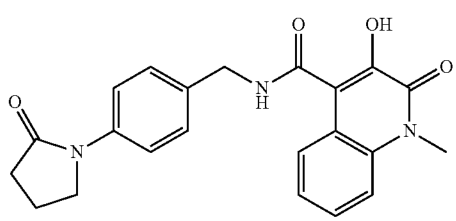 [SMILES: Cn1c(=O)c(O)c(C(=O)NCc2ccc(N3CCCC3=O)cc2)c2ccccc21] | 3-hydroxy-1-methyl-2-oxo-N-(4-(2-oxopyrrolidin-1-yl)benzyl)-1,2-dihydroquinoline-4-carboxamide | 392.22/1.41 min | 100.0 |
| 145 | 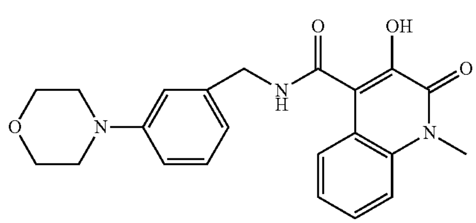 [SMILES: Cn1c(=O)c(O)c(C(=O)NCc2cccc(N3CCOCC3)c2)c2ccccc21] | 3-hydroxy-1-methyl-N-(3-morpholinobenzyl)-2-oxo-1,2-dihydroquinoline-4-carboxamide | 394.2/1.58 min | 89.9 |

-continued

| Ex. # | Structure | Name | LC-MS [M + 1]/RT | Purity % |
|---|---|---|---|---|
| 146 | 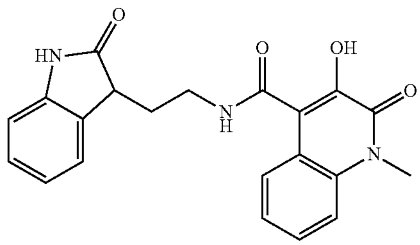 [SMILES: Cn1c(=O)c(O)c(C(=O)NCCC2C(=O)Nc3ccccc32)c2ccccc21] | 3-hydroxy-1-methyl-2-oxo-N-(2-(2-oxoindolin-3-yl)ethyl)-1,2-dihydroquinoline-4-carboxamide | 378.18/1.43 min | 96.7 |
| 147 | 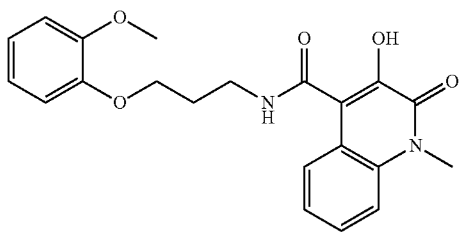 [SMILES: COc1ccccc1OCCCNC(=O)c1c(O)c(=O)n(C)c2ccccc12] | 3-hydroxy-N-(3-(2-methoxyphenoxy)propyl)-1-methyl-2-oxo-1,2-dihydroquinoline-4-carboxamide | 383.16/1.77 min | 89.7 |
| 148 | 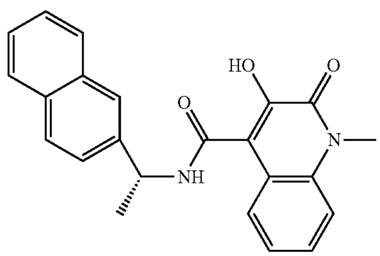 [SMILES: C[C@@H](NC(=O)c1c(O)c(=O)n(C)c2ccccc12)c1ccc2ccccc2c1] | (R)-3-hydroxy-1-methyl-N-(1-(naphthalen-2-yl)ethyl)-2-oxo-1,2-dihydroquinoline-4-carboxamide | 373.12/2.28 min | 100.0 |
| 149 | 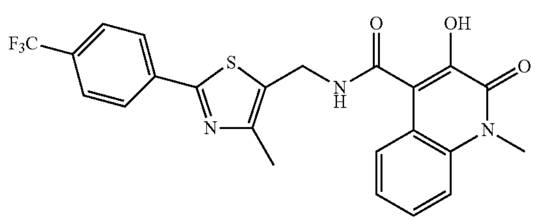 [SMILES: Cc1nc(-c2ccc(C(F)(F)F)cc2)sc1CNC(=O)c1c(O)c(=O)n(C)c2ccccc12] | 3-hydroxy-1-methyl-N-((4-methyl-2-(4-(trifluoromethyl)phenyl)thiazol-5-yl)methyl)-2-oxo-1,2-dihydroquinoline-4-carboxamide | 474.13/2.47 min | 100.0 |
| 150 | 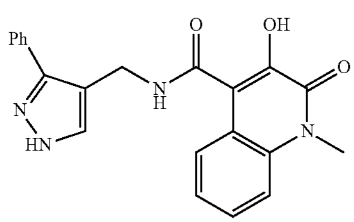 [SMILES: Cn1c(=O)c(O)c(C(=O)NCc2c[nH]nc2-c2ccccc2)c2ccccc21] | 3-hydroxy-1-methyl-2-oxo-N-((3-phenyl-1H-pyrazol-4-yl)methyl)-1,2-dihydroquinoline-4-carboxamide | 375.18/1.5 min | 99.2 |
| 151 | 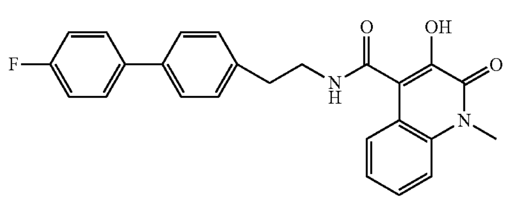 [SMILES: Cn1c(=O)c(O)c(C(=O)NCCc2ccc(-c3ccc(F)cc3)cc2)c2ccccc21] | N-(2-(4'-fluorobiphenyl-4-yl)ethyl)-3-hydroxy-1-methyl-2-oxo-1,2-dihydroquinoline-4-carboxamide | 417.23/2.43 min | 93.7 |

-continued

| Ex. # | Structure | Name | LC-MS [M + 1]/RT | Purity % |
|---|---|---|---|---|
| 152 | 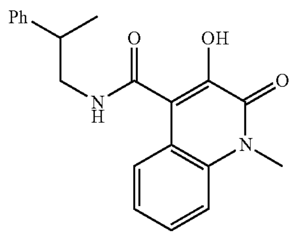 [SMILES: CC(CNC(=O)c1c(O)c(=O)n(C)c2ccccc12)c1ccccc1] | 3-hydroxy-1-methyl-2-oxo-N-(2-phenylpropyl)-1,2-dihydroquinoline-4-carboxamide | 337.16/1.96 min | 100.0 |
| 153 | 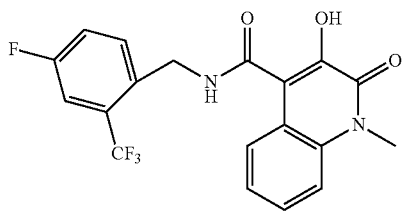 [SMILES: Cn1c(=O)c(O)c(C(=O)NCc2ccc(F)cc2C(F)(F)F)c2ccccc21] | N-(4-fluoro-2-(trifluoromethyl)benzyl)-3-hydroxy-1-methyl-2-oxo-1,2-dihydroquinoline-4-carboxamide | 395.15/2.16 min | 98.3 |
| 154 | 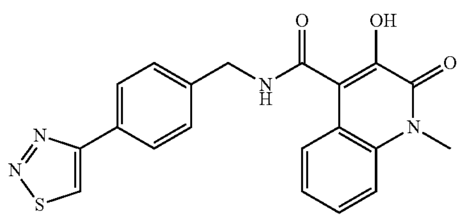 [SMILES: Cn1c(=O)c(O)c(C(=O)NCc2ccc(-c3csnn3)cc2)c2ccccc21] | N-(4-(1,2,3-thiadiazol-4-yl)benzyl)-3-hydroxy-1-methyl-2-oxo-1,2-dihydroquinoline-4-carboxamide | 393.18/1.74 min | 100.0 |
| 155 | 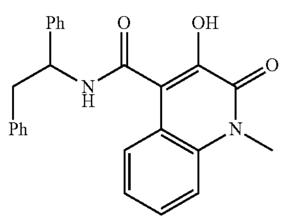 [SMILES: Cn1c(=O)c(O)c(C(=O)NC(Cc2ccccc2)c2ccccc2)c2ccccc21] | N-(1,2-diphenylethyl)-3-hydroxy-1-methyl-2-oxo-1,2-dihydroquinoline-4-carboxamide | 399.23/2.36 min | 92.8 |
| 156 | 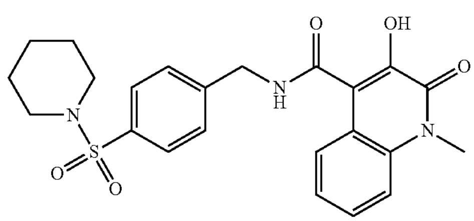 [SMILES: Cn1c(=O)c(O)c(C(=O)NCc2ccc(S(=O)(=O)N3CCCCC3)cc2)c2ccccc21] | 3-hydroxy-1-methyl-2-oxo-N-(4-(piperidin-1-ylsulfonyl)benzyl)-1,2-dihydroquinoline-4-carboxamide | 456.21/1.99 min | 94.6 |
| 157 | 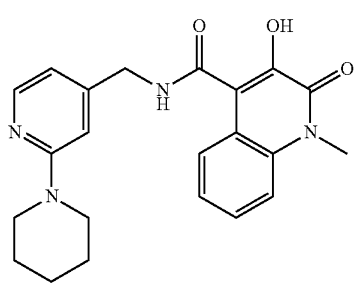 [SMILES: Cn1c(=O)c(O)c(C(=O)NCc2ccnc(N3CCCCC3)c2)c2ccccc21] | 3-hydroxy-1-methyl-2-oxo-N-((2-(piperidin-1-yl)pyridin-4-yl)methyl)-1,2-dihydroquinoline-4-carboxamide | 393.25/1.84 min | 98.2 |

| Ex. # | Structure | Name | LC-MS [M + 1]/RT | Purity % |
|---|---|---|---|---|
| 158 | 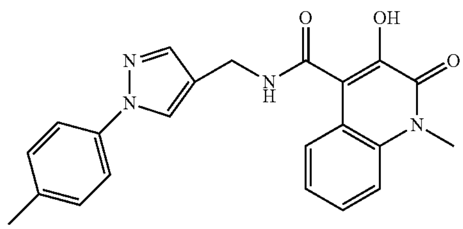 | 3-hydroxy-1-methyl-2-oxo-N-((1-p-tolyl-1H-pyrazol-4-yl)methyl)-1,2-dihydroquinoline-4-carboxamide | 389.21/1.93 min | 93.5 |
| 159 | 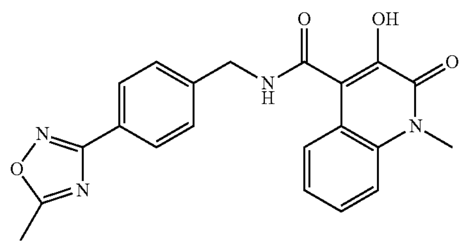 [SMILES: Cc1nc(-c2ccc(CNC(=O)c3c(O)c(=O)n(C)c4ccccc34)cc2)no1] | 3-hydroxy-1-methyl-N-(4-(5-methyl-1,2,4-oxadiazol-3-yl)benzyl)-2-oxo-1,2-dihydroquinoline-4-carboxamide | 391.18/1.72 min | 100.0 |
| 160 | 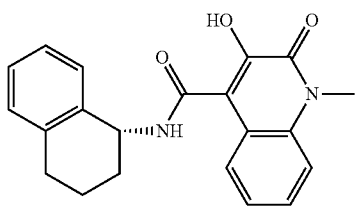 [SMILES: Cn1c(=O)c(O)c(C(=O)N[C@@H]2CCCc3ccccc32)c2ccccc21] | (R)-3-hydroxy-1-methyl-2-oxo-N-(1,2,3,4-tetrahydronaphthalen-1-yl)-1,2-dihydroquinoline-4-carboxamide | 349.15/2.08 min | 90.3 |
| 161 | 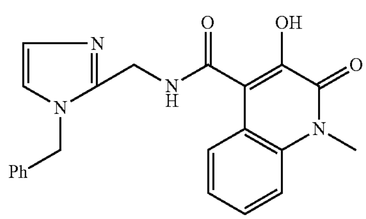 [SMILES: Cn1c(=O)c(O)c(C(=O)NCc2nccn2Cc2ccccc2)c2ccccc21] | N-((1-benzyl-1H-imidazol-2-yl)methyl)-3-hydroxy-1-methyl-2-oxo-1,2-dihydroquinoline-4-carboxamide | 389.22/1.66 min | 100.0 |
| 162 | 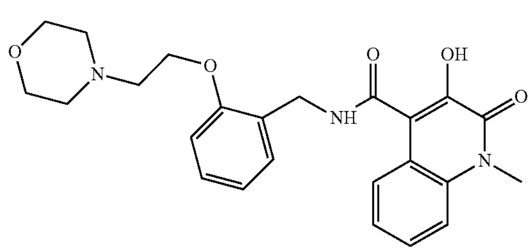 [SMILES: Cn1c(=O)c(O)c(C(=O)NCc2ccccc2OCCN2CCOCC2)c2ccccc21] | 3-hydroxy-1-methyl-N-(2-(2-morpholinoethoxy)benzyl)-2-oxo-1,2-dihydroquinoline-4-carboxamide | 438.24/1.64 min | 91.8 |
| 163 | 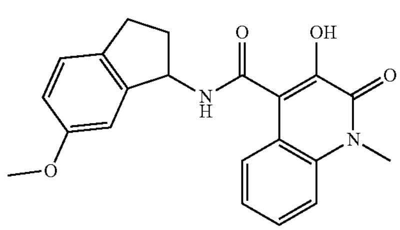 | 3-hydroxy-N-(6-methoxy-2,3-dihydro-1H-inden-1-yl)-1-methyl-2-oxo-1,2-dihydroquinoline-4-carboxamide | 365.17/1.95 min | 96.3 |

| Ex. # | Structure | Name | LC-MS [M + 1]/RT | Purity % |
|---|---|---|---|---|
| 164 | 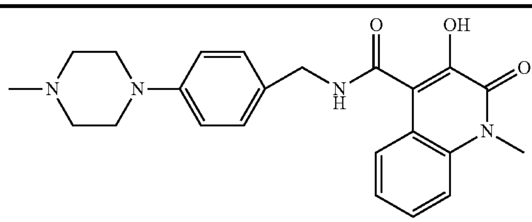 | 3-hydroxy-1-methyl-N-(4-(4-methylpiperazin-1-yl)benzyl)-2-oxo-1,2-dihydroquinoline-4-carboxamide | 407.25/1.28 min | 97.4 |
| 165 | 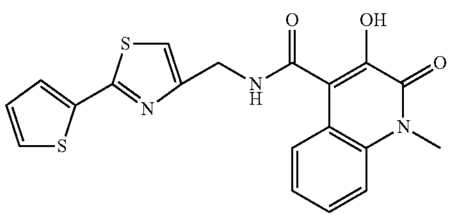 [SMILES: Cn1c(=O)c(O)c(C(=O)NCc2csc(-c3cccs3)n2)c2ccccc21] | 3-hydroxy-1-methyl-2-oxo-N-((2-(thiophen-2-yl)thiazol-4-yl)methyl)-1,2-dihydroquinoline-4-carboxamide | 398.09/1.87 min | 91.2 |
| 166 | 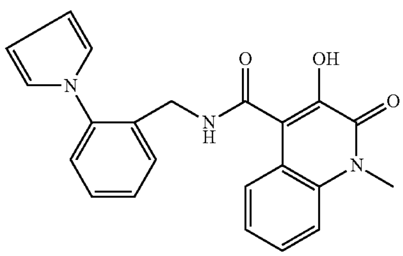 [SMILES: Cn1c(=O)c(O)c(C(=O)NCc2ccccc2-n2cccc2)c2ccccc21] | N-(2-(1H-pyrrol-1-yl)benzyl)-3-hydroxy-1-methyl-2-oxo-1,2-dihydroquinoline-4-carboxamide | 374.18/2.09 min | 96.4 |
| 167 | 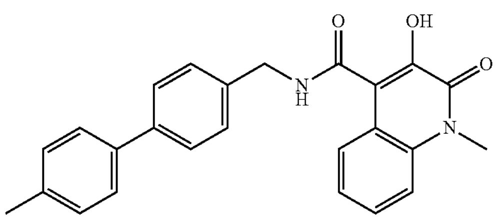 | 3-hydroxy-1-methyl-N-((4'-methylbiphenyl-4-yl)methyl)-2-oxo-1,2-dihydroquinoline-4-carboxamide | 399.23/2.53 min | 97.0 |
| 168 | 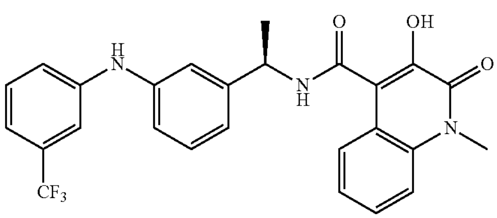 [SMILES: C[C@@H](NC(=O)c1c(O)c(=O)n(C)c2ccccc12)c1cccc(Nc2cccc(C(F)(F)F)c2)c1] | (R)-3-hydroxy-1-methyl-2-oxo-N-(1-(3-(3-(trifluoromethyl)phenylamino)phenyl)ethyl)-1,2-dihydroquinoline-4-carboxamide | NA | 97.5 |
| 169 | 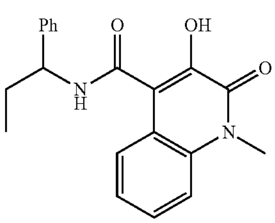 [SMILES: CCC(NC(=O)c1c(O)c(=O)n(C)c2ccccc12)c1ccccc1] | 3-hydroxy-1-methyl-2-oxo-N-(1-phenylpropyl)-1,2-dihydroquinoline-4-carboxamide | 337.16/2.02 min | 90.7 |
| 170 | 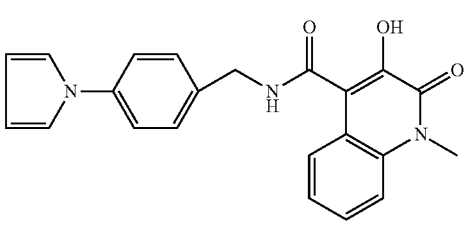 [SMILES: Cn1c(=O)c(O)c(C(=O)NCc2ccc(-n3cccc3)cc2)c2ccccc21] | N-(4-(1H-pyrrol-1-yl)benzyl)-3-hydroxy-1-methyl-2-oxo-1,2-dihydroquinoline-4-carboxamide | 374.17/2.1 min | 88.7 |

-continued

| Ex. # | Structure | Name | LC-MS [M + 1]/RT | Purity % |
|---|---|---|---|---|
| 171 | 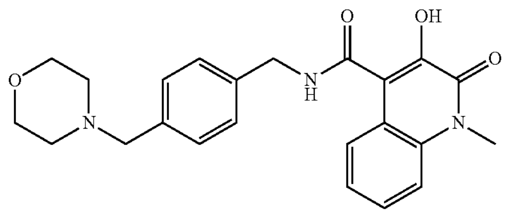 [SMILES: Cn1c(=O)c(O)c(C(=O)NCc2ccc(CN3CCOCC3)cc2)c2ccccc21] | 3-hydroxy-1-methyl-N-(4-(morpholinomethyl)benzyl)-2-oxo-1,2-dihydroquinoline-4-carboxamide | 408.23/1.49 min | 92.5 |
| 172 | 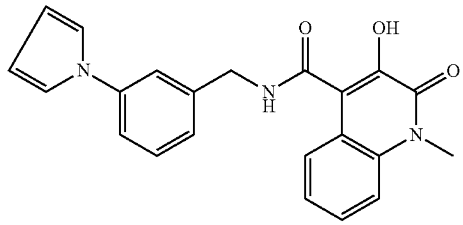 [SMILES: Cn1c(=O)c(O)c(C(=O)NCc2cccc(-n3cccc3)c2)c2ccccc21] | N-(3-(1H-pyrrol-1-yl)benzyl)-3-hydroxy-1-methyl-2-oxo-1,2-dihydroquinoline-4-carboxamide | 374.16/2.1 min | 91.7 |
| 173 | 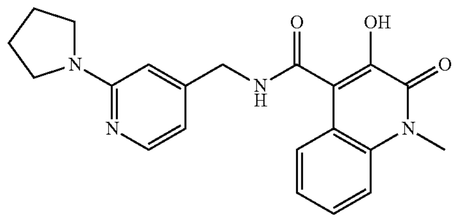 [SMILES: Cn1c(=O)c(O)c(C(=O)NCc2ccnc(N3CCCC3)c2)c2ccccc21] | 3-hydroxy-1-methyl-2-oxo-N-((2-(pyrrolidin-1-yl)pyridin-4-yl)methyl)-1,2-dihydroquinoline-4-carboxamide | 379.21/1.5 min | 98.7 |
| 174 | 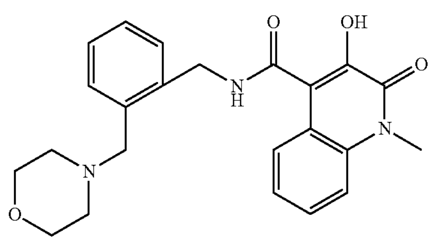 [SMILES: Cn1c(=O)c(O)c(C(=O)NCc2ccccc2CN2CCOCC2)c2ccccc21] | 3-hydroxy-1-methyl-N-(2-(morpholinomethyl)benzyl)-2-oxo-1,2-dihydroquinoline-4-carboxamide | 408.25/1.81 min | 96.7 |
| 175 | 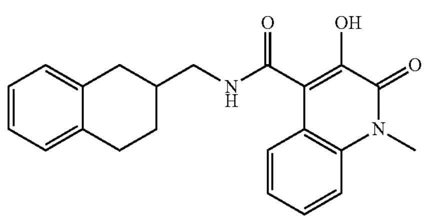 [SMILES: Cn1c(=O)c(O)c(C(=O)NCC2CCc3ccccc3C2)c2ccccc21] | 3-hydroxy-1-methyl-2-oxo-N-((1,2,3,4-tetrahydronaphthalen-2-yl)methyl)-1,2-dihydroquinoline-4-carboxamide | 363.2/2.21 min | 91.1 |
| 176 | 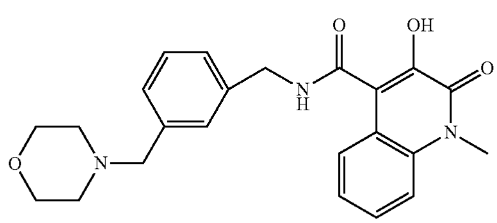 [SMILES: Cn1c(=O)c(O)c(C(=O)NCc2cccc(CN3CCOCC3)c2)c2ccccc21] | 3-hydroxy-1-methyl-N-(3-(morpholinomethyl)benzyl)-2-oxo-1,2-dihydroquinoline-4-carboxamide | 408.25/1.51 min | 98.9 |
| 177 | 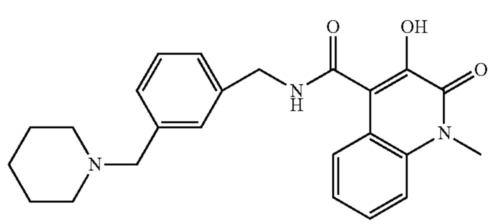 [SMILES: Cn1c(=O)c(O)c(C(=O)NCc2cccc(CN3CCCCC3)c2)c2ccccc21] | 3-hydroxy-1-methyl-2-oxo-N-(3-(piperidin-1-ylmethyl)benzyl)-1,2-dihydroquinoline-4-carboxamide | 406.27/1.27 min | 92.3 |

| Ex. # | Structure | Name | LC-MS [M + 1]/RT | Purity % |
|---|---|---|---|---|
| 178 | 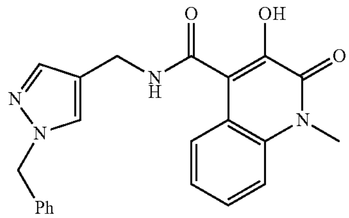 [SMILES: Cn1c(=O)c(O)c(C(=O)NCc2cnn(Cc3ccccc3)c2)c2ccccc21] | N-((1-benzyl-1H-pyrazol-4-yl)methyl)-3-hydroxy-1-methyl-2-oxo-1,2-dihydroquinoline-4-carboxamide | 389.18/1.67 min | 95.2 |
| 179 | 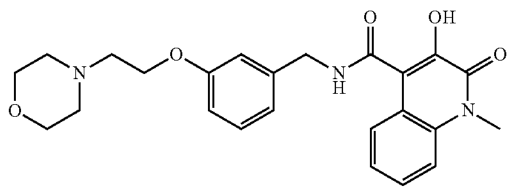 [SMILES: Cn1c(=O)c(O)c(C(=O)NCc2cccc(OCCN3CCOCC3)c2)c2ccccc21] | 3-hydroxy-1-methyl-N-(3-(2-morpholinoethoxy)benzyl)-2-oxo-1,2-dihydroquinoline-4-carboxamide | 438.25/1.6 min | 98.8 |
| 180 | 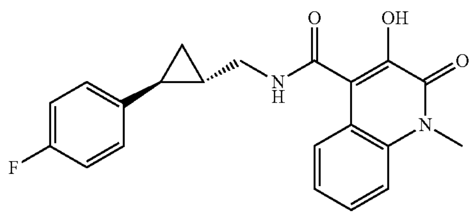 [SMILES: Cn1c(=O)c(O)c(C(=O)NC[C@H]2C[C@@H]2c2ccc(F)cc2)c2ccccc21] | 1:1 mixture of N-(((1S,2S)-2-(4-fluorophenyl)cyclopropyl)methyl)-3-hydroxy-1-methyl-2-oxo-1,2-dihydroquinoline-4-carboxamide and N-(((1R,2R)-2-(4-fluorophenyl)cyclopropyl)methyl)-3-hydroxy-1-methyl-2-oxo-1,2-dihydroquinoline-4-carboxamide | 367.18/2.1 min | 94.3 |
| 181 | 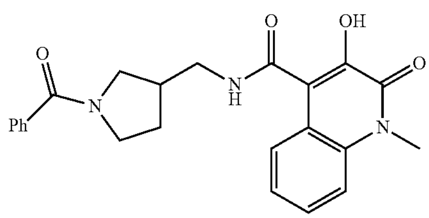 [SMILES: Cn1c(=O)c(O)c(C(=O)NCC2CCN(C(=O)c3ccccc3)C2)c2ccccc21] | N-((1-benzoylpyrrolidin-3-yl)methyl)-3-hydroxy-1-methyl-2-oxo-1,2-dihydroquinoline-4-carboxamide | 406.2/1.48 min | 98.2 |
| 182 | 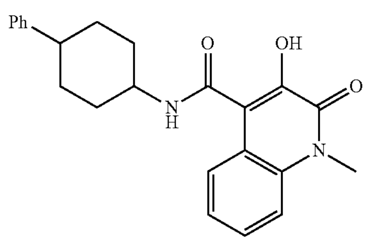 [SMILES: Cn1c(=O)c(O)c(C(=O)NC2CCC(c3ccccc3)CC2)c2ccccc21] | 3-hydroxy-1-methyl-2-oxo-N-(4-phenylcyclohexyl)-1,2-dihydroquinoline-4-carboxamide | 377.21/2.38 min | 96.4 |
| 183 | 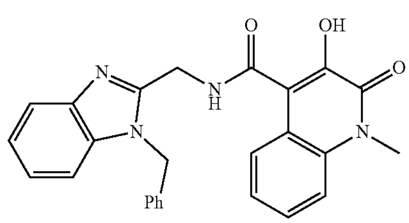 [SMILES: Cn1c(=O)c(O)c(C(=O)NCc2nc3ccccc3n2Cc2ccccc2)c2ccccc21] | N-((1-benzyl-1H-benzo[d]imidazol-2-yl)methyl)-3-hydroxy-1-methyl-2-oxo-1,2-dihydroquinoline-4-carboxamide | 439.23/1.99 min | 100.0 |
| 184 | 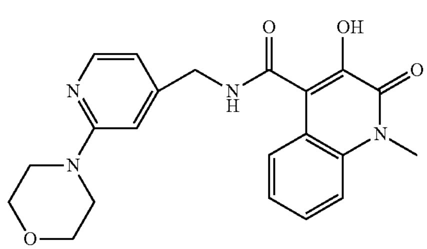 [SMILES: Cn1c(=O)c(O)c(C(=O)NCc2ccnc(N3CCOCC3)c2)c2ccccc21] | 3-hydroxy-1-methyl-N-((2-morpholinopyridin-4-yl)methyl)-2-oxo-1,2-dihydroquinoline-4-carboxamide | 395.22/1.41 min | 97.9 |

| Ex. # | Structure | Name | LC-MS [M + 1]/RT | Purity % |
|---|---|---|---|---|
| 185 | 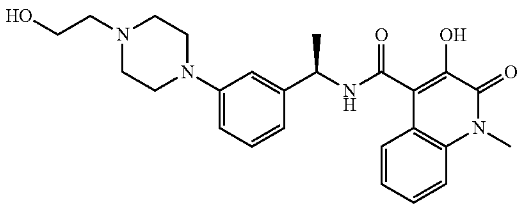 [SMILES: C[C@@H](NC(=O)c1c(O)c(=O)n(C)c2ccccc12)c1cccc(N2CCN(CCO)CC2)c1] | (R)-3-hydroxy-N-(1-(3-(4-(2-hydroxyethyl)piperazin-1-yl)phenyl)ethyl)-1-methyl-2-oxo-1,2-dihydroquinoline-4-carboxamide | 451.07/1.4 min | 90.6 |
| 186 | 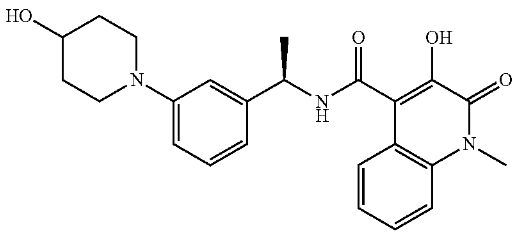 [SMILES: C[C@@H](NC(=O)c1c(O)c(=O)n(C)c2ccccc12)c1cccc(N2CCC(O)CC2)c1] | (R)-3-hydroxy-N-(1-(3-(4-hydroxypiperidin-1-yl)phenyl)ethyl)-1-methyl-2-oxo-1,2-dihydroquinoline-4-carboxamide | 422.07/1.56 min | 91.0 |
| 187 | 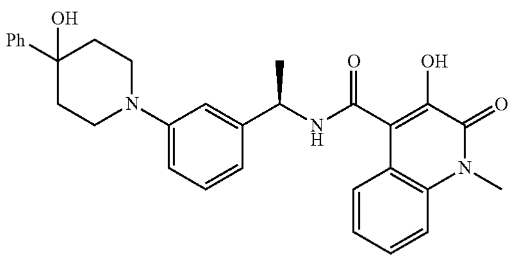 [SMILES: C[C@@H](NC(=O)c1c(O)c(=O)n(C)c2ccccc12)c1cccc(N2CCC(O)(c3ccccc3)CC2)c1] | (R)-3-hydroxy-N-(1-(3-(4-hydroxy-4-phenylpiperidin-1-yl)phenyl)ethyl)-1-methyl-2-oxo-1,2-dihydroquinoline-4-carboxamide | 498.04/2.21 min | 90.6 |
| 188 | 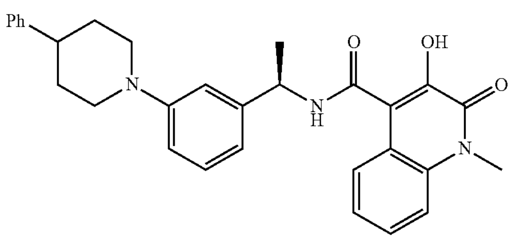 [SMILES: C[C@@H](NC(=O)c1c(O)c(=O)n(C)c2ccccc12)c1cccc(N2CCC(c3ccccc3)CC2)c1] | (R)-3-hydroxy-1-methyl-2-oxo-N-(1-(3-(4-phenylpiperidin-1-yl)phenyl)ethyl)-1,2-dihydroquinoline-4-carboxamide | 482.06/2.88 min | 88.4 |
| 189 | 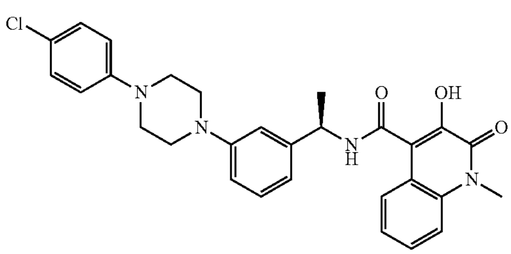 [SMILES: C[C@@H](NC(=O)c1c(O)c(=O)n(C)c2ccccc12)c1cccc(N2CCN(c3ccc(Cl)cc3)CC2)c1] | (R)-N-(1-(3-(4-(4-chlorophenyl)piperazin-1-yl)phenyl)ethyl)-hydroxy-1-methyl-2-oxo-1,2-dihydroquinoline-4-carboxamide | 515.08/2.67 min | 88.7 |
| 190 | 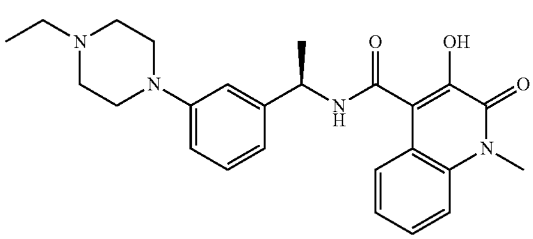 [SMILES: CCN1CCN(c2cccc([C@@H](C)NC(=O)c3c(O)c(=O)n(C)c4ccccc34)c2)CC1] | (R)-N-(1-(3-(4-ethylpiperazin-1-yl)phenyl)ethyl)-3-hydroxy-1-methyl-2-oxo-1,2-dihydroquinoline-4-carboxamide | 435.09/1.48 min | 92.5 |

| Ex. # | Structure | Name | LC-MS [M + 1]/RT | Purity % |
|---|---|---|---|---|
| 191 | 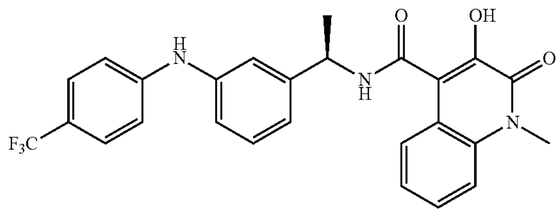 [SMILES: C[C@@H](NC(=O)c1c(O)c(=O)n(C)c2ccccc12)c1cccc(Nc2ccc(C(F)(F)F)cc2)c1] | C2(R)-3-hydroxy-1-methyl-2-oxo-N-(1-(3-(4-(trifluoromethyl)phenylamino)phenyl)ethyl)-1,2-dihydroquinoline-4-carboxamide | 481.98/2.63 min | 90.8 |

Example 192

(R)-3-hydroxy-1-methyl-2-oxo-N-(6-(trifluoromethyl)-2,3-dihydro-1H-inden-1-yl)-1,2-dihydroquinoline-4-carboxamide

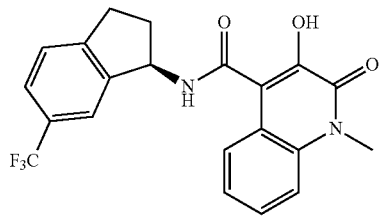 [SMILES: Cn1c(=O)c(O)c(C(=O)N[C@@H]2CCc3ccc(C(F)(F)F)cc32)c2ccccc21]

Following the procedure described for Example 3, Example 192 (4 mg, 9.94 μmol, 20% yield) was prepared as an off-white powder by using 3-hydroxy-1-methyl-2-oxo-1,2-dihydroquinoline-4-carbonyl chloride (see Example 3C) and (R)-6-(trifluoromethyl)-2,3-dihydro-1H-inden-1-amine (Intermediate 15). LCMS=2.07 min, [M+1]=403.1 (Method A); Orthogonal HPLC (150×4.6 mm 3.5 μm, 254 nm): Sunfire {RT=9.47 min, 98%}; Xbridge {RT=8.63 min, 92%}. $^1$H NMR (500 MHz, MeOD) δ ppm 7.80 (1 H, s), 7.64 (1 H, d, J=8.3 Hz), 7.48-7.57 (3 H, m), 7.44 (1H, d, J=8.0 Hz), 7.31 (1 H, t, J=7.4 Hz), 5.76 (1 H, t, J=7.4 Hz), 3.81 (3 H, s), 3.08-3.18 (1 H, m), 2.98-3.06 (1 H, m), 2.67-2.74 (1 H, m), 2.05-2.13 (1 H, m).

Example 193

N-(3-(3,4-dichlorophenyl)propyl)-1-methyl-3-(methylamino)-2-oxo-1,2-dihydroquinoline-4-carboxamide

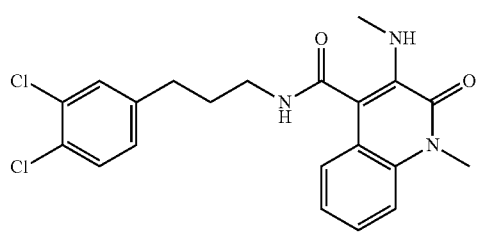 [SMILES: CNc1c(C(=O)NCCCc2ccc(Cl)c(Cl)c2)c2ccccc2n(C)c1=O]

Example 193A 4-(3-(3,4-dichlorophenyl)propylcarbamoyl)-1-methyl-2-oxo-1,2-dihydroquinolin-3-yltrifluoromethanesulfonate To a solution of N-(3-(3,4-dichlorophenyl)propyl)-3-hydroxy-1-methyl-2-oxo-1,2-dihydroquinoline-4-carboxamide (Example 3, 180 mg, 0.44 mmol) in DCM (1 mL) was added DMAP (54.3 mg, 0.444 mmol), trifluoromethanesulfonic anhydride (251 mg, 0.89 mmol) followed by pyridine (0.11 mL, 1.33 mmol). The reaction mixture was stirred at rt for 16 h then diluted with DCM, washed with H$_2$O, and the organic layer was dried over MgSO$_4$, filtered and concentrated in vacuum. The residue was purified by ISCO chromatography on a 12 g cartridge using Hexanes/EtOAc:MeOH (10:1) (0-100% over 15 min, flow rate 40 mL/min) to give Example 193A as a pale yellow solid. (61 mg, 26% yield). LCMS ESI 537.0 (M+H), RT=2.17 min (Method B).

Example 193

To a solution of Example 193A (15 mg, 0.028 mmol) in dioxane (0.3 mL) and EtOH (0.5 mL) was added methanamine (250 μl, 0.028 mmol). The reaction mixture was stirred under microwave irradiation at 120° C. for 60 min, then purified by HPLC using a 10 minute gradient from 0 to 100% B (Column: PHENOMENEX® Luna Axia 100×20 mm 5 μm (10 min gradient); Solvent A: 10% ACN—90% H$_2$O—0.1% TFA; Solvent B: 90% ACN—10% H$_2$O—0.1% TFA). Example 193 (7 mg, 60% yield) was isolated. $^1$H NMR (400 MHz, MeOD) δ ppm 7.40-7.49 (4 H, m), 7.33 (1 H, td, J=7.8, 1.3 Hz), 7.15-7.26 (2 H, m), 3.74-3.79 (3 H, m), 3.73-3.81 (3 H, m), 3.39-3.49 (2 H, m), 3.02 (3 H, s), 2.66-2.79 (2 H, m), 1.85-2.07 (2 H, m). LCMS ESI 418.1 (M+H) RT=2.08 min (Method B); Orthogonal HPLC (150×4.6 mm 3.5 μm, 254 nm): Sunfire {RT=10.6 min, 98%}; Xbridge {RT=9.5 min, 96%}.

Examples 194-199 were synthesized following the procedure described for Example 193.

| Ex. # | Structure | Name | LC-MS [M + 1]/RT | Purity |
|---|---|---|---|---|
| 194 | 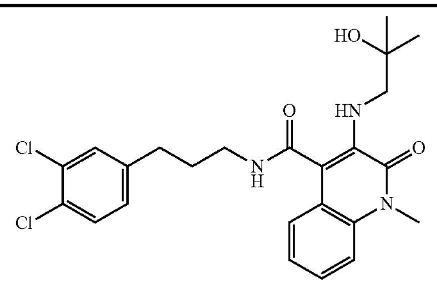 | N-(3-(3,4-dichlorophenyl)propyl)-3-(2-hydroxy-2-methylpropylamino)-1-methyl-2-oxo-1,2-dihydroquinoline-4-carboxamide | 476/2.09 min (Method B) | RT = 10.4 min, 95% (Method A) RT = 9.3 min, 94% (Method B) |
| 195 | 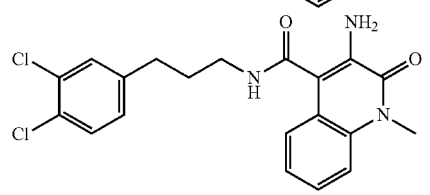 | 3-amino-N-(3-(3,4-dichlorophenyl)propyl)-1-methyl-2-oxo-1,2-dihydroquinoline-4-carboxamide | 404/2.07 min (Method B) | RT = 10.3 min, 99% (Method A) RT = 9.3 min, 98% (Method B) |
| 196 | 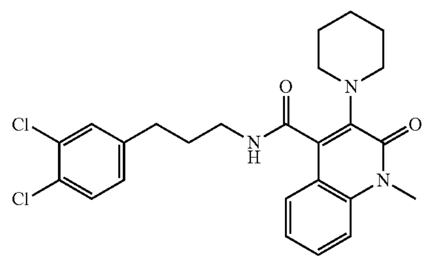 [SMILES: Cn1c(=O)c(N2CCCCC2)c(C(=O)NCCCc2ccc(Cl)c(Cl)c2)c2ccccc21] | N-(3-(3,4-dichlorophenyl)propyl)-1-methyl-2-oxo-3-(piperidin-1-yl)-1,2-dihydroquinoline-4-carboxamide | 472/2.25 min (Method B) | RT = 11.2 min, 99% (Method A) RT = 9.95 min, 98.8% (Method B) |
| 197 | 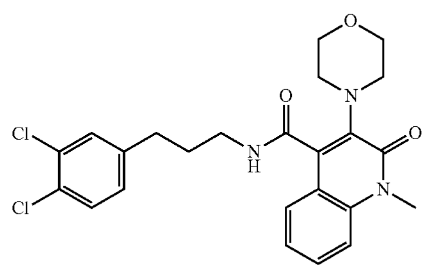 [SMILES: Cn1c(=O)c(N2CCOCC2)c(C(=O)NCCCc2ccc(Cl)c(Cl)c2)c2ccccc21] | N-(3-(3,4-dichlorophenyl)propyl)-1-methyl-3-morpholino-2-oxo-1,2-dihydroquinoline-4-carboxamide | 474/2.08 min (Method B) | RT = 10.2 min, 97% (Method A) RT = 9.15 min, 96% (Method B) |
| 198 | 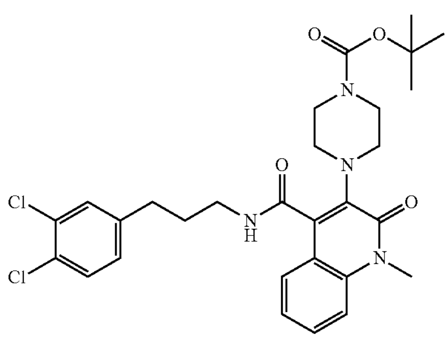 [SMILES: Cn1c(=O)c(N2CCN(C(=O)OC(C)(C)C)CC2)c(C(=O)NCCCc2ccc(Cl)c(Cl)c2)c2ccccc21] | tert-butyl 4-(4-(3-(3,4-dichlorophenyl)propylcarbamoyl)-1-methyl-2-oxo-1,2-dihydroquinolin-3-yl)piperazine-1-carboxylate | 573/2.25 min (Method B) | RT = 11.2 min, 99% (Method A) RT = 9.95 min, 99% (Method B) |
| 199 | 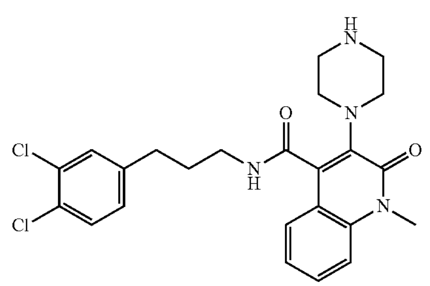 [SMILES: Cn1c(=O)c(N2CCNCC2)c(C(=O)NCCCc2ccc(Cl)c(Cl)c2)c2ccccc21] | N-(3-(3,4-dichlorophenyl)propyl)-1-methyl-2-oxo-3-(piperazin-1-yl)-1,2-dihydroquinoline-4-carboxamide | 446.1/2.10 min (Method B) | RT = 6.41 min, 90% (Method A) RT = 7.52 min, 94 % (Method B) |

Example 200

3-cyano-N-(3-(3,4-dichlorophenyl)propyl)-1-methyl-2-oxo-1,2-dihydroquinoline-4-carboxamide

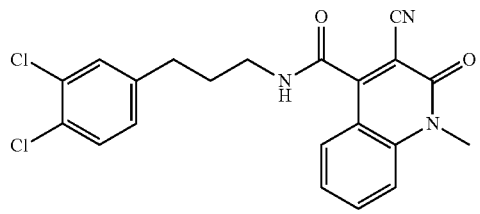 [SMILES: Cn1c(=O)c(C#N)c(C(=O)NCCCc2ccc(Cl)c(Cl)c2)c2ccccc21]

To a solution of 4-(3-(3,4-dichlorophenyl)propylcarbamoyl)-1-methyl-2-oxo-1,2-dihydroquinolin-3-yl trifluoromethanesulfonate (30 mg, 0.056 mmol), prepared as described in Example 197A, in DMF (1 mL) was added zinc cyanide (13 mg, 0.112 mmol) and tetrakis(triphenylphosphine)palladium(0) (13 mg, 0.011 mmol). The reaction mixture was stirred under microwave irradiation at 120° C. for 60 min. Example 200 (4 mg, 17% yield) was isolated by HPLC (CH$_3$CN/H$_2$O/TFA). $^1$H NMR (500 MHz, MeOD) δ ppm 8.70 (1 H, dd, J=8.3, 1.4 Hz), 7.85-7.89 (1 H, m), 7.69-7.73 (1 H, m), 7.48 (1 H, t, J=7.3 Hz), 7.37-7.43 (1 H, m), 7.31 (1 H, d, J=1.9 Hz), 7.20-7.25 (1 H, m), 7.10 (1H, dd, J=8.3, 1.9 Hz), 3.80-3.83 (3 H, m), 3.73 (2 H, t, J=6.6 Hz), 2.71 (2 H, t, J=7.0 Hz), 2.11 (2 H, t, J=6.9 Hz). LCMS ESI 415.1 (M+H) RT=2.18 min (Method B); Orthogonal HPLC (150×4.6 mm 3.5 μm, 254 nm): Sunfire {RT=11.7 min, 93%}; Xbridge {RT=10.5 min, 90%}.

Example 201

3-hydroxy-1-methyl-2-oxo-N-(cis-4-phenylcyclohexyl)-1,2-dihydroquinoline-4-carboxamide

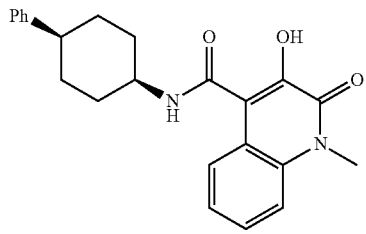 [SMILES: Cn1c(=O)c(O)c(C(=O)N[C@H]2CC[C@@H](c3ccccc3)CC2)c2ccccc21]

Following the same procedure as described for Example 3, Example 201 (18 mg, 0.048 mmol, 29% yield) was prepared as an off-white powder by using 3-hydroxy-1-methyl-2-oxo-1,2-dihydroquinoline-4-carbonyl chloride and cis-1,4-phenylcyclohexanamine LCMS=1.99 min, [M+1]=377.1 (Method A); Orthogonal HPLC (150×4.6 mm 3.5 μm, 254 nm): Sunfire {RT=9.73 min, 92%}; Xbridge {RT=8.85 min, 92.3%}. $^1$H NMR (500 MHz, chloroform-d) δ ppm 8.16-8.20 (1 H, m), 7.50 (1 H, t, J=7.4 Hz), 7.38 (1 H, d, J=8.3 Hz), 7.33-7.36 (1H, m), 7.30 (2 H, t, J=7.6 Hz), 7.18-7.24 (3 H, m), 4.49 (1H, br. s.), 3.83 (3 H, s), 2.64 (1 H, t, J=11.4 Hz), 2.12 (2 H, d, J=12.1 Hz), 1.80-1.90 (4 H, m), 1.74 (2 H, t, J=12.4 Hz).

Example 202

3-hydroxy-1-methyl-2-oxo-1,2-dihydro-quinoline-4-carboxylic acid [4-(cis-4-fluoro-phenyl)-trans-4-methoxy-cyclohexyl]-amide

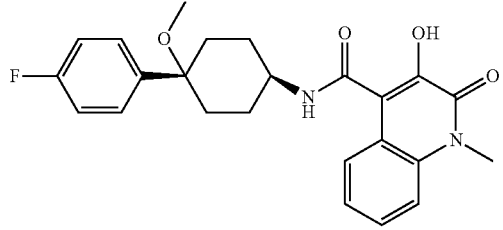 [SMILES: CO[C@]1(c2ccc(F)cc2)CC[C@@H](NC(=O)c2c(O)c(=O)n(C)c3ccccc23)CC1]

To 3-hydroxy-1-methyl-2-oxo-1,2-dihydroquinoline-4-carbonyl chloride (21 mg, 0.090 mmol) in CH$_2$Cl$_2$ (0.5 mL) at 0° C. was added Intermediate 31 (10 mg, 0.045 mmol). The mixture was stirred at rt for 2.5 h and then concentrated under reduced pressure. The residue was dissolved in MeOH and purified by RPHPLC (ACN/H$_2$O/TFA, 0-80% B over 12 min) Example 202 (13 mg, 0.031 mmol, 68% yield) was isolated as a white solid after drying. LCMS=1.94 min [M+1]=425.3 (Method B); Orthogonal HPLC (150×4.6 mm 3.5 μm, 254 nm): Sunfire {RT=9.07 min, 98.4%}; Xbridge {RT=8.25 min, 98.4%). $^1$H NMR (400 MHz, acetone-d$_6$ppm 7.68-7.78 (2 H, m), 7.42-7.54 (4 H, m), 7.25-7.30 (1 H, m), 7.05-7.12 (2 H, m), 4.32-4.39 (1 H, m), 3.77 (3 H, s), 2.95 (3 H, s), 2.17-2.27 (2 H, m), 2.07-2.14 (2 H, m), 1.90 (2 H, d, J=13.19 Hz), 1.84 (1 H, d, J=3.85 Hz), 1.77-1.83 (1 H, m).

Example 203

N-(4-(4-fluorophenyl)cyclohex-3-enyl)-3-hydroxy-1-methyl-2-oxo-1,2-dihydroquinoline-4-carboxamide

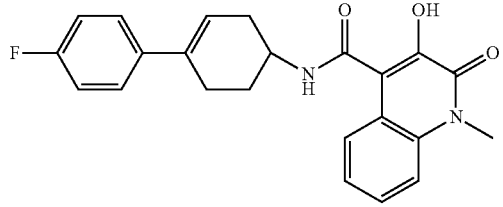 [SMILES: Cn1c(=O)c(O)c(C(=O)NC2CC=C(c3ccc(F)cc3)CC2)c2ccccc21]

To a solution of Example 201 (7 mg, 0.016 mmol) and tetrabutylammonium iodide (24.37 mg, 0.066 mmol) in CH$_2$Cl$_2$ (0.5 mL) at −50° C. was added boron trichloride (0.025 mL, 0.025 mmol). The reaction mixture was stirred at rt for 1 h. The mixture was quenched with MeOH, concentrated and the residue was purified by HPLC (ACN/water/TFA, 5-90% B over 15 min), then by HPLC (MeOH/water/TFA, 0-100% B over 10 min). Example 203 was isolated as a white solid (1.81 mg, 4.61 μmol, 28.0% yield). LCMS=393.3 [M+Na] RT=1.98 min (Method B). Orthogonal HPLC RT=9.67 min, 100% (Method A); RT=8.84 min, 100% (Method B). $^1$H NMR (400 MHz, acetone) d ppm 7.78 (1H, d, J=8.08 Hz), 7.54 (1 H, br. s.), 7.42-7.54 (3 H, m), 7.24-7.35 (1 H, m), 6.96-7.13 (2 H, m), 6.09 (1 H, br. s.), 4.30-4.46 (1 H, m), 3.79 (3 H, s), 2.57-2.77 (3 H, m), 2.35 (1 H, d, J=3.03 Hz), 2.12-2.24 (1 H, m), 1.87-2.02 (1 H, m).

Example 204

(R)-benzyl 4-(3-(1-(3-hydroxy-1-methyl-2-oxo-1,2-dihydroquinoline-4-carboxamido)ethyl)phenyl)piperazine-1-carboxylate

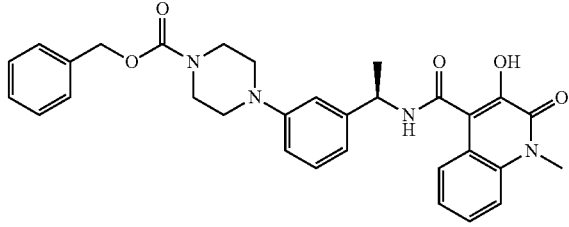 [SMILES: C[C@@H](NC(=O)c1c(O)c(=O)n(C)c2ccccc12)c1cccc(N2CCN(C(=O)OCc3ccccc3)CC2)c1]

Following the same procedure as described for Example 3, Example 204 (12 mg, 0.022 mmol, 25% yield) was prepared as an off-white powder by using 3-hydroxy-1-methyl-2-oxo-1,2-dihydroquinoline-4-carbonyl chloride and (R)-benzyl 4-(3-(1-aminoethyl)phenyl)piperazine-1-carboxylate (Intermediate 33). LC-MS (ESI) m/z 541 (M+H), RT=1.64 min (Method C). Orthogonal HPLC (150×4.6 mm 3.5 μm, 254 nm): Sunfire {RT=8.9 min, 95%}; Xbridge {RT=8.5 min, 93%}. $^1$H NMR (500 MHz, MeOD) δ ppm 7.55 (1 H, d, J=7.7 Hz), 7.46-7.50 (2 H, m), 7.36-7.41 (4 H, m), 7.30-7.34 (3 H, m), 7.26 (1 H, s), 7.22-7.24 (1 H, m), 7.13 (1 H, d, J=7.7 Hz), 7.03 (1 H, dd, J=8.1, 2.1 Hz), 5.28 (1 H, d, J=7.2 Hz), 5.17 (2 H, s), 3.82 (3H, s), 3.71 (4 H, d, J=3.6 Hz), 3.29 (4 H, d, J=5.5 Hz), 1.55 (3 H, d, J=7.2 Hz).

Example 205

(S)-benzyl 4-(3-(1-(3-hydroxy-1-methyl-2-oxo-1,2-dihydroquinoline-4-carboxamido)ethyl)phenyl)piperazine-1-carboxylate

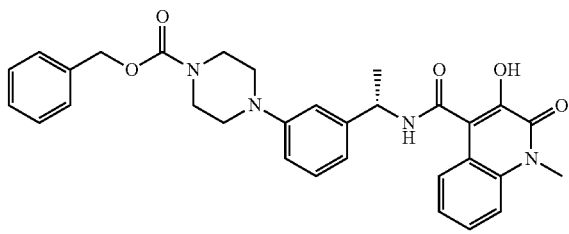 [SMILES: C[C@H](NC(=O)c1c(O)c(=O)n(C)c2ccccc12)c1cccc(N2CCN(C(=O)OCc3ccccc3)CC2)c1]

Following the same procedure as described for Example 3, Example 205 was prepared as an off-white powder by using 3-hydroxy-1-methyl-2-oxo-1,2-dihydroquinoline-4-carbonyl chloride and (S)-benzyl 4-(3-(1-aminoethyl)phenyl)piperazine-1-carboxylate (Intermediate 34). LC-MS (ESI) m/z 541 (M+H), RT=2.00 min (Method B). Orthogonal HPLC (150×4.6 mm 3.5 μm, 254 nm): Sunfire {RT=8.9 min, 93%}; Xbridge {RT=8.5 min, 92%}.

What is claimed is:
1. A compound of Formula (I):

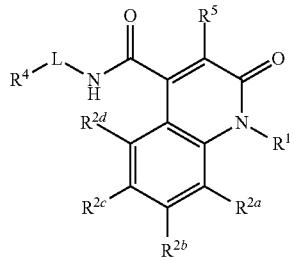

or a stereoisomer, a tautomer, or a pharmaceutically acceptable salt thereof, wherein:
  $R^1$ is independently selected from the group consisting of: H, $C_{1-6}$ alkyl substituted with 0-3 $R^a$, $C_{2-6}$ alkenyl substituted with 0-3 $R^a$, and —$(CH_2)$—W—$(CH_2)_m$—$R^{1a}$;
  W is independently selected from the group consisting of: a bond, NH, O, S, N($C_{1-4}$ alkyl), CO, CONH, CON($C_{1-4}$ alkyl), NHCO, SO$_2$, NHSO$_2$, SO$_2$NH, NHCO$_2$, and CHR$^f$;
  $R^{1a}$ is independently selected from the group consisting of: $C_{3-10}$ carbocycle and a 5- to 10-membered heterocycle comprising: carbon atoms and 1-4 heteroatoms selected from N, NR$^e$, O, and S(O)$_p$; and wherein said carbocycle and heterocycle are substituted with 0-3 $R^c$;
  $R^{2a}$, $R^{2b}$, $R^{2c}$, and $R^{2d}$ are, independently at each occurrence, selected from the group consisting of: H, halogen, OH, $C_{1-4}$ alkyl, $C_{1-2}$ alkenyl, $C_{1-4}$ haloalkyl, $C_{1-4}$ alkoxy, $C_{1-4}$ haloalkoxy, CF$_3$, OCF$_3$, OCF$_2$CHF$_2$, CN, NH$_2$, NO$_2$, NH($C_{1-4}$ alkyl), N($C_{1-4}$ alkyl)$_2$, CO$_2$H, CO$_2$($C_{1-4}$ alkyl), CONH$_2$, CONH($C_{1-4}$ alkyl), CON($C_{1-4}$ alkyl)$_2$, NHSO$_2$($C_{1-4}$ alkyl), SO$_2$($C_{1-4}$ alkyl), SO$_2$NH$_2$, and phenyl substituted with 0-2 $R^b$;
  $R^4$ is independently selected from the group consisting of: $C_{3-10}$ carbocycle and a 5- to 10-membered heterocycle comprising: carbon atoms and 1-4 heteroatoms selected from N, NR$^e$, O, and S(O)$_p$; wherein said carbocycle and heterocycle are substituted with 0-3 $R^d$;
  $R^5$ is independently selected from the group consisting of: OR$^6$, CN, and NR$^7$R$^8$;
  $R^6$ is independently selected from the group consisting of: H and $C_{1-6}$ alkyl substituted with 0-1 CO$_2$H;
  $R^7$ is independently selected from the group consisting of: H, $C_{1-6}$ alkyl substituted with 0-1 R$^a$, —$(CH_2)_n$-(phenyl substituted with 0-3 R$^b$), and —$(CH_2)_n$-(5- to 6-membered heterocycle comprising: carbon atoms and 1-4 heteroatoms selected from N, NR$^e$, O, and S(O)$_p$); and wherein said heterocycle is substituted with 0-3 R$^c$;
  $R^8$ is independently selected from the group consisting of: H and $C_{1-6}$ alkyl;
  alternatively, NR$^7$R$^8$ is a 5- to 6-membered heterocycle comprising: carbon atoms and 1-4 heteroatoms selected from N, NR$^e$, O, and S(O)$_p$;
  L is independently a hydrocarbon or hydrocarbon-heteroatom linker optionally substituted with 0-2 R$^g$; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —SO$_2$—, NH, and N($C_{1-4}$ alkyl);
  alternatively, L is X$_1$—Y—X$_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-2 $R^g$; said hydrocarbon linker has one to six carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-10}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

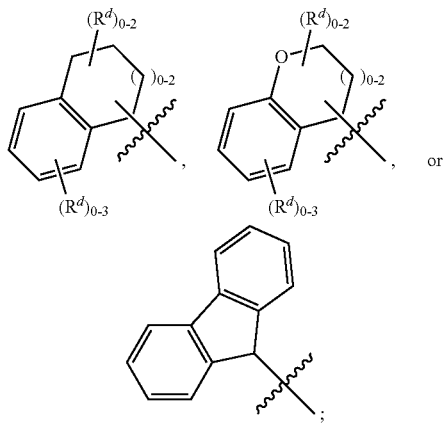

, or $R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, NH($C_{1-4}$ alkyl), N($C_{1-4}$ alkyl)$_2$, $CO_2H$, $CO_2$($C_{1-4}$ alkyl), NHCO($C_{1-4}$ alkyl substituted with 0-1 $NH_2$), N($C_{1-4}$ alkyl)CO($C_{1-4}$ alkyl), $NHCO_2$($C_{1-4}$ alkyl), $CONHSO_2$($C_{1-4}$ alkyl), $SO_2$($C_{1-4}$ alkyl), $CONH_2$, CONH($C_{1-4}$ alkyl), $NHSO_2$($C_{1-4}$ alkyl), N($C_{1-4}$ alkyl)$SO_2$($C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, NH($C_{1-4}$alkyl), N($C_{1-4}$alkyl)$_2$, $CO_2H$, $CO_2$($C_{1-4}$ alkyl), $CONH_2$, CONH($C_{1-4}$ alkyl), CON($C_{1-4}$ alkyl)$_2$, $NHCO_2$($C_{1-4}$ alkyl), $NHSO_2$($C_{1-4}$ alkyl), N($C_{1-4}$ alkyl)$SO_2$($C_{1-4}$ alkyl), $SO_2$($C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-10H, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, NH($C_{1-4}$ alkyl), N($C_{1-4}$ alkyl)$_2$, $CO_2H$, $CO_2$($C_{1-4}$ alkyl), CO($C_{1-4}$ alkyl), NHCO($C_{1-4}$ alkyl), —$CH_2NHCO$($C_{1-4}$ alkyl), $CONH_2$, CONH($C_{1-4}$ alkyl), CON($C_{1-4}$alkyl)$_2$, $SO_2$($C_{1-4}$alkyl), $SO_2NH_2$, —$SO_2NH$($C_{1-4}$ alkyl), —$SO_2NH$($C_{3-6}$ cycloalkyl), —$NHSO_2$($C_{1-4}$ alkyl), —$CH_2NHSO_2$($C_{1-4}$ alkyl), Si($C_{1-4}$ alkyl)$_3$, and phenyl optionally substituted with one or two substituents independently selected from: halogen, OH, $C_{1-4}$ alkyl, $C_{1-4}$ haloalkyl, $C_{1-4}$ alkyoxy, and NHCO($C_{1-4}$ alkyl);

$R^e$ is, independently at each occurrence, selected from the group consisting of: H, $C_{1-4}$ alkyl, CO($C_{1-4}$ alkyl), $CO_2$ ($C_{1-4}$ alkyl), $CO_2$(benzyl), and —$(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2$($C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2$($C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4; and p is, independently at each occurrence, selected from 0, 1, and 2;

provided that: when L is $CH_2$, $R^1$ is H and $R^5$ is OH, then $R^4$ is other than an unsubstituted phenyl.

2. A compound according to claim 1, wherein:

$R^1$ is independently selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is independently selected from the group consisting of: a bond, NH, N($C_{1-4}$ alkyl), CO, CONH, CON($C_{1-4}$ alkyl), $SO_2$, $NHCO_2$, and $CHR^f$;

$R^{1a}$ is independently selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^{2a}$, $R^{2b}$ and $R^{2c}$ are, independently at each occurrence, selected from the group consisting of: H, halogen, OH, $C_{1-4}$ alkyl, $C_{1-2}$ alkenyl, $C_{1-4}$ haloalkyl, $C_{1-4}$ alkoxy, $CF_3$, $OCF_3$, $OCF_2CHF_2$, $OCH_2CF_3$, $OCF_2CF_3$, $OCH_2CF_2F_3$, $NH_2$, $NO_2$, NH($C_{1-4}$ alkyl), N($C_{1-4}$ alkyl)$_2$, $CO_2H$, $CO_2$($C_{1-4}$ alkyl), $CONH_2$, CONH($C_{1-4}$ alkyl), CON($C_{1-4}$ alkyl)$_2$, $NHSO_2$($C_{1-4}$ alkyl), $SO_2$($C_{1-4}$ alkyl), $SO_2NH_2$, and phenyl substituted with 0-2 $R^b$;

$R^{2d}$ is independently selected from the group consisting of: H, halogen, OH, $C_{1-4}$ alkyl, and $NH_2$;

$R^4$ is independently selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is independently selected from the group consisting of: OH, O($C_{1-4}$ alkyl substituted with 0-1 $CO_2H$), CN, and $NR^7R^8$;

L is independently a hydrocarbon or hydrocarbon-heteroatom linker optionally substituted with 0-1 $R^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —$SO_2$—, NH, and N($C_{1-4}$ alkyl);

alternatively, L is $X_1$—Y—$X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-7}$ carbocycle and a 4- to 10-membered heterocycle comprising: carbon atoms and 1-4 heteroatoms selected from N, $NR^e$, O, and $S(O)_p$; wherein each said carbocycle and heterocycle may be optionally substituted with one, two or three substituents independently selected from: halogen, OH, $C_{1-4}$ alkyl, $C_{1-4}$ haloalkyl, and $C_{1-4}$ alkyoxy;

alternatively, $R^4$-L- is

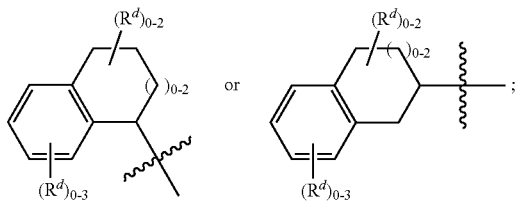

provided that: when L is $CH_2$, $R^1$ is H and $R^5$ is OH, then $R^4$ is other than an unsubstituted phenyl.

3. A compound according to claim 2, wherein:

$R^1$ is independently selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is independently selected from the group consisting of: a bond, CO, CONH, CON($C_{1-4}$ alkyl), $SO_2$, and $CHR^f$;

$R^{1a}$ is independently selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

L is independently a hydrocarbon or hydrocarbon-heteroatom linker optionally substituted with 0-1 $R^g$; wherein said hydrocarbon linker has one to four carbon atoms and may be straight or branched, saturated or unsaturated; and said hydrocarbon-heteroatom linker has one to four carbon atoms and one group selected from O, S, —SO—, and —$SO_2$—;

alternatively, L is $X_1$—Y—$X_2$;

$X_1$, and $X_2$ are, independently at each occurrence, selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —$SO_2$—, NH, and N($C_{1-4}$ alkyl);

Y is independently selected from the group consisting of: $C_{3-6}$ cycloalkylene, $C_{4-6}$ cycloalkenylene, phenylene, pyridylene, azetidinylene, pyrrolidinylene, piperidinylene, pyrazolylene, thiazolylene, oxadiazolylene, imidazolylene, and benzimidazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy.

4. A compound according to claim 3, wherein the compound is of Formula (II):

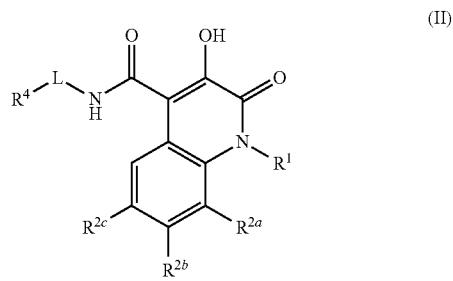

(II)

or a stereoisomer, a tautomer, or a pharmaceutically acceptable salt thereof, within the scope of any of the above aspects, wherein:

$R^1$ is independently selected from the group consisting of: H, $C_{1-4}$ alkyl substituted with 0-1 $R^a$, —$(CH_2)_{0-1}$CH$(CH_3)$-(phenyl substituted with 0-2 $R^b$), —$(CH_2)_{0-2}$-(phenyl substituted with 0-3 $R^b$), and —$(CH_2)_{0-2}$-(5- to 6-membered heterocycle comprising: carbon atoms and 1-4 heteroatoms selected from N, $NR^e$, O, and $S(O)_p$); and wherein said heterocycle is substituted with 0-2 $R^c$;

$R^{2a}$, $R^{2b}$, and $R^{2c}$ are, independently at each occurrence, selected from the group consisting of: H, halogen, $CF_3$, $OCF_3$, $OCF_2CHF_2$, $OCH_2CF_3$, $OCF_2CF_3$, $OCH_2CF_2CF_3$, CN, $NH_2$, $NO_2$, $CONH_2$, $C_{1-4}$ alkyl, $C_{1-2}$ alkenyl, $C_{1-4}$ alkoxy, and phenyl substituted with 0-2 $R^c$; and $R^4$ is independently selected from: phenyl, naphthyl, tetrahydronaphthyl, dihydroindenyl, pyrrolidinyl, thienyl, pyrrolyl, pyrazolyl, imidazolyl, 1,2,3-thiadiazolyl, 1,2,4-oxadiazolyl, piperidinyl, piperazinyl, morpholinyl, indolinyl, quinolinyl, and benzimidazolyl; wherein each moiety is substituted with 0-2 $R^d$;

alternatively, $R^4$-L- is

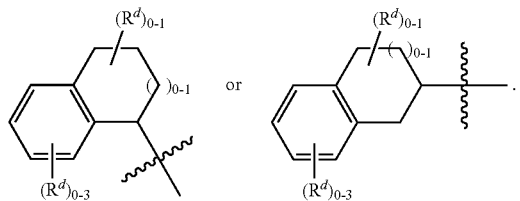

5. A compound according to claim 4, wherein:

$R^1$ is independently selected from the group consisting of: H, $C_{1-4}$ alkyl, —$CH_2CO_2$($C_{1-4}$ alkyl), phenyl, 4-halophenyl, benzyl, 4-$CO_2$H-benzyl, 4-$SO_2$($C_{1-4}$ alkyl)-benzyl, 2-($C_{1-4}$ alkoxy)-5-halo-benzyl, 2-halo-phenethyl, 2-OH-phenethyl;

$R^{2a}$, $R^{2b}$, and $R^{2c}$ are, independently at each occurrence, selected from the group consisting of: H, halogen, $CF_3$, $OCF_3$, CN, $NH_2$, $NO_2$, $CONH_2$, $C_{1-4}$ alkyl, $C_{1-2}$ alkenyl, $C_{1-4}$ alkoxy, and phenyl substituted with 0-2 $R^c$;

$R^4$ is independently selected from: phenyl, naphthyl, tetrahydronaphthyl, pyrrolidinyl, thienyl, pyrrolyl, pyrazolyl, imidazolyl, 1,2,3-thiadiazolyl, 1,2,4-oxadiazolyl, tetrazolyl, piperidinyl, piperazinyl, morpholinyl, indolyl, indolinyl, and benzimidazolyl; wherein each moiety is substituted with 0-2 $R^d$;

L is independently a hydrocarbon or hydrocarbon-heteroatom linker optionally substituted with 0-1 $R^g$; wherein said hydrocarbon linker has one to six carbon atoms and may be straight or branched, and saturated or unsaturated; and said hydrocarbon-heteroatom linker has one to six carbon atoms and one group selected from O, —CO—, S, —SO—, —SO$_2$—, NH, and N(C$_{1-4}$ alkyl); alternatively, L is X$_1$—Y—X$_2$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to four carbon atoms and may be saturated or unsaturated; and said hydrocarbon-heteroatom linker has zero to three carbon atoms and one group selected from O, —CO—, S, —SO—, —SO$_2$—, NH, and N(C$_{1-4}$ alkyl);

$X_2$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker has one to five carbon atoms and may be saturated or unsaturated; and said hydrocarbon-heteroatom linker has zero to four carbon atoms and one group selected from O, —CO—, S, —SO—, —SO$_2$—, NH, and N(C$_{1-4}$ alkyl); and Y is independently selected from the group consisting of: $C_{3-6}$ cycloalkylene, $C_{4-6}$ cycloalkenylene, phenylene, pyridylene, azetidinylene, pyrrolidinylene, piperidinylene, pyrazolylene, thiazolylene, oxadiazolylene, imidazolylene, and benzimidazolylene; wherein said phenylene may be optionally substituted with one or two substituents independently selected from: halogen, OH, $C_{1-4}$ alkyl, $C_{1-4}$ haloalkyl, and $C_{1-4}$ alkyoxy;

alternatively, $R^4$-L- is

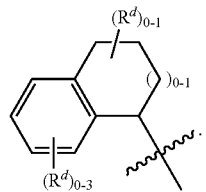

6. A compound according to claim 5, wherein:

$R^1$ is independently selected from the group consisting of: H, $C_{1-4}$ alkyl, phenyl, 4-halo-phenyl, benzyl, and 2-($C_{1-4}$ alkoxy)-5-halo-benzyl;

$R^{2a}$ is independently selected from the group consisting of: H, halogen, CF$_3$, OCF$_3$, and $C_{1-4}$ alkyl;

$R^{2b}$ is independently selected from the group consisting of: H and halogen;

$R^{2c}$ is independently selected from the group consisting of: H, halogen, CF$_3$, OCF$_3$, $C_{1-4}$ alkyl, $C_{1-4}$ alkoxy, CN, NH$_2$, NO$_2$, CONH$_2$, and 4-halo-Ph;

$R^4$ is independently selected from the group consisting of: phenyl, 2-halo-phenyl, 3-halo-phenyl, 4-halo-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-CF$_3$-phenyl, 3-CF$_3$-phenyl, 4-CF$_3$-phenyl, 3-OCF$_3$-phenyl, 4-OCF$_3$-phenyl, 3-CO$_2$($C_{1-4}$ alkyl)-phenyl, 4-CO$_2$($C_{1-4}$ alkyl)-phenyl, 2-NO$_2$-phenyl, 3-NO$_2$-phenyl, 4-NO$_2$-phenyl, 2-($C_{1-4}$ alkyl)-6-($C_{1-4}$ alkyl)-phenyl, 2-halo-3-halo-phenyl, 2-halo-4-halo-phenyl, 3-halo-4-halo-phenyl, 2-halo-6-halo-phenyl, 2-CF$_3$-4-halo-phenyl, 1-naphthyl, 2-naphthyl, 1-pyrrolidinyl, 2-thienyl, 1-pyrrolyl, 1-pyrazolyl, 1,2,3-thiadiazol-4-yl, tetrazol-1-yl, 5-($C_{1-4}$ alkyl)-1,2,4-oxadiazol-3-yl, 1-piperidinyl, 3-($C_{1-4}$ alkyl)-piperidin-1-yl, 4-($C_{1-4}$ alkyl)-piperidin-1-yl, 4-OH-piperidin-1-yl, 4-phenyl-piperidin-1-yl, 4-phenyl-4-OH-piperidin-1-yl, 4-CO$_2$($C_{1-4}$ alkyl)-piperazin-1-yl, 4-Cbz-piperazin-1-yl, 4-($C_{1-4}$ alkyl)-piperazin-1-yl, 4-CH$_2$CH$_2$OH-piperazin-1-yl, 4-morpholinyl, 1H-indol-4-yl,

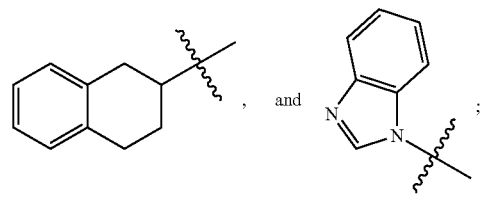 [SMILES: *C1CCc2ccccc2C1 ; *n1cnc2ccccc21]

and

L is independently selected from the group consisting of: $C_{1-4}$ alkylene, —O—$C_{2-4}$ alkylene-, —S—$C_{2-4}$ alkylene-, —$C_{0-2}$ alkylene-(1,2-phenylene)-$C_{0-2}$ alkylene-, —$C_{0-2}$ alkylene-(1,3-phenylene)-$C_{0-2}$ alkylene-, —$C_{0-2}$ alkylene-(1,4-phenylene)-$C_{0-2}$ alkylene-, —NH-(1,3-phenylene)-$C_{0-2}$ alkylene-, —O-(1,4-phenylene)-$C_{0-2}$ alkylene-, -(1,2-phenylene)-O—$C_{0-3}$ alkylene-, -(1,3-phenylene)-O—$C_{0-3}$ alkylene-, -(1,4-phenylene)-O—$C_{0-3}$ alkylene-, —O-(1,4-phenylene)-O—$C_{0-3}$ alkylene-, —SO$_2$-(1,4-phenylene)-$C_{0-2}$ alkylene-,

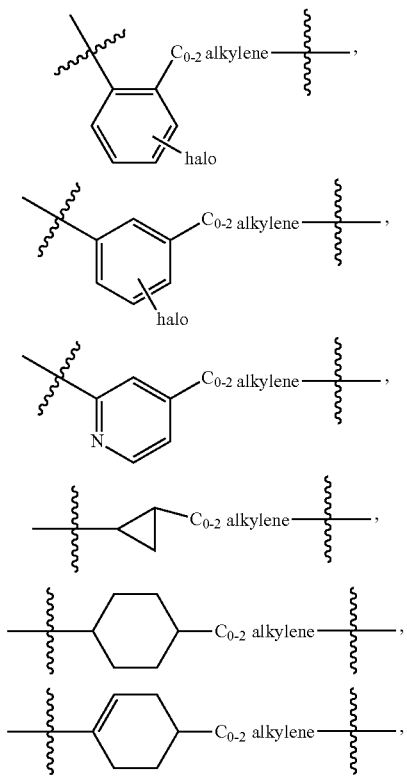

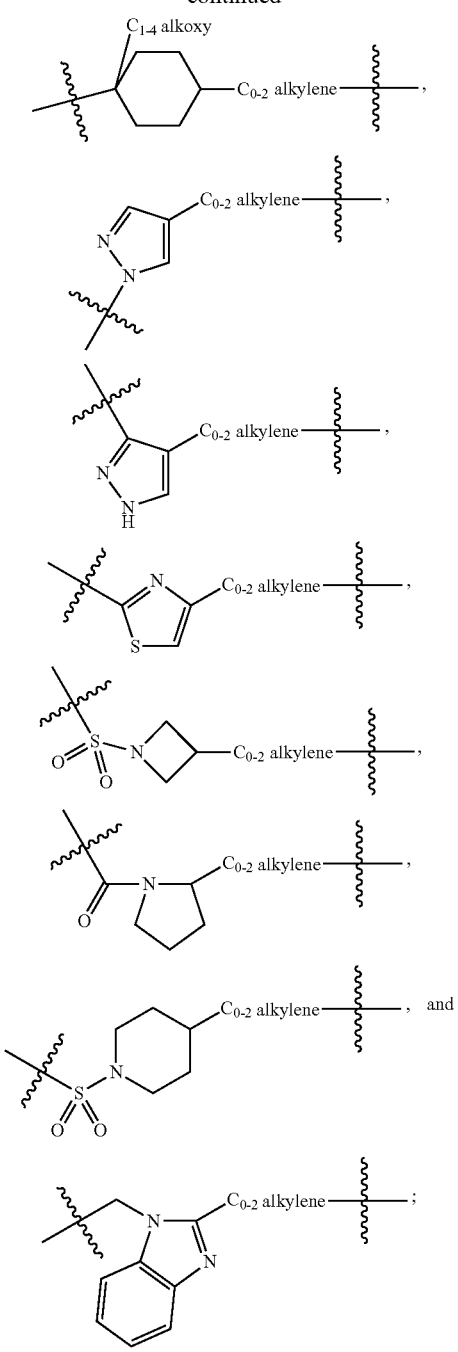

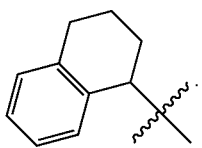

wherein each said alkylene may be straight or branched; alternatively, R⁴-L- is

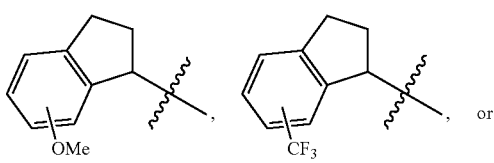

7. A compound according to claim 6, wherein:

$R^1$ is independently selected from the group consisting of: H, methyl, isopropyl, isobutyl, phenyl, 4-Br-phenyl, benzyl, and 2-OCH₃-5-Cl-benzyl;

$R^{2a}$ is independently selected from the group consisting of: H, F, CF₃, OCF₃, and methyl;

$R^{2b}$ is independently selected from the group consisting of: H and Cl;

$R^{2c}$ is independently selected from the group consisting of: H, F, Cl, Br, I, CF₃, OCF₃, methyl, methoxy, CN, NH₂, NO₂, CONH₂, and 4-F-Ph;

$R^4$ is independently selected from the group consisting of: phenyl, 2-F-phenyl, 3-F-phenyl, 4-F-phenyl, 2-Cl-phenyl, 3-Cl-phenyl, 4-Cl-phenyl, 3-methyl-phenyl, 4-methyl-phenyl, 2-methoxy-phenyl, 3-methoxy-phenyl, 4-methoxy-phenyl, 2-CF₃-phenyl, 3-CF₃-phenyl, 4-CF₃-phenyl, 3-OCF₃-phenyl, 4-OCF₃-phenyl, 3-CO₂Me-phenyl, 4-CO₂Me-phenyl, 2-NO₂-phenyl, 3-NO₂-phenyl, 4-NO₂-phenyl, 2,6-dimethyl-phenyl, 2,3-dichloro-phenyl, 2,4-dichloro-phenyl, 3,4-dichloro-phenyl, 2,6-dichloro-phenyl, 2-CF₃-4-F-phenyl, 1-naphthyl, 2-naphthyl, 1-pyrrolidinyl, 2-thienyl, 1-pyrrolyl, 1-pyrazolyl, 1,2,3-thiadiazol-4-yl, 5-methyl-1,2,4-oxadiazol-3-yl, 1-piperidinyl, 4-phenyl-piperidin-1-yl, 4-phenyl-4-OH-piperidin-1-yl, 4-methyl-piperidin-1-yl, 4-Boc-piperazin-1-yl, 4-Cbz-1-piperazinyl, 4-CH₂CH₂OH-piperazin-1-yl, 4-morpholinyl,

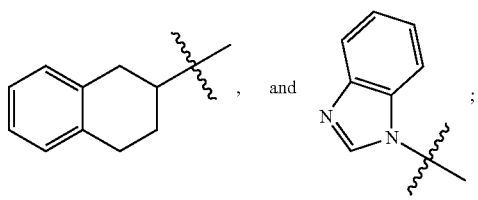 [SMILES: *C1CCc2ccccc2C1 ; *n1cnc2ccccc21]

and

L is independently selected from the group consisting of: —CH₂—, —CH(CH₃)—, —CH(CH₂CH₃)—, —(CH₂)₂—, —(CH₂)₃—, —(CH₂)₂CH(CH₃)—, —OCH(CH₃)CH₂—, —OCH₂CH(CH₃)—, —O(CH₂)₂CH(CH₃)—, —O(CH₂)₂—, —O(CH₂)₃—, —O(CH₂)₄—, —S(CH₂)₃—, -(1,2-phenylene)-CH₂—, -(1,3-phenylene)-CH₂—, -(1,4-phenylene)-CH₂—, -(1,4-phenylene)-(CH₂)₂—, —CH₂-(1,3-phenylene)-CH₂—, —CH₂-(1,4-phenylene)-CH₂—, -(1,3-phenylene)-CH(CH₃)—, —NH-(1,3-phenylene)-CH(CH₃)—, —O-(1,4-phenylene)-CH₂—, -(1,2-phenylene)-O(CH₂)₃—, -(1,3-phenylene)-O(CH₂)₃—, -(1,4-phenylene)-O(CH₂)₃—, —O-(1,4-phenylene)-O(CH₂)₃—, —(CH₂)₂O-(1,3-phenylene)-CH₂—, —SO₂-(1,4-phenylene)-CH₂—,

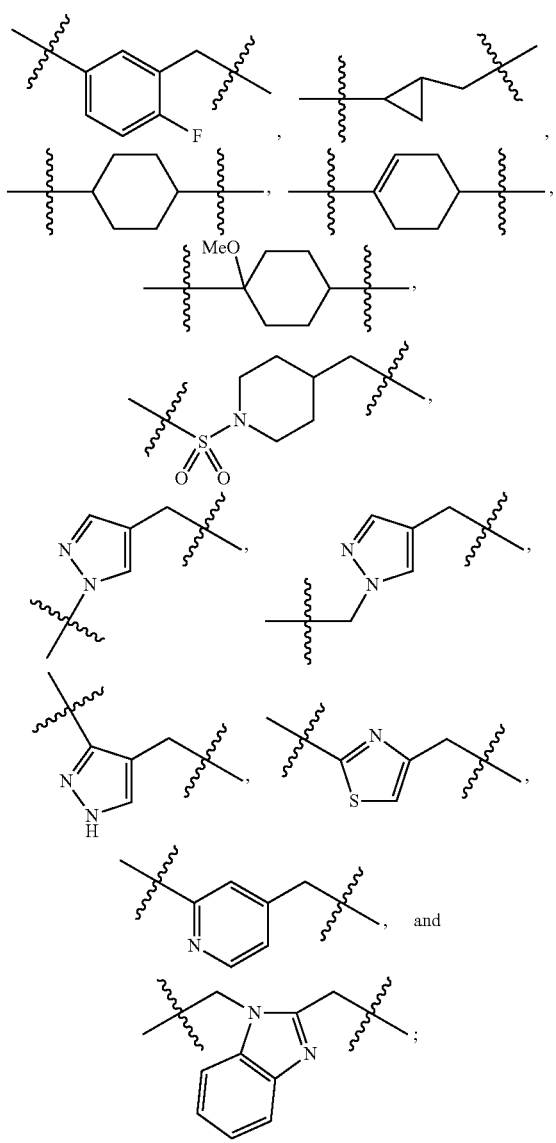

alternatively, R⁴-L- is

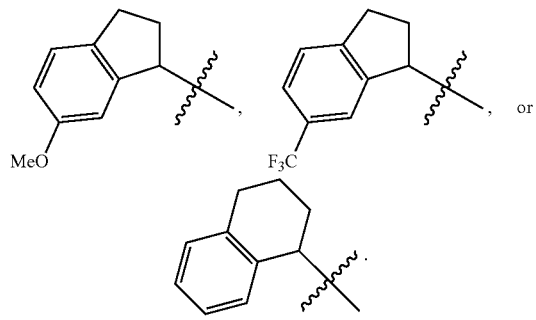

8. A compound according to claim 7, wherein:
R¹ is independently selected from the group consisting of: H, methyl, isopropyl, isobutyl, phenyl, 4-Br-phenyl, benzyl, and 2-OCH₃-5-Cl-benzyl;
R$^{2a}$ is independently selected from the group consisting of: H, F, OCF₃, and methyl;
R$^{2b}$ is independently selected from the group consisting of: H and Cl;

R$^{2c}$ is independently selected from the group consisting of: H, F, Cl, Br, I, CF₃, OCF₃, methyl, methoxy, CN, NH₂, and NO₂;
R⁴ is independently selected from the group consisting of: phenyl, 2-F-phenyl, 3-F-phenyl, 4-F-phenyl, 2-Cl-phenyl, 4-Cl-phenyl, 3-methyl-phenyl, 4-methyl-phenyl, 2-methoxy-phenyl, 3-methoxy-phenyl, 4-methoxy-phenyl, 2-CF₃-phenyl, 3-CF₃-phenyl, 4-CF₃-phenyl, 3-OCF₃-phenyl, 4-OCF₃-phenyl, 3-CO₂Me-phenyl, 4-CO₂Me-phenyl, 2-NO₂-phenyl, 3-NO₂-phenyl, 4-NO₂-phenyl, 2,6-dimethyl-phenyl, 2,3-dichloro-phenyl, 2,4-dichloro-phenyl, 3,4-dichloro-phenyl, 2,6-dichloro-phenyl, 1-naphthyl, 1-pyrrolyl, 1-piperidinyl, 4-phenyl-4-OH-piperidin-1-yl, 4-Boc-piperazin-1-yl, 4-Cbz-1-piperazinyl,

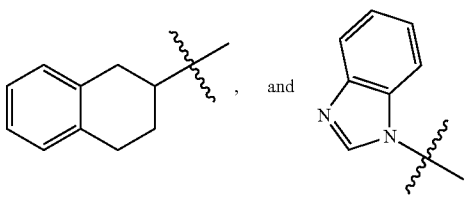

and
L is independently selected from the group consisting of:
—CH₂—, —CH(CH₂CH₃)—, —(CH₂)₂—, —(CH₂)₃—, —(CH₂)₂CH(CH₃)—, —OCH₂CH(CH₃)—, —O(CH₂)₂CH(CH₃)—, —O(CH₂)₃—, —O(CH₂)₄—, —S(CH₂)₃—, -(1,2-phenylene)-CH₂—, -(1,3-phenylene)-CH₂—, -(1,4-phenylene)-CH₂—, -(1,3-phenylene)-CH(CH₃)—, —O-(1,4-phenylene)-CH₂—, -(1,2-phenylene)-O(CH₂)₃—, -(1,3-phenylene)-O(CH₂)₃—, -(1,4-phenylene)-O(CH₂)₃—, —O-(1,4-phenylene)-O(CH₂)₃—,

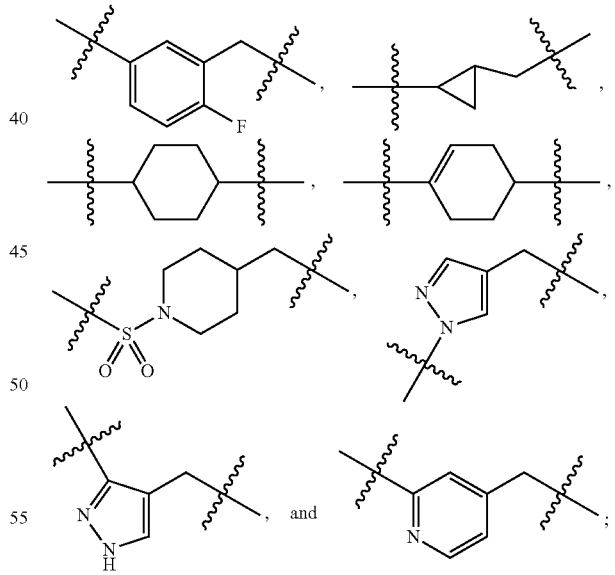

alternatively, R⁴-L- is

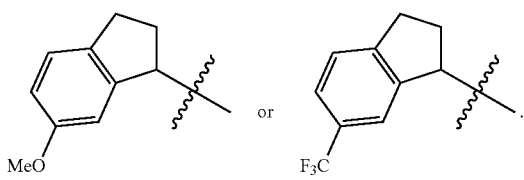 [SMILES: *C1CCc2ccc(OC)cc21 ; *C1CCc2ccc(C(F)(F)F)cc21]

9. A compound according to claim 8, wherein:

$R^4$ is independently selected from the group consisting of: phenyl, 2-F-phenyl, 3-F-phenyl, 4-F-phenyl, 2-Cl-phenyl, 3-Cl-phenyl, 4-Cl-phenyl, 3-methyl-phenyl, 4-methyl-phenyl, 2-methoxy-phenyl, 3-methoxy-phenyl, 4-methoxy-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2$Me-phenyl, 4-$CO_2$Me-phenyl, 2-$NO_2$-phenyl, 3-$NO_2$-phenyl, 4-$NO_2$-phenyl, 2,6-dimethyl-phenyl, 2,3-dichloro-phenyl, 2,4-dichloro-phenyl, 3,4-dichloro-phenyl, 2,6-dichloro-phenyl, 2-$CF_3$-4-F-phenyl, 1-naphthyl, 2-naphthyl, and

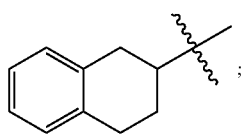 [SMILES: *C1CCc2ccccc2C1]

and

L is independently selected from the group consisting of:
—$CH_2$—, —$CH(CH_3)$—, —$CH(CH_2CH_3)$—, —$(CH_2)_2$—, —$(CH_2)_3$—, —$(CH_2)_2CH(CH_3)$—, —$OCH(CH_3)CH_2$—, —$OCH_2CH(CH_3)$—, —$O(CH_2)_2CH(CH_3)$—, —$O(CH_2)_2$, —$O(CH_2)_3$, —$O(CH_2)_4$—, and —$S(CH_2)_3$—.

10. A compound according to claim 9, wherein:

$R^4$ is independently selected from the group consisting of: phenyl, 4-F-phenyl, 4-Cl-phenyl, 4-methyl-phenyl, 2-$CF_3$-phenyl, 4-$CF_3$-phenyl, 3,4-dichloro-phenyl, 1-pyrrolidinyl, 2-thienyl, 1-pyrrolyl, 1-pyrazolyl, 1,2,3-thiadiazol-4-yl, 5-methyl-1,2,4-oxadiazol-3-yl, 1-piperidinyl, 4-phenyl-piperidin-1-yl, 4-phenyl-4-OH-piperidin-1-yl, 4-methyl-piperidin-1-yl, 4-Boc-piperazin-1-yl, 4-Cbz-1-piperazinyl, 4-$CH_2CH_2OH$-piperazin-1-yl, 4-morpholinyl, and

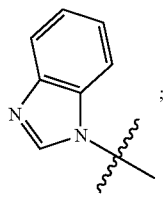 [SMILES: *n1cnc2ccccc21]

and

L is independently selected from the group consisting of:
-(1,2-phenylene)-$CH_2$—, -(1,3-phenylene)-$CH_2$—, -(1,4-phenylene)-$CH_2$—, -(1,4-phenylene)-$(CH_2)_2$—, —$CH_2$-(1,3-phenylene)-$CH_2$—, —$CH_2$-(1,4-phenylene)-$CH_2$—, -(1,3-phenylene)-$CH(CH_3)$—, —NH-(1,3-phenylene)-$CH(CH_3)$—, —O-(1,4-phenylene)-$CH_2$—, -(1,2-phenylene)-$O(CH_2)_3$—, -(1,3-phenylene)-$O(CH_2)_3$—, -(1,4-phenylene)-$O(CH_2)_3$—, —O-(1,4-phenylene)-$O(CH_2)_3$—, —$(CH_2)_2$O-(1,3-phenylene)-$CH_2$—, —$SO_2$-(1,4-phenylene)-$CH_2$—,

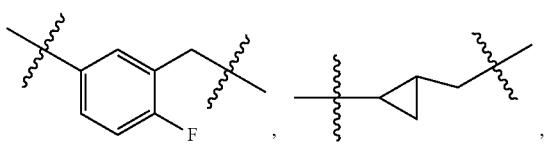

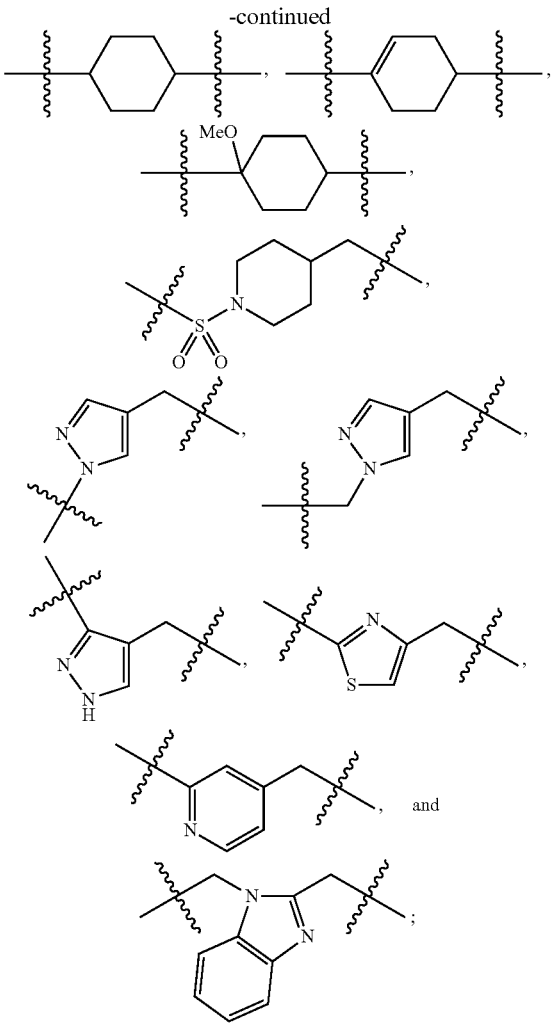

alternatively, $R^4$-L- is

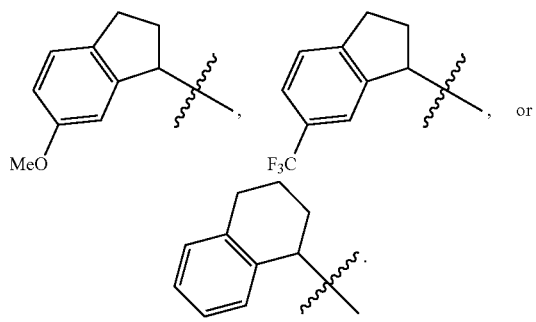

11. A compound according to claim 10, wherein:

$R^4$ is independently selected from the group consisting of: phenyl, 2-F-phenyl, 3-F-phenyl, 4-F-phenyl, 2-Cl-phenyl, 4-Cl-phenyl, 3-methyl-phenyl, 4-methyl-phenyl, 2-methoxy-phenyl, 3-methoxy-phenyl, 4-methoxy-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2$Me-phenyl, 4-$CO_2$Me-phenyl, 2-$NO_2$-phenyl, 3-$NO_2$-phenyl, 4-$NO_2$-phenyl, 2,6-dimethyl-phenyl, 2,3-dichloro-phenyl, 2,4-dichloro-phenyl, 3,4-dichloro-phenyl, 2,6-dichloro-phenyl, 1-naphthyl, and

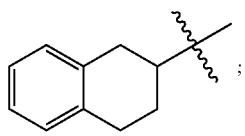 [SMILES: *C1CCc2ccccc2C1]

and

L is independently selected from the group consisting of:
—CH$_2$—, —CH(CH$_2$CH$_3$)—, —(CH$_2$)$_2$—, —(CH$_2$)$_3$—, —(CH$_2$)$_2$CH(CH$_3$)—, —OCH$_2$CH(CH$_3$)—, —O(CH$_2$)$_2$CH(CH$_3$)—, —O—(CH$_2$)$_3$—, —O(CH$_2$)$_4$—, and —S(CH$_2$)$_3$—.

12. A compound according to claim 11, wherein:

R$^4$ is independently selected from the group consisting of: phenyl, 4-F-phenyl, 4-methyl-phenyl, 3,4-dichlorophenyl, 1-pyrrolyl, 1-piperidinyl, 4-phenyl-4-OH-piperidin-1-yl, 4-Boc-piperazin-1-yl, 4-Cbz-1-piperazinyl, and

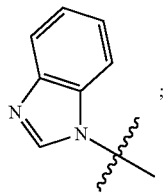 [SMILES: *n1cnc2ccccc21]

and

L is independently selected from the group consisting of:
-(1,2-phenylene)-CH$_2$—, -(1,3-phenylene)-CH$_2$—, -(1,4-phenylene)-CH$_2$—, -(1,3-phenylene)-CH(CH$_3$)—, —O-(1,4-phenylene)-CH$_2$—, -(1,2-phenylene)-O(CH$_2$)$_3$—, -(1,3-phenylene)-O(CH$_2$)$_3$—, -(1,4-phenylene)-O(CH$_2$)$_3$—, —O-(1,4-phenylene)-O(CH$_2$)$_3$—,

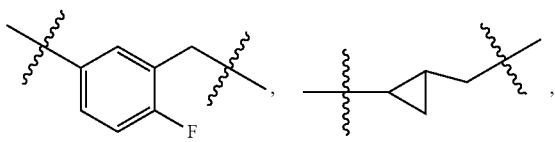

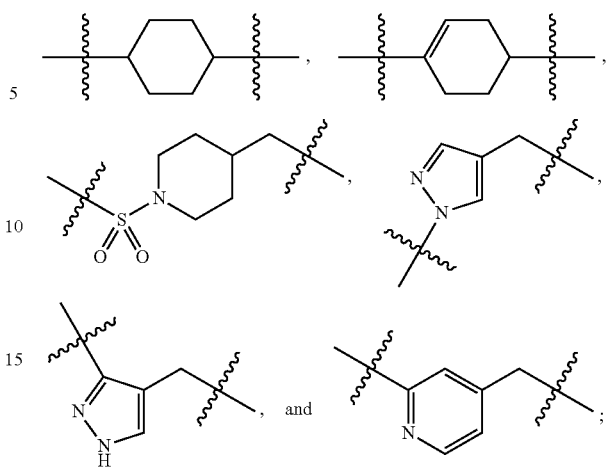

alternatively, R$^4$-L- is

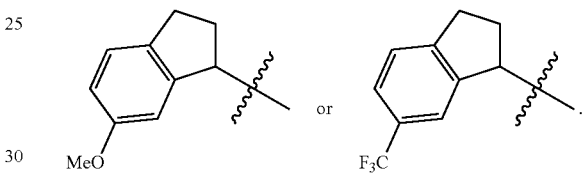

13. A compound according to claim 1, wherein the compound is selected from the exemplified examples, or a stereoisomer, a tautomer, or a pharmaceutically acceptable salt thereof.

14. A pharmaceutical composition, comprising: a pharmaceutically acceptable carrier and a compound of claim 1.

* * * * *